US012749558B2

(12) United States Patent
Babaie et al.

(10) Patent No.: US 12,749,558 B2
(45) Date of Patent: Sep. 29, 2026

(54) SYSTEM AND METHOD FOR MAPPING MOLECULES INTO INTERFACES

(71) Applicant: KISOJI BIOTECHNOLOGY INC., Montréal (CA)

(72) Inventors: Morteza Babaie, Montréal (CA); Benyamin Ghojogh, Montréal (CA); Richard Wargachuk, Montréal (CA); Luis Da Cruz, Montréal (CA); Gordon Ngan, Montréal (CA); David S. F. Young, Montréal (CA)

(73) Assignee: KISOJI BIOTECHNOLOGY INC., Montreal (CA)

( * ) Notice: Subject to any disclaimer, the term of this patent is extended or adjusted under 35 U.S.C. 154(b) by 0 days.

(21) Appl. No.: 18/980,953

(22) Filed: Dec. 13, 2024

(65) Prior Publication Data

US 2025/0201352 A1 Jun. 19, 2025

Related U.S. Application Data

(60) Provisional application No. 63/609,755, filed on Dec. 13, 2023.

(51) Int. Cl.

| | |
|---|---|
| ***G01N 33/48*** | (2006.01) |
| ***G01N 33/50*** | (2006.01) |
| ***G16B 15/20*** | (2019.01) |
| ***G16B 15/30*** | (2019.01) |
| ***G16B 40/30*** | (2019.01) |
| ***G16B 45/00*** | (2019.01) |

(52) U.S. Cl.

CPC ............. *G16B 45/00* (2019.02); *G16B 15/20* (2019.02); *G16B 15/30* (2019.02); *G16B 40/30* (2019.02)

(58) Field of Classification Search

CPC ........ G16B 45/00; G16B 15/20; G16B 15/30; G16B 40/30

See application file for complete search history.

(56) References Cited

PUBLICATIONS

Liu et al. Serum antibody repertoire profiling using in silico antigen screen. PLoS One, vol. 8, article e67181, 11 pages. (Year: 2013).*

Pintilie et al. Comparison of Segger and other methods for segmentation and rigid-body docking of molecular components in Cryo-EM density maps. Biopolymers, vol. 97, pp. 742-760. (Year: 2012).*

Pettersen et al. UCSF Chimera—A visualization system for exploratory research and analysis. Journal of Computational Chemistry, vol. 25, pp. 1605-1612. (Year: 2004).*

Pettersen et al. UCSF ChimeraX: Structure visualization for researchers, educators, and developers. Protein Science, vol. 30, pp. 70-82. (Year: 2021).*

Daberdaku et al. Antibody interface prediction with 3D Zernike descriptors and SVM. Bioinformatics, vol. 35, pp. 1870-1876. (Year: 2019).*

PCT, International Search Report and Written Opinion for International Application No. PCT/CA2024/051663 dated Feb. 17, 2025.

Waterhouse et al., "Jalview Version 2—a multiple sequence alignment editor and analysis workbench", May 2009, Bioinformatics, vol. 25, Issue 9, pp. 1189-1191 (https://doi.org/10.1093/bioinformatics/btp033).

Makhzani et al., "Adversarial Autoencoders", arXiv:1511.05644v2 [cs.LG] May 25, 2016.

Vaswani et al., "Attention Is All You Need", 31st Conference on Neural Information Processing Systems (NIPS 2017), Long Beach, CA, USA.

Kingma et al., "Auto-Encoding Variational Bayes", arXiv:1312.6114v11 [stat.ML] Dec. 10, 2022.

Gainza et al., "Deciphering interaction fingerprints from protein molecular surfaces using geometric deep learning", Nature Methods | vol. 17 | Feb. 2020 | 184-192 | www.nature.com/naturemethods.

Ghojogh et al., "Elements of Dimensionality Reduction and Manifold Learning", ISBN 978-3-031-10601-9 ISBN 978-3-031-10602-6 (eBook) https://doi.org/10.1007/978-3-031-10602-6.

Kipf et al., "Semi-Supervised Classification With Graph Convolutional Networks", arXiv:1609.02907v4 [cs.LG] Feb. 22, 2017.

Mcinnes et al., "UMAP: Uniform Manifold Approximation and Projection for Dimension Reduction", arXiv:1802.03426v3 [stat.ML] Sep. 18, 2020.

Van Der Maaten et al., "Visualizing Data using t-SNE", Journal of Machine Learning Research 9 (2008) 2579-2605 Submitted May 2008; Revised Sep. 2008; Published Nov. 2008.

* cited by examiner

*Primary Examiner* — Russell S Negin

(74) *Attorney, Agent, or Firm* — Norton Rose Fulbright Canada LLP

(57) ABSTRACT

Embodiments described herein relate to systems and methods for mapping molecules into interfaces. An example interface includes a visual interface having a map visualization. Example molecules include proteins, or any protein-like molecules or fragments thereof such as antibodies, antigens, proteins, lectins, receptors. Embodiments described herein relate to systems and methods for mapping molecules into interfaces by processing data using dimensionality reduction to generation representations of molecule maps (e.g. map visualizations).

25 Claims, 34 Drawing Sheets
(27 of 34 Drawing Sheet(s) Filed in Color)

Specification includes a Sequence Listing.

800

Geometrical regions of antibodies for binding to a specific target

SYSTEM AND METHOD FOR MAPPING MOLECULES INTO INTERFACES

CROSS-REFERENCE

This application claims priority from U.S. provisional patent application 63/609,755, titled "SYSTEM AND METHOD FOR MAPPING MOLECULES INTO INTERFACES", filed on 13 Dec. 2023, the entire contents of which are incorporated herein by reference.

INCORPORATION BY REFERENCE TO SEQUENCE LISTING

The present application is being filed along with a Sequence Listing submitted electronically in XML format. The Sequence Listing file "10255708-1US Seq Listings.xml" is created on Mar. 12, 2026, which is 3,710 bytes in size. The contents of the Sequence Listing are incorporated by reference herein in its entirety.

FIELD

This disclosure relates to computing, selective visual display systems, data processing, molecule discovery, machine learning, and interfaces for devices.

BACKGROUND

Finding molecules with similar properties and/or features can help in identifying possible drugs for treatment of diseases. However, it can be difficult to visualize molecules across a plurality of properties and/or features. This can make it difficult to discover new effective treatments.

There is need for improved or alternate ways of molecule discovery.

SUMMARY

Embodiments described herein relate to systems and methods for mapping molecules into interfaces, generating maps for display and interaction, or providing interfaces or maps. Molecules can be organized into groups, and then sorted or sampled for molecule discovery. The systems and methods described herein can be used for mapping protein, protein-like molecules, such as antibodies or antigens, or fragments thereof, small molecule drugs or biomolecules. There is need for improved or alternate ways of molecule discovery.

The systems and methods of the present disclosure can be used for different applications such as for example, drug discovery, antibody discovery or optimization (e.g., format conversion, humanization), monitoring immune responses (e.g., further to immunization or vaccination), diagnosis, monitoring of disease progression etc. The systems and methods of the present disclosure may particularly find utility in prospective drug discovery.

In antibody discovery, understanding the diversity and specificity of immune responses can be important for identifying not only novel binders but also antibodies with better therapeutic potential. Described herein are visualization methods that can enable the structural and biophysical comparison of antibody repertoires by representing each antibody/antigen or each part of antibody/antigen as a point on a map, where spatial arrangements reflect their similarities. The systems and methods described herein can aid in analyzing the quality of antibody immune response by paratope diversity, assessing impact of immunization methods or of different genetic backgrounds on antibody paratope diversity, and sampling antibody paratopes for therapeutic activity.

In accordance with one aspect, there is provided a computer-implemented system for mapping molecules into interfaces. The system has: a processing subsystem that includes one or more processors and one or more memories coupled with the one or more processors, the processing subsystem configured to cause the system to: receive input molecules, wherein the input molecules are a set or multiple sets of one or more molecules, wherein each molecule is defined as a sequence of information, structure, or properties; encode the sequence of information, structure, or properties; generate a dataset by processing the input molecules, wherein the dataset comprises the encoded sequence of information, three-dimensional coordinates of the sequence of information for each molecule to define structure of the molecule, and features; transform the dataset to generate a molecule map and the features by feature extraction to reduce a higher number of dimensions into lower dimensional data representations that can be indicated by the interface while capturing valuable data in the lower-dimensional data representations; generate a map user interface comprising the molecule map as a representation of the lower dimensional data representations of the dataset; and provide the map user interface.

In some embodiments, the map user interface comprises a visual interface, and wherein the lower dimensional data representations can be visualized in the visual interface.

In some embodiments, the input molecules are antibodies or antigen binding fragments thereof and/or antigens, and wherein the molecule map is a paratope map.

In some embodiments, the input molecules are antigens, and wherein the molecule map is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, and generative models.

In some embodiments, the system has a data storage device of a databank of molecules, wherein each molecule is assigned a unique index.

In some embodiments, the system compares a molecule to the bank of molecules and assigns the molecule to an index of a closest molecule in the bank of molecules, wherein molecules assigned to the same index have similar sequences, structures, or properties.

In some embodiments, the feature extraction comprises layer-wise embedding, wherein, for multiple datasets or multiple parts of a dataset, features of each of the multiple datasets or each of the multiple parts of the dataset are extracted together or separately.

In some embodiments, the features can be plotted as layers of visualization on top of each other.

In some embodiments, the map user interface comprising the visualization of the dataset has control inputs to enable viewing of the layers separately or in relation to other layers.

In some embodiments, one or more layers are used for training for the feature extraction, and one or more other layers are used for testing the feature extraction.

In some embodiments, the feature extraction comprises arranging embeddings in clusters.

In some embodiments, the feature extraction comprises embedding individual molecules.

In some embodiments, the feature extraction comprises generating clusters around molecules of interest.

In some embodiments, the feature extraction comprises sampling from the molecule map.

In some embodiments, the feature extraction comprises coding scores in the molecule map.

In some embodiments, the map user interface comprises a visualization of extracted features of the dataset.

In some embodiments, the system has a user device to display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface comprises a visualization of clusters around molecules of interest.

In some embodiments, the map user interface comprises one or more clusters of molecules.

In some embodiments, the processing subsystem performs feature extraction for individual molecules of the dataset to obtain individual molecule embeddings.

In some embodiments, the layer-wise embedding comprises individual molecule embeddings.

In some embodiments, a user interface uses the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence or structure or properties of one or more of the antibodies or antigen binding fragments.

In some embodiments, the input molecules comprise antigens and wherein the information comprises the amino acid sequence of one or more of the antigens.

In some embodiments, the system allows a user to modify the amino acid sequence and wherein the system predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the information provided by the system is used to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, or chimeric antibody.

In some embodiments, the processing subsystem concatenates features of parts of a molecule together to have a total feature for the molecule.

In some embodiments, the antibodies or antigen binding fragments thereof comprise antibodies from a species including, but not limited to, mice, bovine, rabbits, camels, llamas, humans, alpaca, and standard species.

In some embodiments, the encoded sequence of information refers to an encoded amino acid sequence or structure or properties.

In some embodiments, the processing subsystem outputs a selected molecule.

In some embodiments, there is provided a manufacture obtained by the selected molecule output of the computer-implemented system.

In some embodiments, there is provided a product obtained by the computer-implemented system.

In accordance with another aspect, there is provided a computer-implemented method for mapping molecules into visual interfaces. The method involves: receiving input molecules, wherein the input molecules are a set or multiple sets of one or more molecules, wherein each molecule is defined as a sequence of information; encoding the sequence of information; generating a dataset by processing the input molecules, wherein the dataset comprises the encoded sequence of information, three-dimensional coordinates of the sequence of information for each molecule to define structure of the molecule, biophysical properties, the features and the fingerprints; transforming the dataset to generate a molecule map by feature extraction and fingerprint generation to reduce a higher number of dimensions into lower dimensional data representations that can be indicated by the interface while capturing valuable data in the lower-dimensional data representations; generating a map user interface comprising the molecule map as a representation of the lower dimensional data representations of the dataset; and providing the map user interface.

In some embodiments, the map user interface comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map is a paratope map.

In some embodiments, the input molecules are antigens, and wherein the molecule map is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, and generative models.

In some embodiments, the method involves storing, in a data storage device, a databank of molecules, wherein each molecule is assigned a unique index.

In some embodiments, the method involves comparing a molecule to the bank of molecules and assigning the molecule to an index of a closest molecule in the bank of molecules, wherein molecules assigned to the same index have similar sequences, structures, or properties.

In some embodiments, the method involves feature extraction with layer-wise embedding, wherein, for multiple datasets or multiple parts of a dataset, features of each of the multiple datasets or each of the multiple parts of the dataset are extracted together or separately.

In some embodiments, the features can be plotted as layers of visualization on top of each other.

In some embodiments, the method involves providing the map user interface comprising the visualization of the dataset with control inputs to enable viewing of the layers separately or in relation to other layers.

In some embodiments, one or more layers are used for training for the feature extraction, and one or more other layers are used for testing the feature extraction.

In some embodiments, the feature extraction comprises arranging embeddings in clusters.

In some embodiments, the feature extraction comprises embedding individual molecules.

In some embodiments, the feature extraction comprises generating clusters around molecules of interest.

In some embodiments, the feature extraction comprises sampling from the molecule map.

In some embodiments, the feature extraction comprises coding scores in the molecule map.

In some embodiments, the map user interface comprises a visualization of extracted features of the dataset.

In some embodiments, the method involves using an user device to display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the method involves using the map user interface to provide a visualization of clusters around molecules of interest.

In some embodiments, the map user interface comprises one or more clusters of molecules.

In some embodiments, the method involves performing feature extraction for individual molecules of the dataset to obtain individual molecule embeddings.

In some embodiments, the layer-wise embedding comprises individual molecule embeddings.

In some embodiments, the method involves using the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the method involves modifying the amino acid sequence and wherein the system predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the method allows a user to import further molecules and determine similarity with the input molecules.

In some embodiments, the molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the method involves using the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, or chimeric antibody.

In some embodiments, the method involves concatenating features of parts of a molecule together to have a total feature for the molecule.

In some embodiments, the encoded sequence of information refers to an encoded amino acid sequence.

In some embodiments, the method involves outputting a selected molecule.

In some embodiments, there is provided a manufacture obtained by the selected molecule output of the computer-implemented method.

In some embodiments, there is provided a product obtained by the computer-implemented method.

In some embodiments, the method involves a step of producing a molecule identified or selected from the map user interface.

In some embodiments, there is provided a product obtained by the computer-implemented method.

In some embodiments, the product is an antibody or an antigen binding fragment thereof.

In accordance with another aspect, there is provided a non-transitory computer-readable medium or media having stored thereon machine interpretable instructions which, when executed by a processing subsystem, cause the processing subsystem to perform a method for mapping molecules into visual interfaces, the method comprising: receiving input molecules, wherein the input molecules are a set or multiple sets of one or more molecules, wherein each molecule is defined as a sequence of information, structure, or properties; encoding the sequence of information, structure, or properties; generating a dataset by processing the input molecules, wherein the dataset comprises the encoded sequence of information, three-dimensional coordinates of the sequence of information for each molecule to define structure of the molecule, the features and the fingerprints; transforming the dataset to generate a molecule map by feature extraction and fingerprint generation to reduce a higher number of dimensions into lower dimensional data representations that can be indicated by the interface while capturing valuable data in the lower-dimensional data representations; generating a map user interface comprising the molecule map as a representation of the lower dimensional data representations of the dataset; and providing the map user interface.

In accordance with another aspect, there is provided a computer-implemented system for an interface relating to molecules. The system has: a processing subsystem that includes one or more processors and one or more memories coupled with the one or more processors, the processing subsystem configured to cause the system to: receive input molecules, wherein the input molecules are a set or multiple sets of one or more molecules, wherein each molecule is defined as a sequence of information, structure, or properties; encode the sequence of information, structure, or properties; generate a dataset by processing the input molecules, wherein the dataset comprises the encoded sequence of information, three-dimensional coordinates of the sequence of information for each molecule to define structure of the molecule, the features and the fingerprints; transform the dataset by feature extraction and fingerprint generation to reduce a higher number of dimensions into lower dimensional data representations that can be indicated by the interface while capturing valuable data in the lower-dimensional data representations; generate one or more metrics from the transformed dataset, wherein the one or more metrics comprise lower dimensional data representations of the dataset and summarize characteristics of the input molecules; and provide the one or more metrics to an interface.

In accordance with another aspect, there is provided a computer-implemented system for a visual interface for mapping molecules. The system has: a processing subsystem that includes one or more processors and one or more memories coupled with the one or more processors, the processing subsystem providing a map user interface, wherein the map user interface: receives input molecules, wherein the input molecules are a set or multiple sets of one or more molecules, wherein each molecule is defined as a sequence of information, structure, or properties; and provides a map interface comprising a molecule map as a representation of lower dimensional data representations of a dataset for the input molecules, wherein the dataset comprises the sequence of information for each molecule, three-dimensional coordinates of the sequence of information for each molecule to define structure of the molecule, and features; wherein the molecule map comprises a transformation of the dataset by feature extraction and fingerprint generation to reduce a higher number of dimensions into lower dimensional data representations that can be indicated by the interface while capturing valuable data in the lower-dimensional data representations.

In some embodiments, the input molecules are proteins or protein-like molecules comprising antibodies and antigens.

In some embodiments, the antibodies comprise antibodies of a species including, but not limited to, mice, bovine, rabbits, camels, llamas, humans, alpaca, and standard species.

In some embodiments, the input molecules are antibodies and antigens, and wherein the molecule map is a paratope map.

In some embodiments, the input molecules are antigens, and wherein the molecule map is an epitope map.

In some embodiments, the map user interface comprises layer-wise embedding providing layers for the map visualization.

In some embodiments, the map user interface plots features as layers of the map visualization on top of each other.

In some embodiments, the map user interface has control inputs to enable viewing of the layers separately or in relation to other layers.

In some embodiments, the map user interface has control inputs to add or remove a layer of the layers for the map visualization.

In some embodiments, the map user interface comprises a visualization of extracted features of the dataset.

In some embodiments, the map user interface receives one or more reference molecules or target molecules, wherein the transformation of the dataset is based on the one or more reference molecules or target molecules.

In some embodiments, the map user interface receives one or more scores for the molecules, wherein the scores comprise expressibility scores and fuzzy panning scores.

In some embodiments, the map visualization comprises one or more clusters corresponding to the molecules, wherein the map user interface receives cluster control commands to update the map visualization with hyperparameters of the one or more clusters.

In some embodiments, the map visualization displays one or more scores in relation to the molecules, the scores comprising expressibility scores or fuzzy panning scores.

In some embodiments, the map user interface receives a control commands for sampling from at least a portion of the map visualization.

In some embodiments, the map user interface receives a control commands for editing samples drawn from at least a portion of the map visualization.

In some embodiments, the map user interface receives plot settings corresponding to visualization characteristics for the map visualization.

In some embodiments, a user device can display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface comprises a visualization of clusters around molecules of interest.

In some embodiments, the map user interface comprises one or more clusters of molecules.

In some embodiments, the map user interface comprises individual molecule embeddings.

In some embodiments, the layer-wise embedding comprises individual molecule embeddings.

In some embodiments, the map user interface receives scores.

In some embodiments, the map user interface exports files.

In some embodiments, the map user interface comprises one or more buttons for adding or removing layers, one or more buttons for receiving input molecules, one or more buttons for adding or removing individual molecules, and one or more buttons for importing scores.

In some embodiments, the map user interface comprises a plurality of settings selected from the group of navigational settings for the map visualization, plot settings, settings for coding scores in the map visualization, cluster settings, settings for editing samples, sample settings, report settings, map analysis settings, and export settings.

In accordance with an aspect, there is provided a computer-implemented system for mapping proteins, protein-like molecules or fragments thereof into visual interfaces and generating maps for display and interaction. The system includes a processing subsystem that includes one or more processors and one or more memories coupled with the one or more processors, the processing subsystem configured to cause the system to: receive data for a set or multiple sets of one or more input proteins, protein-like molecules or fragments thereof, wherein the data comprises features of the one or more proteins, protein-like molecules or fragments thereof; generate at least one dataset by processing the data for the set or multiple sets of the one or more input proteins, protein-like molecules or fragments thereof; transform one or more of the data and the at least one dataset(s) to generate a map and additional features by feature extraction or feature selection to reduce higher dimensional data representations into lower dimensional data representations for visualization by the visual interface, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generate a visual map interface comprising the map as a visual representation of the lower dimensional data representations of the dataset, the visual representation comprising visualizations representing the dataset as one or more layers of proteins, protein-like molecules or fragments thereof, each layer comprising one or more of the one or more clusters of proteins, protein-like molecules or fragments thereof; and provide the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof; receive commands or detect interactions with the map by the tools at the visual map interface; update the map based on the commands or interactions; and trigger an update to the visual map interface with the updated map.

In some embodiments, the proteins, protein-like molecules or fragments thereof are selected from: antibodies, antigens, lectins, receptors, ligands, enzymes, or fragments thereof.

In some embodiments, the proteins, protein-like molecules or fragments thereof comprises antibodies or fragments thereof and/or antigens or fragments thereof, and wherein the map is a paratope map or an epitope map or a map comprising proteins or protein-like molecules or fragments thereof.

In some embodiments, the proteins, protein-like molecules or fragments thereof comprise antibodies or antibody fragments thereof and wherein the data comprises one or more of the structure of one or more antibodies or antibody fragments thereof, the amino acid sequence of one or more of the antibodies or antibody fragments thereof, amino acid atom or molecule coordinates, and biophysical properties of one or more antibodies or antibody fragments thereof.

In some embodiments, the proteins, protein-like molecules or fragments thereof are selected from conventional antibodies, antibody-like molecules, artificial antibodies, antibody mimetics, single domain antibodies, single chain antibody, humanized antibodies, chimeric antibodies, or fragments thereof.

In some embodiments, the fragments comprise antigen binding fragments or antigen binding domains.

In some embodiments, the antigen binding fragments or the antigen binding domains are selected from one or more complementarity determining regions and/or one or more framework regions, one or more variable domains, or paratope.

In some embodiments, the visual representation of the lower dimensional data representations comprises different colours and/or marker shapes and/or marker sizes and/or color transparencies and/or color gradients to indicate the one or more layers and the one or more clusters of proteins, protein-like molecules or fragments thereof.

In some embodiments, the lower dimensional data representations are one-dimensional, two-dimensional, three-dimensional, or four-dimensional data representations.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, sequence processing algorithms, image processing algorithms, computer vision algorithms, and identity transformation.

In some embodiments, the processing subsystem causes the system to cluster the one or more of the data and the dataset to generate the one or more clusters of proteins, protein-like molecules or fragments thereof.

In some embodiments, the processing subsystem causes the system to encode the raw data and generate additional features from the encoded data.

In some embodiments, the visual representation superimposes the one or more layers of proteins, protein-like molecules or fragments thereof as overlays as part of the visualizations representing the dataset, wherein the tools trigger movement of the one or more layers to different positions or levels, or removal thereof from the map or change of order of displaying the layers or zooming in or out of one or multiple layers or moving in the map across layers.

In some embodiments, the processing subsystem causes the system to implement map analysis, wherein map analysis comprises one or more of generating clusters around proteins, protein-like molecules or fragments thereof of interest, arranging embeddings in clusters, layer-wise embedding, embedding individual proteins, protein-like molecules or fragments thereof, sampling from the map, coding scores in the map, wherein the map contains the one or more clusters and visualizes the one or more clusters.

In some embodiments, the processing subsystem causes the system to generate or calculate one or more clusters of proteins, protein-like molecules or fragments thereof, and wherein the map user interface comprises a visualization of the one or more clusters of proteins, protein-like molecules or fragments thereof.

In some embodiments, feature extraction comprises extracting useful information from the dataset and feature selection comprises selecting a subset of the dataset of proteins, protein-like molecules or fragments thereof.

In some embodiments, the processing subsystem causes the system to transform the one or more of the data and the dataset to generate the map by one or more of sequencing and clustering, sampling, intersection of data subsets, and subtraction of data subsets.

In some embodiments, processing subsystem causes the system to partition or segment the digital map into a plurality of map tiles, label each of the one or more clusters with a corresponding map tile of the plurality of map tiles, and display the one or more clusters within the plurality of map tiles using the labels, wherein the visualization indicates the plurality of map tiles and the one or more clusters.

In some embodiments, the processing subsystem causes the system to: (i) intersect one or more layers of proteins, protein-like molecules or fragments thereof or (ii) subtract one or more layers of proteins, protein-like molecules or fragments thereof or (iii) add one or more layers of proteins, protein-like molecules or fragments thereof, to update the map based on the commands or interactions.

In some embodiments, the tools at the visual map interface comprises a sampling tool for sampling proteins, protein-like molecules or fragments thereof from the one or more clusters of proteins, protein-like molecules or fragments thereof, wherein the processing subsystem causes the system to update the map by sampling proteins, protein-like molecules or fragments thereof in response to activation of the sampling tool and trigger an update to the visual map interface with the updated map to visualize the sampling.

In some embodiments, the processing subsystem causes the system to subtract the unimmunized library of proteins, protein-like molecules or fragments thereof from the immunized library of proteins, protein-like molecules or fragments thereof to filter out nonspecific proteins, protein-like molecules or fragments thereof and to reduce the search space for sampling and searching for specific molecule-candidates for one or multiple targets, wherein if multiple layers or datasets exist for the immunized library, the subsystem causes the system to intersect layers or datasets after subtraction to reduce the search space even further.

In some embodiments, the processing subsystem causes the system to subtract the libraries of proteins, protein-like molecules or fragments thereof immunized against one or multiple targets from the library of proteins, protein-like molecules or fragments thereof immunized against a target of interest, to filter out moieties which are non-binders to the target of interest, and to reduce the search space for sampling and searching for specific molecule-candidates for the target of interest, wherein if multiple layers or datasets exist for the immunized library against the target of interest, the subsystem causes the system to intersect layers or datasets after subtraction to reduce the search space even further.

In some embodiments, the processing subsystem causes the system to export or report the inspection, searching, sampling, clustering, and analysis of the proteins, protein-like molecules or fragments thereof through text, tables, plots, or visualizations.

According to an aspect, there is provided a computer process for mapping proteins, protein-like molecules or fragments thereof into visual interfaces and generating digital maps for display and interaction. The method includes: receiving data for a set or multiple sets of one or more input proteins, protein-like molecules or fragments thereof, wherein the data comprises features of the one or more proteins, protein-like molecules or fragments thereof; generating at least one dataset by processing the data for the set or multiple sets of the one or more input proteins, protein-like molecules or fragments thereof; transforming one or more of the data and the at least one dataset(s) to generate a map and additional features by feature extraction or feature selection to reduce higher dimensional data representations into lower dimensional data representations for visualization by the visual interface, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generating a visual map interface comprising the map as a visual representation of the lower dimensional data representations of the dataset, the visual representation comprising visualizations representing the dataset as one or more layers of proteins, protein-like molecules or fragments thereof, each layer comprising one or more of the one or more clusters of proteins, protein-like molecules or fragments thereof; and providing the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof; receiving commands or detect interactions with the map by the tools at the visual map interface; and triggering an update to the visual map interface and the map based on the commands or interactions.

According to an aspect, there is provided a computer-readable medium encoded with instructions, that when executed by a processor, cause the processor to map proteins, protein-like molecules or fragments thereof into visual interfaces and generate digital maps for display and interaction. The instructions comprising instructions for: receiving data for a set or multiple sets of one or more input proteins, protein-like molecules or fragments thereof, wherein the data comprises features of the one or more proteins, protein-like molecules or fragments thereof; generating at least one dataset by processing the data for the set or multiple sets of the one or more input proteins, protein-like molecules or fragments thereof; transforming one or more of the data and the at least one dataset(s) to generate a map and additional features by feature extraction or feature selection to reduce higher dimensional data representations into lower dimensional data representations for visualization by the visual interface, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generating a visual map interface comprising the map as a visual representation of the lower dimensional data representations of the dataset, the visual representation comprising visualizations representing the dataset as one or more layers of proteins, protein-like molecules or fragments thereof, each layer comprising one or more of the one or more clusters of proteins, protein-like molecules or fragments thereof; and providing the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof; receiving commands or detect interactions with the map by the tools at the visual map interface; and triggering an update to the visual map interface and the map based on the commands or interactions.

According to an aspect, there is provided a computer-implemented system for mapping molecules into interfaces and generating maps for interfaces. The system including a processing subsystem that includes one or more processors and one or more memories coupled with the one or more processors, the processing subsystem configured to cause the system to: receive data for a set or multiple sets of one or more input molecules, wherein the input molecules are a set or multiple sets of one or more molecules, wherein the data comprises features of the molecules; generate at least one dataset by processing the data for the set or multiple sets of the one or more input molecules, wherein the dataset comprises encoded sequences of information, coordinates for each molecule to define structure of the molecule, and features; transform one or more of the data and the at least one dataset to generate a map and additional features by feature extraction or feature selection to reduce higher dimensional data representations into lower dimensional data representations that can be indicated, depicted or visualized by the interface while capturing valuable information in the lower-dimensional data representations, the lower dimensional data representations comprising one or more clusters of the input molecules or newly generated molecules; generate a map user interface comprising the map as a representation of the lower dimensional data representations of the dataset, the representation representing the at least one dataset as one or more layers of molecules, each layer comprising one or more of the one or more clusters of molecules; and provide the map user interface.

In some embodiments, the processing subsystem causes the system to: provide the map user interface with tools for interaction with the map and inspection, searching, sampling, clustering and analysis of the one or more input molecules or newly generated molecules; receive commands or detect interactions with the map by the tools at the visual map interface; update the map based on the commands or interactions; and trigger an update to the map interface with the updated map.

In some embodiments, the molecules are proteins, protein-like molecules, fragments thereof, small molecule drugs, or nucleic acid molecules.

In some embodiments, the input proteins, protein-like molecules or fragments thereof comprises antibodies or fragments thereof and/or antigens or fragments thereof, and wherein the map is a paratope map or an epitope map or a map comprising proteins or protein-like molecules or fragments thereof.

In some embodiments, the proteins, protein-like molecules or fragments thereof are selected from the group consisting of: antibodies, antigen binding fragments, drug candidates, compounds, binding candidates, and binding agents.

In some embodiments, the map user interface comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map is a paratope map.

In some embodiments, the input molecules are antigens, and wherein the molecule map is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, and generative models.

In some embodiments, the system further comprises a data storage device of a databank of molecules, wherein each molecule is assigned a unique index.

In some embodiments, the system compares a molecule to the bank of molecules and assigns the molecule to an index of a closest molecule in the bank of molecules, wherein molecules assigned to the same index have similar sequences, structures, or properties.

In some embodiments, the feature extraction comprises layer-wise embedding, wherein, for multiple datasets or multiple parts of a dataset, features of each of the multiple datasets or each of the multiple parts of the dataset are extracted separately.

In some embodiments, the features can be plotted as layers of visualization on top of each other.

In some embodiments, the map user interface comprising the visualization of the dataset has control inputs to enable viewing of the layers separately or in relation to other layers.

In some embodiments, one or more layers are used for training for the feature extraction, and one or more other layers are used for testing the feature extraction.

In some embodiments, the feature extraction comprises arranging embeddings in clusters.

In some embodiments, the feature extraction comprises embedding individual molecules.

In some embodiments, the feature extraction comprises generating clusters around molecules of interest.

In some embodiments, the feature extraction comprises sampling from the molecule map.

In some embodiments, the feature extraction comprises coding scores in the molecule map.

In some embodiments, the map user interface comprises a visualization of extracted features of the dataset.

In some embodiments, further comprising a user device to display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface comprises a visualization of clusters around molecules of interest.

In some embodiments, the map user interface comprises one or more clusters of molecules.

In some embodiments, the processing subsystem performs feature extraction for individual molecules of the dataset to obtain individual molecule embeddings.

In some embodiments, the layer-wise embedding comprises individual molecule embeddings.

In some embodiments, a user interface uses the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the system allows a user to modify the amino acid sequence and wherein the system predicts the impact of the modification on the features (binding, function, stability, expressibility, affinity, immunogenicity) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, uses the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, or chimeric antibody.

In some embodiments, the processing subsystem concatenates features of parts of a molecule together to have a total feature for the molecule.

In some embodiments, the encoded sequence of information refers to an encoded amino acid sequence.

In some embodiments, the processing subsystem outputs a selected molecule.

According to an aspect, there is provided a manufacture obtained by the selected molecule output of the computer-implemented system described herein.

According to an aspect, there is provided a product obtained by the computer-implemented system described herein.

According to an aspect, there is provided a computer-implemented method for mapping molecules into interfaces and generating maps for interfaces. The method includes: receiving data for a set or multiple sets of one or more input molecules, wherein the input molecules are a set or multiple sets of one or more molecules, wherein the data comprises features of the molecules; generating at least one dataset by processing the data for the set or multiple sets of the one or more input molecules, wherein the dataset comprises encoded sequences of information, coordinates for each molecule to define structure of the molecule, features, and fingerprints; transforming one or more of the data and the at least one dataset to generate a map and additional features by feature extraction, feature selection or fingerprint generation to reduce higher dimensional data representations into lower dimensional data representations that can be indicated, depicted or visualized by the interface while capturing valuable information in the lower-dimensional data representations, the lower dimensional data representations comprising one or more clusters of the input molecules or newly generated molecules; generating a map user interface comprising the map as a representation of the lower dimensional data representations of the dataset, the representation representing the at least one dataset as one or more layers of molecules, each layer comprising one or more of the one or more clusters of molecules; and providing the map user interface.

In some embodiments, the map user interface comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map is a paratope map.

In some embodiments, the input molecules are antigens, and wherein the molecule map is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, and generative models.

In some embodiments, the method further includes storing, in a data storage device, a databank of molecules, wherein each molecule is assigned a unique index.

In some embodiments, the method further includes comparing a molecule to the bank of molecules and assigning the molecule to an index of a closest molecule in the bank of molecules, wherein molecules assigned to the same index have similar sequences, structures, or properties.

In some embodiments, the method further includes feature extraction with layer-wise embedding, wherein, for multiple datasets or multiple parts of a dataset, features of each of the multiple datasets or each of the multiple parts of the dataset are extracted separately.

In some embodiments, the features can be plotted as layers of visualization on top of each other.

In some embodiments, the method further includes providing the map user interface comprising the visualization of the dataset with control inputs to enable viewing of the layers separately or in relation to other layers.

In some embodiments, one or more layers are used for training for the feature extraction, and one or more other layers are used for testing the feature extraction.

In some embodiments, the feature extraction comprises arranging embeddings in clusters.

In some embodiments, the feature extraction comprises embedding individual molecules.

In some embodiments, the feature extraction comprises generating clusters around molecules of interest.

In some embodiments, the feature extraction comprises sampling from the molecule map.

In some embodiments, the feature extraction comprises coding scores in the molecule map.

In some embodiments, the map user interface comprises a visualization of extracted features of the dataset.

In some embodiments, the method further includes using an user device to display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the method further includes using the map user interface to provide a visualization of clusters around molecules of interest.

In some embodiments, the map user interface comprises one or more clusters of molecules.

In some embodiments, the method further includes performing feature extraction for individual molecules of the dataset to obtain individual molecule embeddings.

In some embodiments, the layer-wise embedding comprises individual molecule embeddings.

In some embodiments, the method further includes using the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the method further includes modifying the amino acid sequence and wherein the system predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the method further includes using the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, or chimeric antibody.

In some embodiments, the method further includes concatenating features of parts of a molecule together to have a total feature for the molecule.

In some embodiments, the encoded sequence of information refers to an encoded amino acid sequence.

In some embodiments, the method further includes outputting a selected molecule.

According to an aspect, there is provided a manufacture obtained by the selected molecule output of the computer-implemented method described herein.

According to an aspect, there is provided a product obtained by the computer-implemented method described herein.

In some embodiments, the method comprises a step of producing a molecule identified or selected from the map user interface.

According to an aspect, there is provided a product obtained by the computer-implemented method described herein.

In some embodiments, the product is an antibody or an antigen binding fragment thereof.

According to an aspect, there is provided a non-transitory computer-readable medium or media having stored thereon machine interpretable instructions which, when executed by a processing subsystem, cause the processing subsystem to perform a method for mapping molecules into visual interfaces and generating maps for interfaces. The method includes receiving data for a set or multiple sets of one or more input molecules, wherein the input molecules are a set or multiple sets of one or more molecules, wherein the data comprises features of the molecules; generating at least one dataset by processing the data for the set or multiple sets of the one or more input molecules, wherein the dataset comprises encoded sequences of information, coordinates for each molecule to define structure of the molecule, features and fingerprints; transforming one or more of the data and the at least one dataset to generate a map and additional features by feature extraction, feature selection, or fingerprint generation to reduce higher dimensional data representations into lower dimensional data representations that can be indicated by the interface while capturing valuable information in the lower-dimensional data representations, the lower dimensional data representations comprising one or more clusters of the input molecules or newly generated molecules; generating a map user interface comprising the map as a representation of the lower dimensional data representations of the dataset, the representation representing the at least one dataset as one or more layers of molecules, each layer comprising one or more of the one or more clusters of molecules; and providing the map user interface.

According to an aspect, there is provided a computer-implemented system for an interface relating to molecules. The system including: a processing subsystem that includes one or more processors and one or more memories coupled with the one or more processors, the processing subsystem configured to cause the system to: receive input molecules, wherein the input molecules are a set or multiple sets of one or more molecules, wherein each molecule is defined as a sequence of information; encode the sequence of information; generate a dataset by processing the input molecules, wherein the dataset comprises the encoded sequence of information, three-dimensional coordinates of the sequence of information for each molecule to define structure of the molecule, the features and the fingerprints; transform the dataset by feature extraction and fingerprint generation to reduce a higher number of dimensions into lower dimensional data representations that can be indicated by the interface while capturing valuable data in the lower-dimensional data representations; generate one or more metrics from the transformed dataset, wherein the one or more metrics comprise lower dimensional data representations of the dataset and summarize characteristics of the input molecules; and provide the one or more metrics to an interface.

According to an aspect, there is provided a computer-implemented system for a visual interface for mapping molecules. The system includes a processing subsystem that includes one or more processors and one or more memories coupled with the one or more processors, the processing subsystem providing a map user interface, wherein the map user interface: receives input molecules, wherein the input molecules are a set or multiple sets of one or more molecules, wherein each molecule is defined as a sequence of information; and provides a map interface comprising a molecule map as a representation of lower dimensional data representations of a dataset for the input molecules, wherein the dataset comprises the sequence of information for each molecule, three-dimensional coordinates of the sequence of information for each molecule to define structure of the molecule, and features; wherein the molecule map comprises a transformation of the dataset by feature extraction and fingerprint generation to reduce a higher number of dimensions into lower dimensional data representations that can be indicated by the interface while capturing valuable data in the lower-dimensional data representations.

In some embodiments, the input molecules are proteins or protein-like molecules comprising antibodies and antigens.

In some embodiments, the antibodies comprise antibodies of a species including, but not limited to, mice, bovine, rabbits, camels, llamas, humans, alpaca, and standard species.

In some embodiments, the input molecules are antibodies and antigens, and wherein the molecule map is a paratope map.

In some embodiments, the input molecules are antigens, and wherein the molecule map is an epitope map.

In some embodiments, the map user interface comprises layer-wise embedding providing layers for the map visualization.

In some embodiments, the map user interface plots features as layers of the map visualization on top of each other.

In some embodiments, the map user interface has control inputs to enable viewing of the layers separately or in relation to other layers.

In some embodiments, the map user interface has control inputs to add or remove a layer of the layers for the map visualization.

In some embodiments, the map user interface comprises a visualization of extracted features of the dataset.

In some embodiments, the map user interface receives one or more reference molecules or target molecules, wherein the transformation of the dataset is based on the one or more reference molecules or target molecules.

In some embodiments, the map user interface receives one or more scores for the molecules, wherein the scores comprise expressibility scores and fuzzy panning scores.

In some embodiments, the map visualization comprises one or more clusters corresponding to the molecules, wherein the map user interface receives cluster control commands to update the map visualization with hyperparameters of the one or more clusters.

In some embodiments, the map visualization displays one or more scores in relation to the molecules, the scores comprising expressibility scores or fuzzy panning scores.

In some embodiments, the map user interface receives a control commands for sampling from at least a portion of the map visualization.

In some embodiments, the map user interface receives a control commands for editing samples drawn from at least a portion of the map visualization.

In some embodiments, the map user interface receives plot settings corresponding to visualization characteristics for the map visualization.

In some embodiments, the system further includes a user device to display the map user interface.

In some embodiments, the map user interface is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface comprises a visualization of clusters around molecules of interest.

In some embodiments, the map user interface comprises one or more clusters of molecules.

In some embodiments, the map user interface comprises individual molecule embeddings.

In some embodiments, the layer-wise embedding comprises individual molecule embeddings.

In some embodiments, the map user interface receives scores.

In some embodiments, the map user interface exports files.

In some embodiments, the map user interface comprises one or more buttons for adding or removing layers, one or more buttons for receiving input molecules, one or more buttons for adding or removing individual molecules, and one or more buttons for importing scores.

In some embodiments, the map user interface comprises a plurality of settings selected from the group of navigational settings for the map visualization, plot settings, settings for coding scores in the map visualization, cluster settings, settings for editing samples, sample settings, report settings, map analysis settings, and export settings.

In some embodiments, the processing subsystem causes the system to selectively subtract an unimmunized library of molecules from an immunized library of molecules to filter out nonspecific molecules and to reduce search space for sampling and searching for specific drug-candidate molecules for one or multiple targets; if multiple layers or datasets exist for the immunized library, the subsystem causes the system to selectively intersect the layers after subtraction to further reduce the search space.

In some embodiments, the processing subsystem causes the system to selectively subtract libraries of molecules immunized against one or multiple targets from a library of molecules immunized against a target of interest, to filter out molecules which are non-binders to the target of interest, and to reduce search space for sampling and searching for specific drug-candidate molecules for a target of interest; if multiple layers or datasets exist for the library of molecules immunized against the target of interest, the subsystem causes the system to selectively intersect the layers after subtraction to further reduce the search space.

Many further features and combinations thereof concerning embodiments described herein will appear to those skilled in the art following a reading of the instant disclosure.

DESCRIPTION OF THE FIGURES

The patent or application file contains at least one drawing executed in color. Copies of this patent or patent application publication with color drawing(s) will be provided by the Office upon request and payment of the necessary fee.

In the figures.

Figure 1:
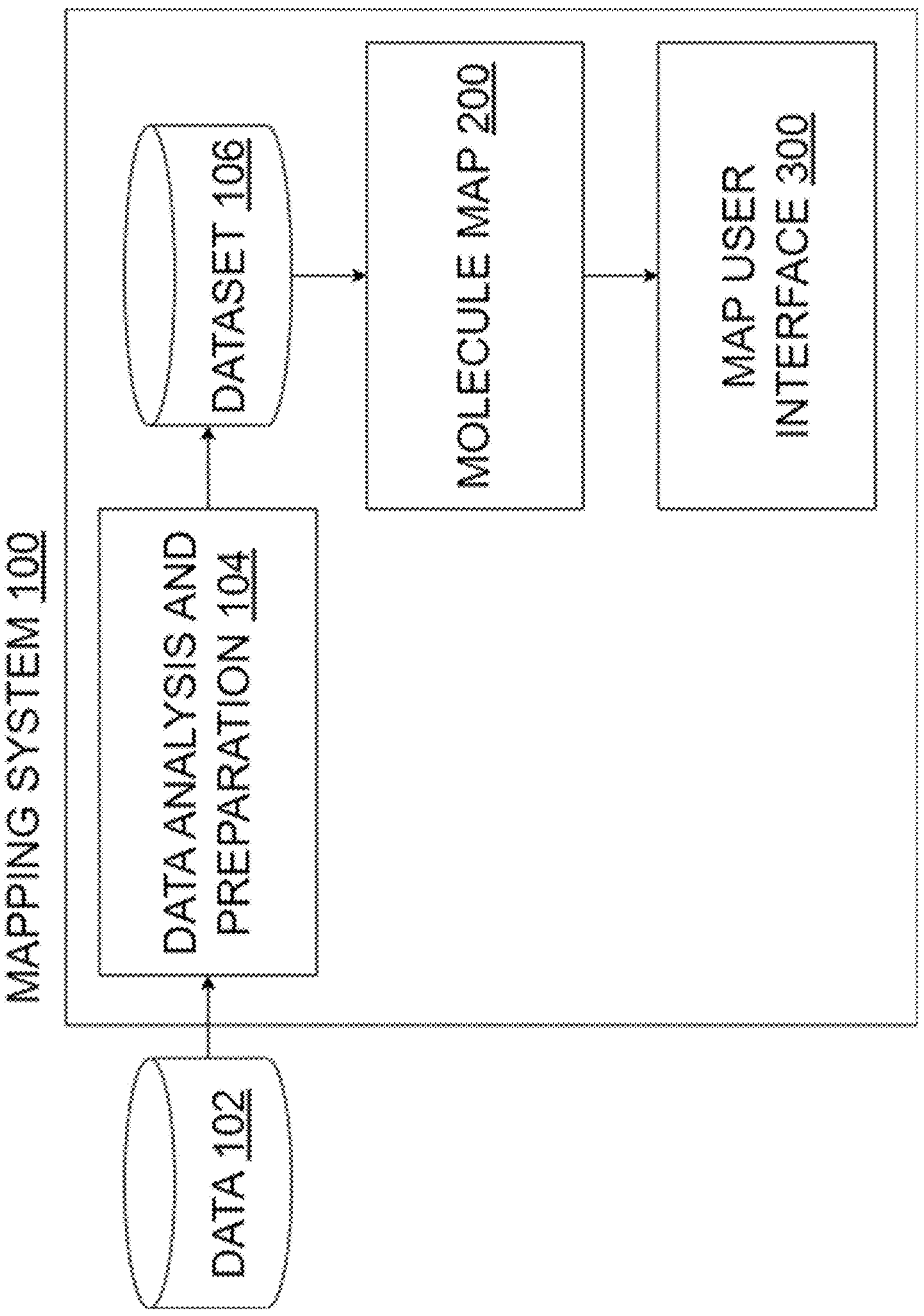
FIG. 1 is a block diagram of an example mapping system, in accordance with an embodiment.

These drawings depict exemplary embodiments for illustrative purposes, and variations, alternative configurations, alternative components and modifications may be made to these exemplary embodiments.

DETAILED DESCRIPTION

The systems and methods of the present disclosure can provide one or more maps. For example, the systems and methods of the present disclosure may provide a visual map representing antibodies of a library of antibodies and an interface comprising tools for interaction with the map for inspection, searching, sampling, clustering, and analysis of the antibodies. Advantageously, the map may represent, for example, substantially all and/or each antibodies of the library of antibodies (e.g., sequenced by next generation sequencing (NGS) or other sequencing platforms). In some embodiments, the systems and methods of the present disclosure may also compare different antibody libraries, for example, obtained for different targets or different immunization procedures (by layers subtraction and/or map subtraction, layer superimposition and/or map superimposition) to characterize all and/or each antibody (e.g., for their specificity, representativity or for other parameters determined by the user).

Advantageously, the systems and methods of the present disclosure may be used to identify antibodies having desired properties. In some embodiments, selection of antibodies for a given target may be driven by sequence and in some implementations, it may be driven by its structure or properties or function rather than by its sequence.

In some embodiments, data on regulatory approved antibodies may be integrated in the system of the present disclosure for comparison purposes. Therefore, in some embodiments, the systems and methods of the present disclosure may also be used to discover alternatives (e.g., biosimilars, subsequent biologics, follow-on biologics) to regulatory approved antibodies.

Moreover, the systems and methods of the present disclosure may also be used to identify antibody mimetics or artificial antibodies that have properties similar to those of a given antibody. In some embodiments, the alternative antibodies, antibody mimetics or artificial antibodies may be suggested or designed by the system or may come from antibody libraries.

In some embodiments, the systems and methods of the present disclosure may also be used to determine the extent, nature and/or robustness of an immune response against one or more antigens.

In some embodiments, the proteins or protein-like molecules can encompass antigens or fragments thereof. Accordingly, the systems and methods of the present disclosure can be performed to characterize epitopes or domains of antigens. For example, the systems and methods of the present disclosure may be used to identify immunodominant epitopes, hidden epitopes, dimerization or multimerization domains, active sites and the like. Advantageously, the systems and methods of the present disclosure may be used to identify epitopes or domains for which no antibody is available to provide new antibody candidates for purposes such as therapy or diagnostic.

In some embodiments, the systems and methods of the present disclosure may be used to characterize interactions between biomolecules (e.g., protein-protein interaction, proteins-DNA interaction, protein-RNA, etc.). In some embodiments the systems and methods of the present disclosure may be useful to characterize interactions between proteins of signaling pathways or cascades, receptor/ligands and the like. Therefore, in some embodiments, protein maps can provide insights into the structure, function, and interactions of proteins, which can be crucial for understanding biological processes and disease mechanisms.

Other exemplary embodiments of molecules can encompass small molecules (e.g., small molecule drug). Accordingly, the systems and methods of the present disclosure can be used to discover small molecule drugs (e.g., from de novo synthesis, from in vivo or in vivo analysis, from existing libraries or generated by artificial intelligence) that interact with one or more target of interest.

Other exemplary embodiments of molecules include nucleic acid molecules (RNA (mRNA), DNA, etc.).

In some embodiments, fragments may play a role in drug interactions by, for example, influencing how drugs interact with their biological targets and how they are processed in the body. For example, fragments may contain functional groups that interact with specific sites on biological targets, such as proteins or enzymes. Exemplary embodiments of fragments include, without limitations, antigen binding fragments, paratope, epitope, domains, peptides and the like.

In some embodiments, the input molecules are or include proteins, protein-like molecules or fragments thereof, small molecules or biomolecules such as nucleic acids, complex sugars, lipids, or combination of any of the preceding. Exemplary molecules include protein, protein-like molecules or fragments thereof.

In some embodiments, the proteins or protein-like molecules encompass antibodies or fragments thereof. Accordingly, the systems and methods of the present disclosure can be performed to identify antibodies (e.g., from immunized animals or humans, from existing libraries, or generated by artificial intelligence) that interact with one or more targets of interest. Therefore, the systems and methods of the present disclosure may be useful in the identification of therapeutically active antibody candidates.

Exemplary embodiments of antibody fragments include without limitations, antigen binding fragments, or antigen binding domains (e.g., paratope, one or more CDRs and/or framework regions, variable regions as described in more details herein).

Exemplary embodiments of antigen fragments include without limitations, domains, active sites, epitopes (linear or non-linear) or the like.

Newly generated data integrated in the system may become part of a master interface that may encompass information on private or publicly available molecules (e.g., antibodies), including, but not limited to regulatory approved molecules (e.g., regulatory approved antibodies), molecules involved in pre-clinical and clinical trials, and on previously generated data. Newly generated data can include, for example, lab data, saved data, data generated using a generative AI model (e.g., RFDiffusion; a generative model for proteins).

A user can interrogate the system and compare data by intersection, subtraction and/or superposition with data of the master interface.

FIG. 1 shows an example pipeline of a system 100 for mapping molecules into visual interfaces. The data 102, which is provided as input to the system 100, can be information on about a molecule, a set of molecules or multiple sets of any molecules. In some embodiments, reference and target molecules are provided as input in 102. The reference and target molecules be the basis of a map. System 100 can involve different types of input molecules. For example, the input molecules can be proteins, or any protein-like molecules, including, but not limited to, antibodies, antigens, lectins, and receptors.

The term "antibody" encompasses various antibody formats and structures, including any immunoglobulin, monoclonal antibody, polyclonal antibody, bivalent antibody, monovalent antibody, bispecific antibody, multiple specific (multi-specific) antibody, conventional or native antibody (e.g., made of light chains and heavy chains), single domain antibody, single chain antibody (e.g., single chain variable fragment, scFv), heavy chain only antibody, nanobody, humanized antibody, chimeric antibody, artificial antibody, antibody mimetics, any antigen binding fragment that exhibits the desired antigen binding activity and any variants of an antibody. An antibody can be produced upon immunization of an animal, including transgenic animals, such as for example, any animal species including without limitations, mice, cows (bovine), rabbits, camels, llamas, humans, alpaca. Antibodies may be produced recombinantly and may also be chemically synthesized.

In the context of antibodies, "binding" refers to the interaction between an antibody and an antigen. The binding of an antibody to its target is preferably specific so as to avoid off-target side effect.

In some embodiments, a chimeric antibody or antigen binding fragment thereof, encompasses, without limitations an antibody or antigen binding fragment thereof that comprises a variable region from one species and a constant region from another species. Typically, a chimeric antibody or antigen binding fragment thereof may comprise variable regions (or a portion thereof) derived from a non-human antibody (e.g., mouse, rat, rabbit, hamster etc.) and a constant region of a human antibody or a portion thereof (e.g., human Fc, human CH3 or human CH2-CH3 domain).

In some embodiments, a humanized antibody or antigen binding fragment thereof, encompasses, without limitations an antibody or antigen binding fragment thereof in which amino acid residues are replaced to increase sequence similarity or sequence identity with a human antibody or human antibody consensus (e.g., germline template). Typically, a non-human antibody is humanized by replacing one or more amino acid residues in one or more framework regions with the corresponding amino acid residues of the most similar or most identical human antibody or human antibody consensus. An antibody or antigen binding fragment thereof may be considered fully humanized if the amino acid residues of the framework region are 100% identical to those of a human antibody or a human antibody consensus or partially humanized if the amino acid residues of the framework region are less than 100% identical to those of a human antibody or a human antibody consensus. A humanized antibody or antigen binding fragment thereof may also comprise CDR amino acid residues of a human antibody. Typically, a humanized antibody or antigen binding fragment thereof (either fully humanized or partially humanized) may also comprise a constant region of a human antibody or a portion thereof (e.g., human Fc, human CH3 or human CH2-CH3 domain).

Exemplary embodiments of artificial antibodies include antibodies generated in silico or by machine learning-based methods such as generative artificial intelligence.

Antibody mimetics are generally derived, for example, from non-antibody scaffold proteins. Exemplary embodiments of antibody mimetics encompass without limitations, affibody, adnectins, affilins, affimers, affitins, alphabodies, anticalins, aptamers, armadillo repeat proteins, atrimers, avimers, Designed Ankyrin Repeats (DARPins), fynomers, Kunitz domain peptides, knottins and the like (see Yu, X. et al., Annu Rev Anal Chem, 10 (1): 293-320, 2017 the entire content of which is incorporated herein by reference). Antibody mimetics encompass any types of molecules that have the ability to interact or bind to an antigen. Antibody mimetics may specifically interact with an antigen by a complementary shape (paratope) with an antigen epitope.

Other exemplary antibody formats and structures include without limitations single chain Fv-CH3 (scFv-CH3) fusion, tandem-scFv-CH3 (TaFv-CH3) fusion, diabody-CH3 (Db-CH3) fusion, tandem Db-CH3 (TaDb-CH3) fusion, single chain Db-CH3 fusion (scDb-CH3), Fab-CH3 fusion, single chain Fab-CH3 fusion, Fab-scFv-CH3 fusion, dual affinity retargeting (DART)-CH3 fusion, Fab-DART-CH3 fusion, single chain Fv-Fc (scFv-Fc) fusion, tandem-scFv-Fc (TaFv-Fc) fusion, diabody-Fc (Db-Fc) fusion, tandem Db-Fc (TaDb-Fc) fusion, single chain Db-Fc fusion (scDb-Fc), Fab-Fc fusion, single chain Fab-Fc fusion, Fab-scFv-Fc fusion, dual affinity retargeting (DART)-Fc fusion, Fab-DART-Fc fusion etc.

Some examples of antibody-like proteins include, for example and without limitation, VH-VL, VHH, ScFv (single-chain variable fragment), Fab, HCAb, IgNAR, etc. The input molecules can be antibodies of any species including, but not limited to, mice, cows (bovine), rabbits, camels, llamas, humans, alpaca, and standard species. The input molecules can be from any source, e.g., they can be natural, synthetic, generated in transgenic animals, in-silico generated, etc. In some implementations, antigens can be used as data, either along with antibodies or stand alone. The system 100 accepts any molecule in general. If it is used for antibodies and antigens, the generated map can be named a paratope map and an epitope map, respectively. The data 102 can be information about a molecule including a sequence of information (e.g. for antibodies the sequence of information can include the complementarity-determining regions) and can also include different characteristics of the molecule (activity, expressibility, affinity, etc.).

Exemplary embodiments of a single domain antibody include an antibody produced by camelids (dromedaries, camels, llamas, alpacas, etc.) or by shark. In some instances, a "single domain antibody" may be produced from transgenic animals that are modified to express heavy chain only antibodies. Exemplary embodiments of transgenic animals are provided in international application No. PCT/CA2021/050951 filed on Jul. 21, 2021, and published on Jan. 20, 2022, under No. WO2022/011457, the entire content of which is incorporated herein by reference.

Exemplary embodiments of antigen binding fragment(s) include a fragment of the antibody that encompasses the antigen binding domain and that may incorporate or not, other portion(s) of the antibody such as for example amino acid residues of the hinge region, amino acid residues of a constant region, portion of a Fc region. Regardless of structure, an antigen binding fragment usually binds to the same antigen that is recognized by the complete antibody.

Exemplary embodiments of an antigen binding domain include a portion of an antibody that is involved in antigen binding and comprises for example, one or more complementarity determining regions (CDRs,) one or more framework regions (FR) or the entire variable region(s). An exemplary embodiment of an antigen binding domain in the context of a single domain antibody thereof may include the portion of single domain antibody that is involved in antigen binding such as, for example, one or more of CDRs selected from CDRH1, CDRH2 or CDRH3, one or more framework regions FR1, FR2, FR3, FR4 or the entire variable region (VH or VHH). The term "antigen binding domain" in the context of a native antibody thereof relates to the portion of a native antibody that is involved in antigen binding and comprises for example, one or more CDRs selected from CDRH1, CDRH2, CDRH3, CDRL1, CDRL2 or CDRL3, one or more light chain or heavy chain framework regions FR1, FR2, FR3, FR4 or one or both entire variable regions (heavy chain variable region (VH) and/or light chain variable region (VL)). Another embodiment of an antigen binding domain is a paratope.

As used herein the terms "CDRH1", "CDRH2" and "CDRH3" respectively refer to the CDR1, CDR2 or CDR3 of an antibody heavy chain. As used herein the terms "CDRL1", "CDRL2" and "CDRL3" respectively refer to the CDR1, CDR2 or CDR3 of an antibody light chain. It is to be understood herein that the location of "CDR" in a conventional antibody may be determined with the Kabat numbering scheme (e.g., Kabat, J Immunol., 147:1709-19 (1991); Chothia C, Lesk AM, J Mol Biol. August 20; 196 (4): 901-17 (1987)), Chotia numbering scheme or IMGT numbering scheme (e.g., Lefranc, M.-P., The Immunologist, 7, 132-136 (1999)).

In some embodiments, the affinity of an antibody or antigen binding fragment thereof may be determined by the strength of non-covalent interaction between a binding agent or antigen binding domain(s) thereof and an antigen.

In some embodiments, an epitope encompasses, for example and without limitations, a specific group of atoms or amino acid residues on an antigen to which an antibody or an antigen binding fragment bind. Two antibodies may bind the same or a closely related epitope within an antigen if they exhibit competitive binding for the antigen. An epitope can be linear or conformational (i.e., including amino acid residues spaced apart). For example, if an antibody or antigen binding fragment blocks binding of a reference antibody to the antigen by at least 85%, or at least 90%, or at least 95%, then the antibody or antigen-binding fragment may be considered to bind the same/closely related epitope as the reference antibody. Two antibodies may be considered to bind the same or a closely related epitope if they cluster together on a paratope map.

In some embodiments a paratope encompasses, for example and without limitations, a spatial structure resulting from the specific group of atoms or amino acid residues on an antibody or an antigen binding fragment that binds an antigen. Typically, a paratope correspond, for example, to the part of an antibody that binds to a specific portion of an antigen, forming an antigen-antibody complex. For example, a paratope of a given antibody may be structurally similar or identical to a paratope of another antibody without sharing significant amino acid identity.

As used herein, the term "identity" with respect to a sequence indicates the degree of identity between two or more nucleic acid sequence or two or more amino acid sequences when best compared. The sequence identity can be at least 85%, 90% or 95%, preferably at least 95%. Non-limiting examples include 85%, 86%, 87%, 88%, 89%, 90%, 91%, 92%, 93%, 94%, 95%, 95%, 96%, 97%, 98%, 99%, and 100%. Generally, the identity is determined over the entire length of the shorter sequence. However, in some instances, identity may be determined over a portion of the sequence.

The term "similarity" with respect to a sequence takes into account the degree of sequence identity as well as the degree or amino acid residues that are replaced with conservative amino acid substitution. The term similarity as used herein can refer to different types of similarity measures. Similarity can be in terms of sequence, structure (three-dimensional coordinates), biophysical properties (charge, hydrophobicity, stability (e.g., thermal stability, pH stability, resistance to proteolysis), solubility, aggregation propensity, affinity, avidity, specificity, immunogenicity risk, glycosylation, post-translational modifications), expressibility, potency, and/or manufacturing characteristics (e.g., yield). Accordingly, sequence similarity and paratope similarity are (non-limiting) examples of structure similarity.

Generally, the degree of sequence similarity and identity between sequences is determined using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Variants of the present disclosure may therefore comprise a sequence that is at least 50%, 55%, 60%, 65% 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% identical to a reference sequence or a portion of a reference sequence.

In some embodiments, paratope similarity may be determined, for example and without limitations, by the degree of resemblance or likeness between the spatial arrangements of atoms in the three-dimensional space of two or more paratope structures. In exemplary embodiments, comparison of protein structures (e.g., paratope structure) may be performed by superimposing one structure onto another to assess the overlap of atoms. In some embodiments, methods such as root-mean-square deviation (RMSD) may be used to quantify the structural differences between two protein structures.

In some embodiments, the structure can include coordinates of atoms or molecules of the proteins, protein-like molecules or fragments thereof. The structure can also be visualized in ribbon or surface ways. The structure may also be a snapshot of a sculpture of the protein or protein-like molecule. The structure may be provided by way of 3D visualization. The structure may also be provided by the exposure (e.g., solvent exposure).

In some embodiments, the "expressibility" in the context of an antibody or antigen binding fragment thereof may be determined, for example and without limitations, by the ability of a host organism, such as a mammalian cell, to produce and/or secrete antibodies that have the desired binding and/or function activity.

In some embodiments, the stability of an antibody may be determined, for example and without limitations, by maintenance of its structural integrity, functionality, and/or biochemical properties over time and/or under various conditions.

In some embodiments immunogenicity may be determined, for example and without limitations, by the ability of a substance, such as a protein, to induce an immune response in an organism. In the context of proteins, including therapeutic proteins and biologics, immunogenicity encompasses, for example, the potential of the protein to provoke an immune reaction in the body, such as production of antibodies (or cells able to express antibodies) against that protein.

Exemplary embodiments, of protein-like molecules include, without limitations, peptidomimetics and any molecules that comprises at least a polypeptidic portion such as for example, and without limitations, protein-polymer conjugates, protein-nucleic acid hybrids (aptamers. Peptide nucleic acids (PNAs)), protein-lipid hybrids.

As used herein, "fragment" can refer to a part of a larger molecule. A fragment of a molecule may be continuous or non-continuous. In some embodiments, an epitope (linear or non-linear) may be referred as a fragment of an antigen. In some embodiments, a paratope may be referred as a fragment of an antibody. In some embodiments, fragments can play a role in drug interactions by influencing how drugs interact with their biological targets and how they are processed in the body. For example, fragments may contain functional groups that interact with specific sites on biological targets, such as proteins or enzymes. Exemplary embodiments of fragments include, without limitations, antigen binding fragments, paratope, epitope, domains, peptides and the like. Exemplary embodiments of antibody fragments include without limitations, antigen binding fragments, or antigen binding domains (e.g., paratope, one or more CDRs and/or framework regions, variable regions as described in more details herein).

Input data can include data relating to sequence, structure, and/or biophysical properties of molecules. As used herein, "sequence" refers to the specific order in which amino acids are arranged in a polypeptide or protein. This sequence can be determined by the genetic code and can dictate the protein's structure and function. For example, the linear sequence of amino acids in a protein, linked by peptide bonds. This sequence is unique for each protein and determines how the protein will fold and function. The structure of a protein or molecule can be described at several levels including the primary structure (e.g., the linear sequence of amino acids), the secondary structure (e.g., localized folding patterns within the protein, such as alpha-helices and beta-sheets, stabilized by hydrogen bonds, etc.), the tertiary structure (e.g., the overall three-dimensional shape of a single polypeptide chain, formed by interactions between the side chains (R groups) of the amino acids), the quaternary structure (e.g., the arrangement of multiple polypeptide chains (subunits) in a multi-subunit protein).

As used herein, "biophysical properties" refer to the physical and/or chemical characteristics of molecules or proteins. Biophysical properties may influence the behavior and interactions of molecules or proteins. Examples include molecular weight, hydrophobicity and hydrophilicity, binding affinity, avidity, specificity, thermal stability, pH stability, resistance to proteolysis, isoelectric point, solubility, aggregation propensity, immunogenicity risk, glycosylation, and/or post-translational modifications.

As used herein, a "map" refers to a representation of a space that associates molecules within the space according to one or more models or clusters. An example map can indicate spatial distributions of molecules. Specific example types of maps referred to herein include epitope maps, paratope maps, protein maps, etc.

As used herein, an "epitope map" can be a detailed representation of the specific regions (epitopes) on an antigen that are recognized and bound by antibodies. In some embodiments, the map can identify the binding sites of antibodies on antigens, which may help to determine the mechanism of action of antibodies and their potential therapeutic uses.

As used herein, a "paratope map" can be a detailed representation of the specific regions (paratopes) on an antibody that bind to an antigen.

As used herein, a "protein map" can be a comprehensive representation of the proteins expressed in a particular organism, tissue, or cell type.

As used herein, "cluster" refers to a group of proteins, protein-like molecules, or fragments thereof (and related data elements) that are "similar" to each other within a dataset. Clustering is a technique to organize data points into meaningful groups based on characteristics.

The format of data files 102 can be different formats. The data 102 can be from different sources. In some implementations, data can include sequence and/or structure information obtained from NGS (next-generation sequencing), hybridoma, or single B cell sorting. For example, Protein Data Bank (PDB) files or FASTA format can be used for proteins, antibodies, and antigens. The PDB format contains the information of structure and sequence of proteins while the FASTA format includes the sequence of information of proteins.

The data files 102 can include molecules represented as sequences of information. For example, the system 100 can store sequence of information representing molecules in a database.

In some embodiments, each sequence of information for a molecule can be indexed by an identifier. Example identifiers and sequences of information are shown below:

| FID | SEQUENCE | SEQ ID NO |
|---|---|---|
| 1 | QVQLEESGGGLVQAGDSL TLSCVASGRTFSSYAMG | 1 |
| 2 | QVQLEESGGELVQAGGSL RLSCVASGLTSNRYNMG | 2 |
| 3 | QVQLEESGGELVQAGGSL RLSCVASGLTSNRYNMG | 3 |

The above sequences are examples only. These are framework 1 sequences for heavy chain antibodies. The sequences can be used by system 100 to identify antibody sequences during the NGS bioinformatic process, which may be referred to as NGS preprocessing.

Additionally, some or all parts of the data 102 can be in other formats such as spreadsheet file, data frames, Comma Separated Values (CSV) format, text files, hex files, tables, and visualizations of any format. Moreover, biophysical properties of all origins-high volume data, e.g., NGS, can be used as part of data 102. For example, every amino acid or residue in a protein or antibody can have biophysical properties. These properties include, but are not limited to, pH, hydrophobicity and hydrophilicity, negative and positive charges, and solvent exposure, i.e., how much the amino acid appears on surface of the antibody.

Parts of data 102 can also be obtained from sequencing methods of nucleic acids, such as PacBio, Illumina, and Nanopore. Some preparation and preprocessing steps, such as stop codons, amber codons, frameshifts, can also be utilized. The data 102 can also go under any transformations, e.g., matrix transformations, in a preprocessing stage. For example, there can be NGS preprocessing. As another example, preprocessing can involve taking out redundancy in data 102.

A dataset 106 can be generated out of data 102 through data analysis and preparation 104 in system 100. The three-dimensional coordinates of the atoms of every molecule can be considered as part of the features of the dataset. For example, if the molecules are proteins, the three-dimensional coordinates of the atoms of amino acids can be extracted out of the PDB files. In some implementations, it is possible to use the average of the coordinates of atoms in every amino acid, to have an average three-dimensional coordinate per amino acid in the protein. The three-dimensional coordinates of the atoms or the amino acids contain the information of structure of the molecule. System 100 can use generative models for dataset 106 in some embodiments.

System 100 can generate dataset 106 out of data 102 through data analysis and preparation 104. This can involve training data and pre-processing the data for the training. For example, system 100 can use a precision pipeline for handling NGS data. This data can be pre-processed before training and at step 104 system 100 can prepare the data for training. The sequences obtained by system 100 from NGS data. System 100 can pre-process the NGS data to get to the paratope map, for example.

System 100 can implement an NGS pipeline for preprocessing data. Paired-end DNA sequencing reads of nucleotide sequences are aligned. The nucleotide sequences are analysed to identify open reading frames coding for proteins and the amino acid sequences are determined. The amino acid sequences are then filtered for proteins that match the profile of an antibody. A list of unique antibody sequences with prevalence data can then be saved.

A molecule can be considered as a sequence of information. For example, if the molecule is a protein, it is a sequence of amino acids. The sequence of information can also be used for dataset generation. Any encoding method, such as one-hot encoding, binary encoding, index encoding, or Gray code, can be used to encode the sequence of information.

The extracted features from the data 102 can be put together to prepare the dataset 106. The raw dataset 106 can includes features. As will be described herein in relation to FIG. 2, the dataset 106 also undergoes feature extraction at 202 to generate the map. Accordingly, there can be features in dataset 106 and also feature extraction during the map generation.

For example, the sequence of information encoding, three-dimensional coordinates of the sequence, and some other properties—such as the properties including solvent exposure, hydrophobicity, and charge—can be used as the features of dataset 106.

Figure 9:
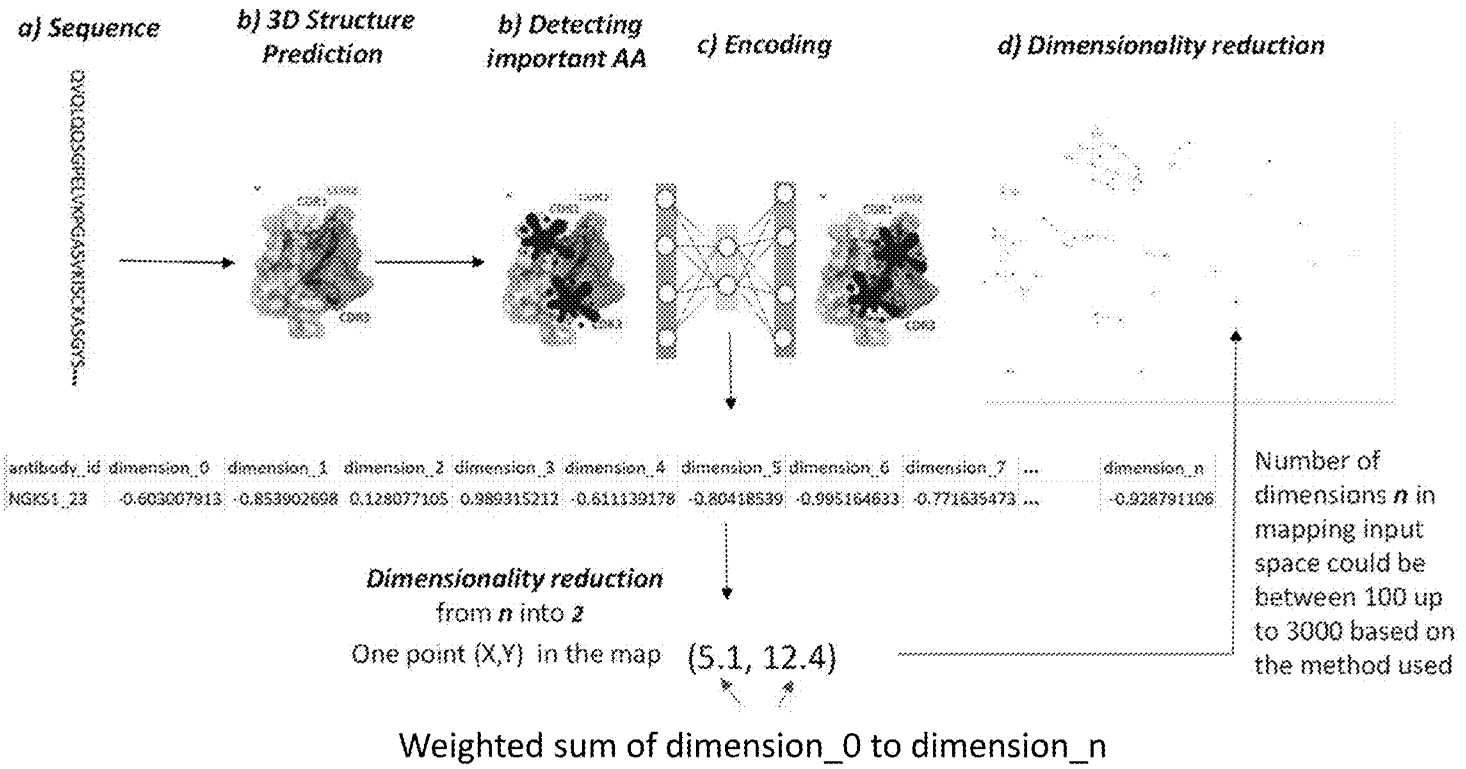
FIG. 9 is a schematic diagram of an example representation of antibodies in a paratope map.
Figure 10:
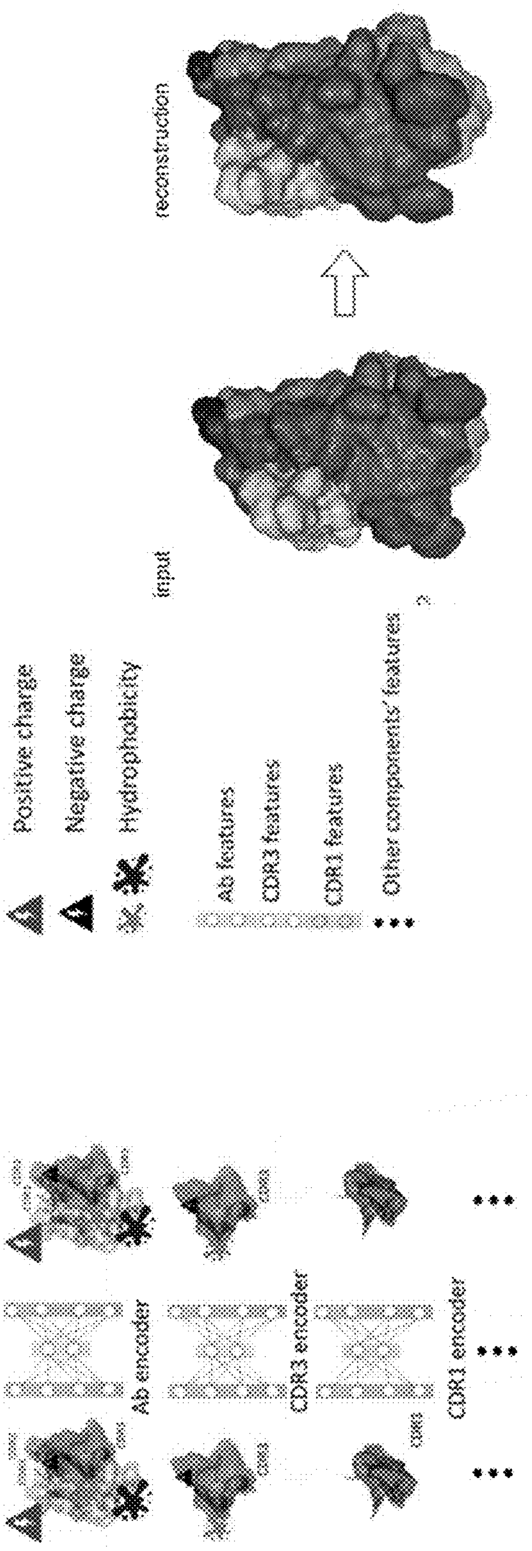
FIG. 10 is an example schematic diagram of data processing showing features of parts of antibody concatenated together to have a total feature for the antibody.

FIG. 9 and FIG. 10 are example schematic diagrams of data processing according to example embodiments. FIG. 9 is a schematic diagram of an example representation of antibodies in a paratope map. FIG. 10 is an example diagram showing features of parts of antibody concatenated together to have a total feature for the antibody. System 100 can implement different data transformation, and system 100 can also reconstruct each part and transformation.

In some implementations, it is possible to consider features per parts of molecules. For example, if the molecule is a VHH antibody, it has multiple parts, namely framework 1, CDR1, framework 2, CDR2, framework 3, CDR3, and framework 4, where each part contains several amino acids of the sequence. System 100 can get features for each part separately and then concatenate them. For example, the amino acid encoding, three-dimensional coordinates, solvent exposure, hydrophobicity, and charge of the amino acids of every part can be used to train and test a reconstruction autoencoder. Features of every part of antibody can be obtained in the latent space of the reconstruction autoencoder of that part. Then, the features of parts of antibody can be concatenated together to have the total feature for the antibody. System 100 can concatenate features to generate a feature vector. The parts have different weightings and system 100 can generate a weighted reconstruction. The features are separated for system 100 to generate the weighted reconstruction. The dataset 106 includes features and the features are then extracted at 202.

Another example of extracted features can be referred to as fingerprints, which can be extracted out of the above-mentioned raw dataset. Feature extraction can reduce the dimensionality of the dataset 106 which can help generate visualizations effectively. Feature extraction can involve extracting features that still capture the essential information from the original the dataset 106. A feature can be an individual measurable property or characteristic about one or more molecule(s). Features can also be referred to as parameters or variables and their associated values. There can be numerical features and categorical features, for example. A feature can be represented as a feature vector which is an n-dimensional vector of numerical features that represent as molecule property or characteristic. Fingerprinting is a process that maps a large data item to a shorter string or other value that can uniquely identify that original data. Features and fingerprints may support efficient use of resources as they can condense substantial blocks of data to efficiently use resources for computation and transmission for example. In biotechnology, features may be referred to as fingerprints. These terms can be used interchangeably for example embodiments. For the description herein, fingerprint is an example of a feature. Raw features can be processed using feature extraction to generate fingerprints.

Different machine learning or statistical methods can be used for feature extraction and fingerprint generation out of the raw dataset. Some examples are dimensionality reduction, reconstruction autoencoder, variational autoencoder, adversarial autoencoder, neural networks, graph neural networks, attention networks, recurrent networks, Molecular Surface Interaction Fingerprinting (MaSIF), etc.

In some implementations, it is possible to consider features per parts of molecules. For example, if the molecule is a VHH antibody, it has multiple parts, namely framework 1, CDR1, framework 2, CDR2, framework 3, CDR3, and framework 4, where each part contains several amino acids of the sequence. It is possible to get features for each part separately and then concatenate them. For example, the amino acid encoding, three-dimensional coordinates, solvent exposure, hydrophobicity, and charge of the amino acids of every part can be used to train and test a reconstruction autoencoder. Features of every part of antibody can be obtained in the latent space of the reconstruction autoencoder of that part. Then, the features of parts of antibody can be concatenated together to have the total feature for the antibody. This example procedure is depicted in FIG. 10 which is an example diagram showing features of parts of antibody concatenated together to have a total feature for the antibody. In some embodiments, the method involves concatenating features of parts of a molecule together to have a total feature for the molecule.

In some embodiments, system 100 can use dimensionality reduction to process the dataset. System 100 can use dimensionality reduction to reduce dimensions of the data (e.g., two dimensions) so that the data can be visualized while still capturing valuable data relationships in the visualization generated by the reduced dimension representation.

Additionally, it is also possible to use the available bank of molecules where every molecule is assigned a unique index. Then, any other molecule and the bank of molecules can be compared to each other, and every molecule can be assigned to the index of the closest or most similar molecule in the bank. In this way, the molecules with the same indices will have similar sequences, structures, or properties.

As shown in FIG. 1, in some embodiments, after the dataset 106 is prepared, it is fed as input to the molecule map 200. In some embodiments, the dataset 106 can be transformed into one or more metrics about the molecules. The molecule map 200 transforms the dataset 106 into a map which can be analyzed, inspected, and may also be visualized at an interface. This transformation can be any linear or nonlinear transformation. A map can be defined as transformation of molecules to some features vectors, with some dimensionality, which can also be visualized or analyzed.

Figure 2:
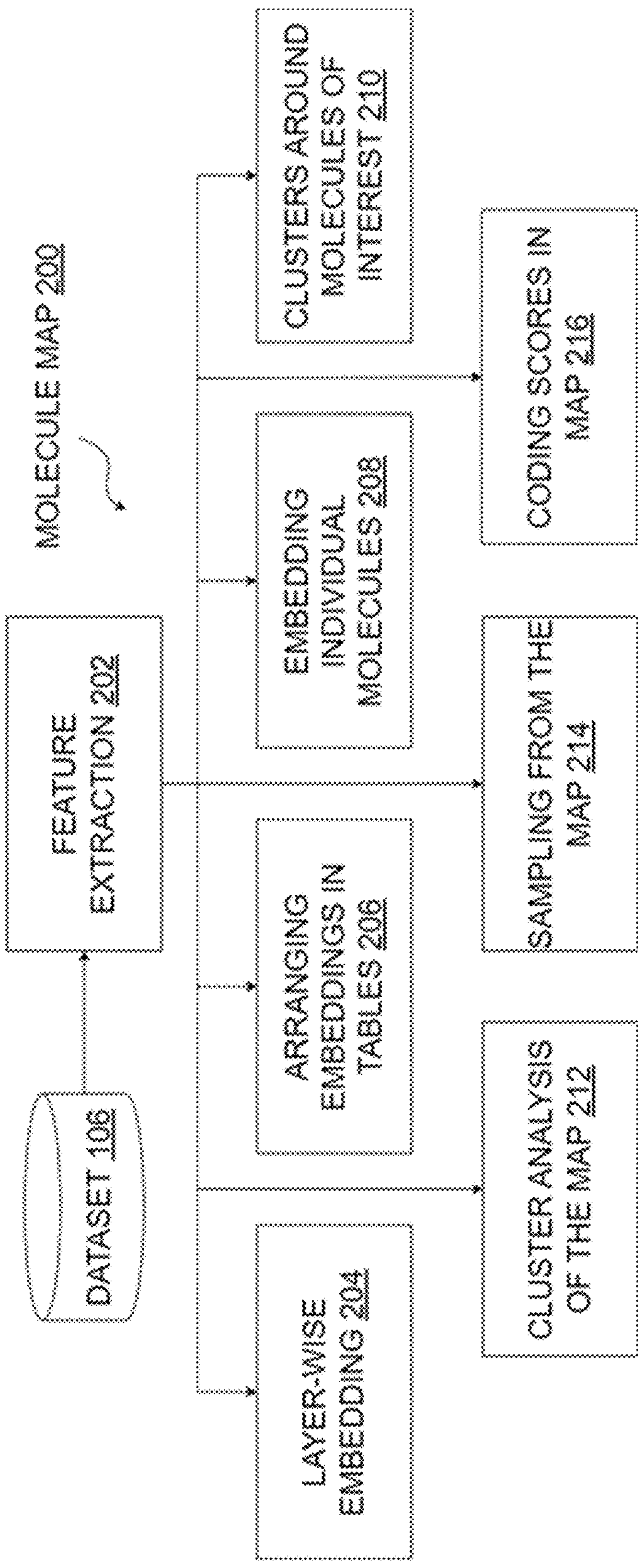
FIG. 2 is a block diagram of an example molecule map, in accordance with an embodiment.

An example of the molecule map 200 is depicted in FIG. 2. Feature extraction 202 is used to extract features out of the dataset 106. Feature extraction 202 can also be used to generate fingerprints from the dataset 106. Fingerprints are an example feature. Different methods, including but not limited to, statistical and machine learning methods, can be used for feature extraction and fingerprint generation. For example, dimensionality reduction or manifold learning algorithms can be used for feature extraction. In some implementations, UMAP, or t-SNE, or a neural network can be used for feature extraction. Any dimensionality reduction, feature extraction, or feature selection method can be used to reduce higher number of dimensions into lower dimensional data so that it can be visualized—while still capturing valuable data in the lower-dimensional representations. For example, the valuable information can embed similar instances in terms of patterns, labels, or features to be embedded close to each other and dissimilar instances in terms of patterns, labels, or features to be embedded away from each other. If a machine learning algorithm is used, the different types of machine learning algorithms—whether unsupervised, or supervised, or semi-supervised—can be used.

After the feature extraction, the features of dataset are obtained and can be used to inspect, analyze, and visualize. In some embodiments, this feature extraction can be performed layer-wise and can be called layer-wise embedding 202. In layer-wise embedding 202, there can be multiple datasets or multiple parts of a dataset where the features of every dataset or every part of dataset are extracted separately. If the features are going to be used for visualization (e.g. for visual elements of a user interface), for example, they can be plotted as layers of visualization on top of each other in a graphical representation. If the layer-wise embedding 202 is for inspection and analysis, the layers can be analyzed either separately or in relation to one another. One or several of the layers can be used for training in the feature extraction algorithm and the other layers can be used for the test (out-of-sample) phase in the algorithm.

The extracted features can be represented as a map which can be analyzed and visualized at a user interface displayed on a device. The map can be of any dimension. For example, the map can be one-dimensional, two-dimensional, three-dimensional, four-dimensional, or of higher dimensions. In some implementations, if the embeddings of the map change over time as a time-series, it can be three-dimensional embeddings changing over time, representing four-dimensional embeddings. That is, time can provide an additional dimensional embedding. Different combinations of any number of dimensions can also be captured and visualized as the map.

The embeddings can also be arranged in tables as clusters, as in step 206 in the molecule map 200. Tables can be stored and represented in any format, e.g., data frames, spreadsheet file, data frames, csv files, SQL files, tables, etc.

In addition to batches of molecules, feature extraction 202 can be applied to individual molecules to obtain individual molecule embeddings 208. These individual molecules can be considered as additional layers in the layer-wise embedding 202. The individual molecules embeddings 208 can be investigated, e.g., based on where they are located in the map compared to other molecules. For example, the individual molecules can be individual reference antibodies or possible target antibodies in a drug discovery application. In this example, an antibody of interest can be considered as the reference antibody, and it can be investigated where it is spatially located in the map compared to other antibodies or antigens.

It is possible to consider and analyze clusters around some molecules of interest (210). The cluster size around each molecule of interest can be either fixed or tunable and can be determined by the user. In the map, each cluster can be either centered at the molecule of interest or it can contain the molecule of interest, not necessarily centered at it. The cluster can be of any shape, e.g., sphere, square, rectangular, hyper-cube, hyper-sphere, etc. The purpose of clusters being around molecules of interest can be for different reasons. For example, a cluster around a molecule can be for filtering and analyzing the molecules similar to that molecule of interest. Another example is for sampling from or comparing the molecules close to the molecule of interest. In some implementations, the molecule of interest can be the target antibodies where the cluster around it is to filter, analyze, compare, and sample from the antibodies or antigens similar to it or complement to it. The similarity can be in terms of any characteristic such as sequence, structure, or biophysical properties (solvent exposure, hydrophobicity, charge, etc.). Similarity can be any measure of similarity such as inner product, kernel functions, cosine similarity, and negative distance or inverse of distance. Also, any distance metric can be used for measuring dissimilarity or similarity. For example, Euclidean distance, Mahalanobis distance, generalized Mahalanobis distance, and distance metric learning can be used. For example, system 100 can measure similarity based on how close molecules are in the map. This can be in terms sequence, structure and physical properties. The term similarity as used herein can refer to different types of similarity measures. Similarity can be in terms of sequence, structure (three-dimensional coordinates), biophysical properties (charge, hydrophobicity). Accordingly, sequence similarity and paratope similarity are (non-limiting) examples of structure similarity.

In some embodiments, the map contains one or multiple clusters, or clouds, of molecules depending on the embedding of the molecules. The clusters in the map can be analyzed and compared (212). The number of clusters can be determined to analyze the whole structure of the map. Determining the number of clusters is an ill-defined problem because one may see a cluster as two smaller clusters; however, the most natural number of clusters can be determined based on the consensus between (most) humans and the visualization of data points in the map. The reference to consensus between humans as used herein can mean what most humans would consider points in the map to be clusters. For example, most humans reviewing a visualization with multiple data points may see two clusters, but a few humans may see four clusters, a few other humans may see three clusters, etc. None of these are incorrect as there could be many data points on the map and the clusters can be interpreted differently by different humans. The consensus between most humans can be the number of clusters of the visualization. Any method can be used for determination of the cluster and the number of clusters. In some implementations, different clustering algorithms such as K-means, K-medoids, fuzzy C-means, DBSCAN, hierarchical clustering, etc., can be used for finding the clusters in the map. There can be different numbers of clusters. The number of clusters can be a tunable parameter, and there can be a default value as an initial setting. In some embodiments, the default number of clusters, which is the usual consensus between humans, can be a large island as one cluster. A tunable hyperparameter can be initially set to this default value and it can be changed by the user so that the number of clusters change to more or less number of clusters.

In the cluster analysis 212, it is possible to also analyze meta-clusters, i.e., clustering clusters so that similar clusters are closer together and dissimilar clusters are further apart.

It is also possible to use indexing on representative molecules for clustering and cluster analysis 212. A database of molecules can be used for indexing. The molecules which fall close to those molecules in the database (e.g., storing a databank of molecules), in the same cluster, can be assigned the same index. It is also possible to use the average or any summary statistics of all or some antibodies in the same cluster. The molecules in one or multiple databases of molecules can be indexed. Assume the number of molecules in the database(s) is n; then, the indices will be 1, 2, . . . , n. Then, every other molecule can be embedded to the same map as the database. In the embedding space, K-nearest neighbor (e.g., 1-nearest neighbor) can be used to assign an index to the molecule.

In some embodiments, the system 100 assigns each molecule in the databank an index. The system 100 can use the map to map both the database and their antibodies. The system 100 can assign an index to an antibody based on what antibody in the database is the closest, for example. For example, the databank can have n data points indexed 1 . . . n. If there is a new antibody then the system 100 can classify it to have an index based on what is the closet molecule in the databank.

In some embodiments, molecule map 200 is configured to sample from molecules in the map (214). This sampling can be from all different parts of the map or specific parts or clusters of the map. Different sampling techniques, e.g., simple random sampling, stratified sampling, cluster sampling, bootstrapping, etc., can be used. Sampling can either be with or without replacement. For example, stratified sampling can be performed to sample proportionally to the cluster sizes. In some implementations, clustering algorithms, such as K-means, can be used along with sampling to sample proportionally to the cluster sizes.

In sampling from the map (214), it is also possible to sample iteratively where samples can be drawn from different layers in the layer-wise embedding 202. Moreover, samples can be drawn from particular parts of the map. For example, samples can be drawn within the clusters around particular molecules in the map. In some implementations, the reference molecule can be considered in the map where a cluster of a user-defined size is considered around it. The molecules in the cluster containing the reference molecule can be sampled to have similar sampled molecules from the map. The reference molecule is also received as one of the inputs 102 and the reference molecule data undergoes preprocessing and feature extraction methods which were used for other data. In some embodiments, system 100 can sample over time. For example, assume data 102 are gradually received by system 100 as online or streaming data (e.g. streaming data or online data or temporal data). Then, system 100 can represent the map over time by completion of data. Also, at every time step, sampling can be performed. By more completion of the map, system 100 may form clusters better and better sampling can happen. An example use case is having samples at early time slots too, especially if the speed of the streaming data is very low. System 100 can help provide insight into disease progression by sampling antibodies or paratopes over time. For example, system 100 compare normal healthy antibody repertoire to early stage disease mid stage disease and late stage disease. There may be certain disease targets that develop over the course of the disease. New paratopes that emerge over the time course of the disease can represent potential diagnostic biomarkers and therapeutic interventions. In vaccine development, a map could indicate the impact of booster doses to see how in vivo production of antibodies improves (or not) over successive boosts.

The sampled molecules can be exported in any format for further analysis. For example, the sampled molecules can be exported in the formats of PDB, FASTA, CSV, spreadsheet, text, tables, data frames, etc. In addition to the sequence and structure information of the molecules, other properties and characteristics of the sampled proteins can also be exported; for example, hydrophobicity, charge, and solvent exposure, etc., can be exported.

In the visualization of the map, in some embodiments, the system 100 can generate one or more metrics about the molecules, such as by coding any score of any type as the characteristics of the map visualization (216). For example, a score or scores can be coded by marker shape, marker size, color, or color transparency. A score can be coded as one characteristic or multiple characteristics of visualization. Moreover, multiple scores can be coded in the same map as one or different characteristics of visualization. The score can also appear with legend labels so a legend on the visualization determines how the scores appear in the map.

The score can be either discrete or continuous. For coding scores as some of the visualization characteristics 216, the score can be discrete and finite because those visualization characteristics may have finite options. In those cases, a discrete score can be used, or the score can be quantized if the score is continuous. For example, for coding the score as marker shape, the score can be quantized. Any quantization method can be used for quantization of the scores.

In some embodiments, before coding the scores in the map 216, it is possible to preprocess the scores using different methods. Some example preprocessing methods are histogram equalization, quantization, adjusting, centering, standardization, normalization, Z-score normalization, min-max normalization, transforming scores to fall in a specific range, clipping, saturating, etc. Any transformation can be applied to the scores where the transformation can be any transformation such as linear, affine, and nonlinear transformations.

If the molecule is protein or antibody, a possible score which can be coded in the map (216) can be expressibility (expression) scores. The expressibility scores or yields can either be measured by experiments in laboratory or they can be predicted using any machine learning algorithm. For example, a neural network can be trained for regressing the yield value of every protein.

If the molecule is protein or antibody, another possible score which can be coded in the map (216) is panning scores. The panning procedure of proteins can include multiple rounds where in every panning round, the number of target proteins and control proteins are counted. In some implementations, there can be two types of control proteins, i.e., internal and external control proteins. As a result, every panning round can contain the information of the number of target, internal control, and external control proteins. The ratios of target to internal control and target to external control can be obtained using any formulation. An example formulation for the ratios of target to internal control and target to internal control can be:

$$\frac{TG - IC}{TG + IC},$$

$$\frac{TG - EC}{TG + EC},$$

respectively, where TG, IC, and EC denote the counts of target proteins, internal control proteins, and external control proteins, respectively. These scores are between zero and one. These scores can be called panning scores for example. Usually, if a protein has a large number of targets and low number of internal and/or external control proteins across different panning rounds, that is a good protein to process further. As a result, in some implementations, it is possible to use the panning scores where the larger panning scores in different panning rounds are desired. In every experiment, the desired rules can be collected from the experts in panning. In some implementations, simple sorting can be used whereas in some implementations, fuzzy logic can be used where the fuzzy rules can be constructed out of the experts' rules. Any fuzzy reasoning method and fuzzy inference system can be used. For example, Mamdani or Sugeno (Takagi-Sugeno-Kang) or Tsukamoto fuzzy systems can be used along with any T-norm and S-norm. The rules can be based on any information such as panning scores and panning information in different panning rounds. The antibodies can be ranked based on the output scores of the fuzzy systems, called fuzzy scores. The top-ranked proteins have better fuzzy scores, which can indicate that they are more desirable to process further.

The fuzzy reasoning can be used for any score and not merely for panning scores. Different types of scores and set of experts' rules can be used to construct fuzzy rules and fuzzy inference system to obtain fuzzy scores. The fuzzy scores, obtained from any type of score and rules, can be coded in the map as any visualization characteristic 216.

Figure 3:
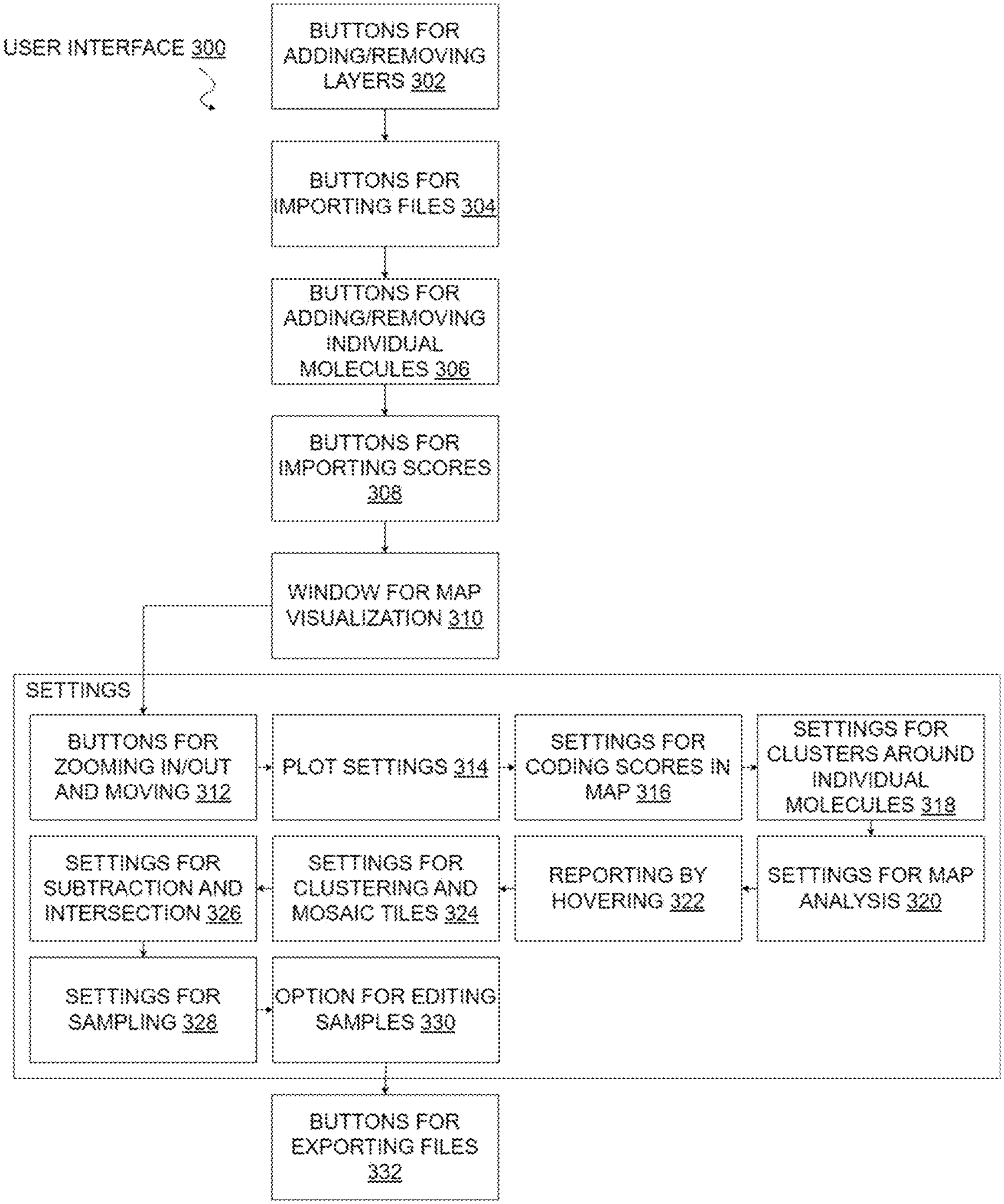
FIG. 3 is a flow diagram of an example user interface, in accordance with an embodiment.
Figure 7:
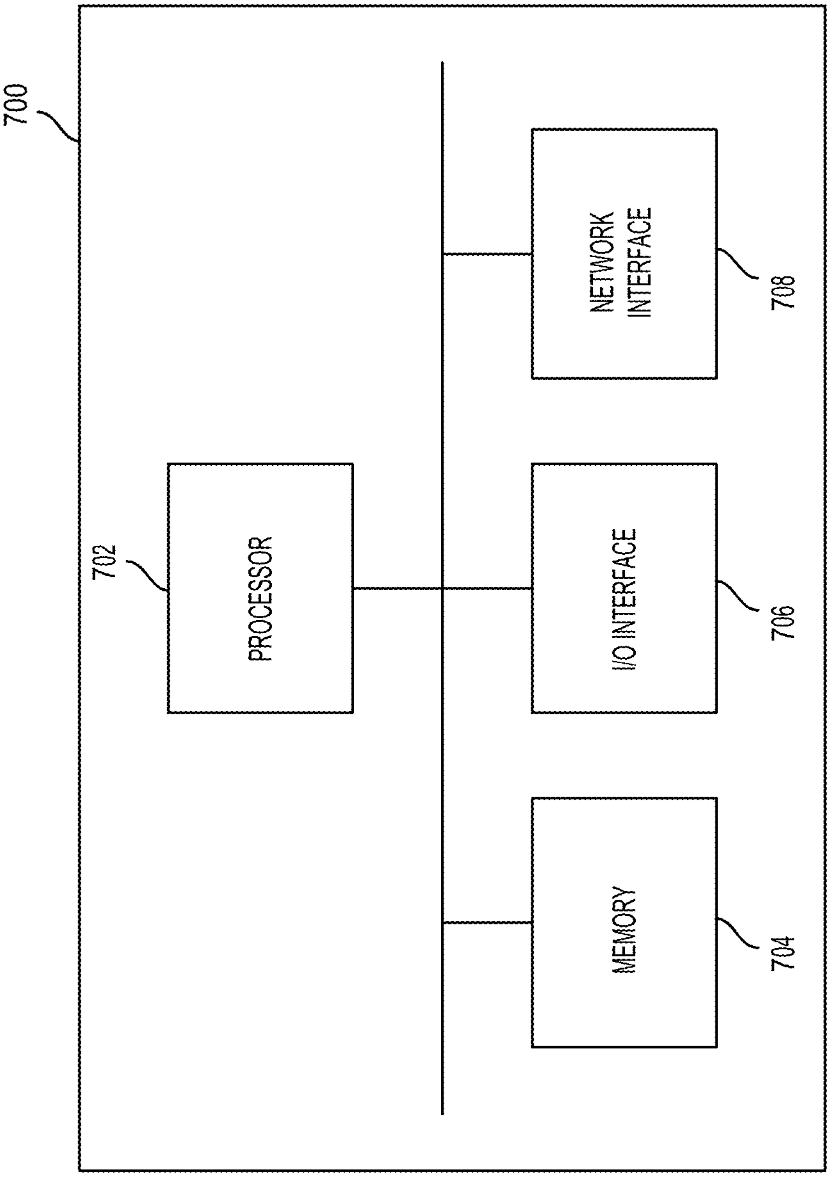
FIG. 7 is a schematic diagram of a computing device, in accordance with an embodiment.

The molecule map 200 can be provided to and/or implemented in a map user interface 300. FIG. 3 illustrates an example schematic for the map user interface 300. The map user interface 300 can be of any type of interface or platform. For example, it can be a Graphical User Interface (GUI) for display at a device. The map user interface 300 can be implemented as a stand-alone visualization, a web-based platform, a computer program, an execution (.exe) file, a portable file, a mobile application, etc. The map user interface 300 can be run in any platform, any operating system, or any server. For example, it can be run in computers, laptops, personal computers, cell phones, cloud servers, web servers, web browsers, and various operating systems of computers, cell phones, and tablets. An example computing device 700 is shown in FIG. 7. In some embodiments, the map user interface 300 can be a paratope map to visualize the immune response data. The map user interface 300 can provide improved visualization of data with system 100 using a dimensionality reduction process to generate the visualization from the dataset 106.

For example, system 100 can use one or more generative models, such as generative machine learning or generative artificial intelligence, to generate interpolating or extrapolating molecules in the map. For example, the user can select or click on some part in the map without any molecule. Then, the system can generate the molecule or characteristics of the molecule, if there were an actual molecule at that part of the map. This generation of molecules out of the map can have various applications. For example, artificial molecules can be generated which mimic real molecules. Also, generative machine learning can be used to analyze different parts of the map to inspect what characteristics are dominant or more important in that part of the map. In some embodiments, the system 100 can implement a process of translating map data into protein data, e.g., using generative models.

Figure 4:
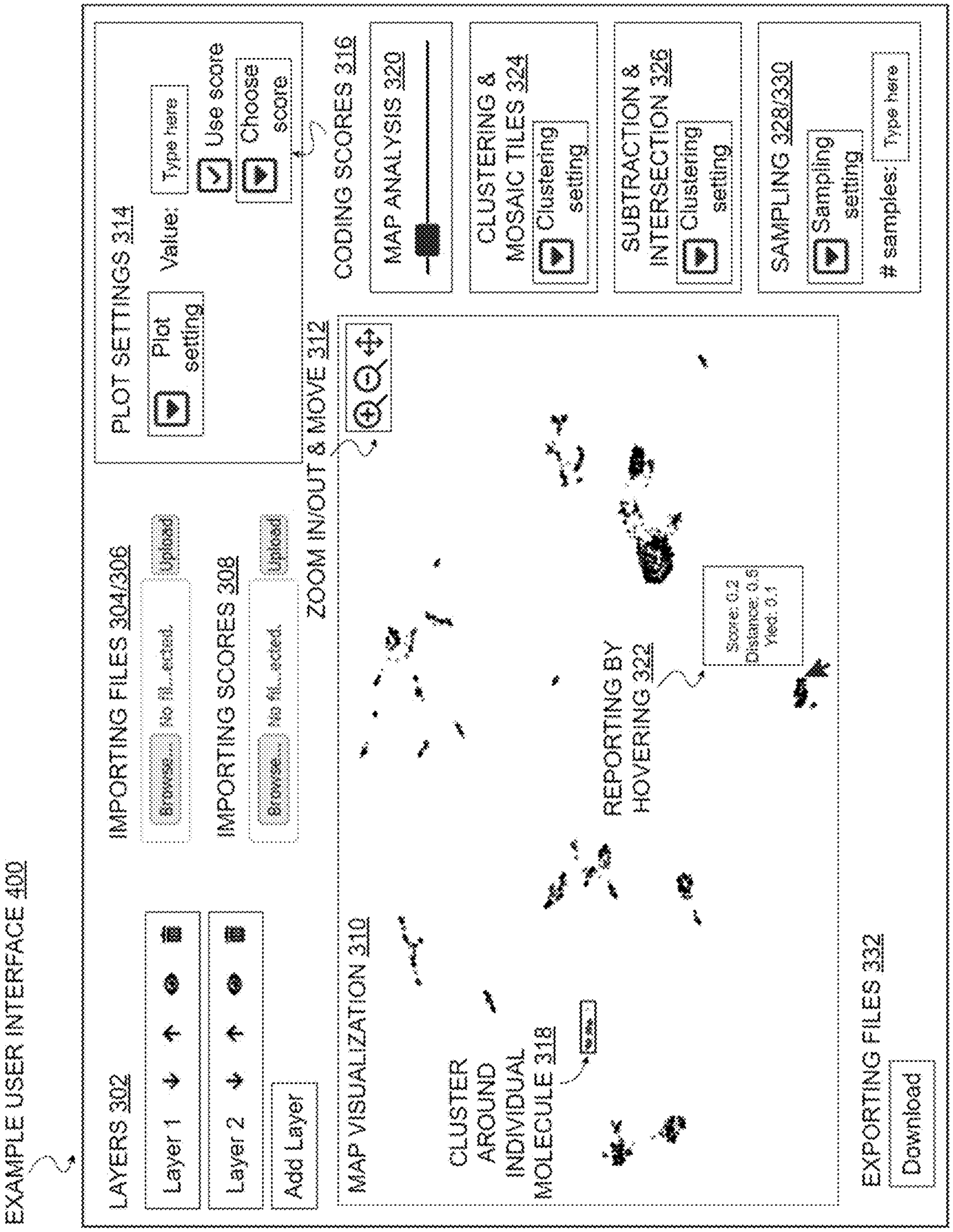
FIG. 4 is an example user interface for importing/exporting the files, visualizing the map, and selecting the settings by the user, in accordance with an embodiment.

An example user interface 400 is depicted in FIG. 4. The user interface 400 can be interactive by updating the visualization (e.g. map visualization 310) in response to receiving control commands. The user interface 400 can have any types of buttons to provide control commands to update the map visualization 310. For example, user interface 400 can have regular buttons, radio buttons, check boxes, pop-up menus, tables, sweeping bars, browse buttons, upload/download buttons, submit buttons, running buttons, zoom/move buttons, selection options, visualization windows, etc. to provide different values relating to the control commands to explore, analyze and inspect the map visualization 310. Every point in the map can represent a molecule or a group of molecules. In some implementations, every point in the map is for a molecule. An input control can hover or click over points on the map for selection, interaction, etc. The visualization of each dot representing an individual molecule can be used to visually indicate the relevance of distance between each dots and clusters. Dots or data elements are "clickable" to have access to information on the molecule. In some embodiments, there may be an associate e-commerce service such that clicking a dot on a map can add the antibody to a cart. This may result in the antibody being manufactured and shipped to a client, or if additional assays were ordered as "add-ons", then the antibodies can be shipped to the service provider for testing and the results sent to the customer.

In some embodiments, the user interface 300, (including the example user interface 400), can have buttons for adding and removing layers of the embedding 302. The "Add Layer" button and the trash icon in the embedding 302 of 400 are for adding and removing layers, respectively. The layers can be moved up and down by the user to change the order of layers. The layers in later orders can be visualized on top of the previous layers. For example, the up/down arrows in the embedding 302 of the example user interface 400 can be used for moving layers of the embedding 302. Every layer can also be hidden or displayed in the user interface 400 in response to receiving control commands from e.g. the user. The eye icons in 302 of 400 can be used for hiding or displaying layers of the embedding 302.

The user interface 300 (including e.g. example user interface 400), can have buttons for importing files 304. In some embodiments, data 102 can be received by system 100 by importing files 304, which may be referred to herein as imported data files 102. The imported data files 102 can be of any format, e.g., PDB, FASTA, text, spreadsheet, CSV, data frame, tables, etc. For example, the PDB or FASTA files of the proteins can be uploaded to the system. In the background of the user interface 300, data preparation 104 is performed by mapping system 100 to prepare the dataset 106. Then, the system 100 can prepare the molecule map 200.

The user interface 300, an example of which is the user interface 400, can have buttons for adding or removing individual molecules of interest 306, e.g., reference molecules or target molecules. The imported data files 102 for the individual molecules of interest 306 can be of any format, e.g., PDB, FASTA, text, spreadsheet, CSV, data frame, tables, etc. In the background of the user interface 300, data preparation 104 can be performed by system 100 to prepare the dataset 106. The system 100 can prepare the molecule map 200 of the molecules of interest 306 to be included in the rest of the map. The user interface 300 can have settings and options to report by hovering or clicking on the molecules or points in the map. The user interface 300 can receive selections on which information is to be reported or displayed e.g. by hovering or clicking on input on the molecules.

The user interface 300, an example of which is the user interface 400, can have buttons for importing scores 308, which are example metrics about molecules The scores can be any type of score as was introduced in step 216 in system 100. Some example scores are expressibility scores and fuzzy scores of proteins. The scores can be imported in any format, e.g., spreadsheets, data frames, tables, CSV files, text files, etc.

The user interface 300, whose example is the interface 400, can have a window for visualization of the map 310. As was explained in steps 202 and 202 of FIG. 2 implemented by the system 100, the visualization of the map can be of different dimensions. For example, it can be one-dimensional, two-dimensional, three-dimensional, or higher-dimensional. It can also change over time to be a time-series of visualizations of any number of dimensions. That is, time can provide an additional dimension for the visualization. The visualization window 312 of the map 310 can be of any shape, e.g., rectangular, square, sphere, etc.

The user interface 300, an example of which is the user interface 400, can have buttons for zooming in or out in the visualization window 312. It can also have buttons for moving in the visualization window 312. By clicking on the zoom in/out buttons, the system 100 can identify or select a region in the map to zoom in/out in that region (e.g. by receiving selection input at the user interface 300). The user interface 300 can also be used to receive control commands to drag the map to move from parts to parts in the map to inspect the map and the visualization better and with more care.

The user interface 300, whose example is the interface 400, can have buttons, pop-up menus, and selections for plot settings 314. For example, it can have pop-up menus for plot settings. In some implementations, the pop-up menus can have options for marker shape, marker size, color, color transparency, and legend. By selecting each of these settings, the user can enter/type the value of that setting in a text box provided in the interface. Alternatively, another pop-up menu can be shown to user to select one of the possible values for that setting. The user can also have an option to choose an imported score or a calculated score by the system 100 to be coded as any of the selected plot settings in the pop-up menu. By doing that, the corresponding plot setting can code that score as the corresponding visualization characteristic. It is possible to use one score for coding multiple plot settings such as marker shape, marker size, color, color transparency, and legend. It is also possible to use multiple scores to be coded as different plot settings and visualization characteristics. The score or scores can either be imported by the user (316) or can be calculated by the system 100. Some example scores are expressibility scores and fuzzy panning scores.

The user interface 300, an example of which is the user interface 400, can have settings, buttons, and pop-up menus for selecting clusters around individual molecules of interest 318, such as reference or target molecules. The user interface 300 can receive selection of the shape of the cluster and the size of cluster along every dimension. The user interface 300 can also receive selection of the location of the individual molecule of interest in the cluster, whether to be at its center or somewhere else in the cluster. The user interface 300 can have the option to receive selections of multiple molecules of interest where a cluster contains them all or each molecule of interest can have a cluster around it.

The user interface 300, an example of which is the user interface 400, can have settings for map analysis 320. Any button, popup menu, or sweeping bars can be used for the settings. The map analysis 320 module can analyze the map and embedding of molecules in any way. For example, map analysis 320 can cluster the map and return the cluster and the number of clusters as part of the visualization of the map 310. The map analysis 320 can have hyperparameters to sweep and change the number of clusters (because clustering is an ill-defined problem and needs to have hyperparameters). As another example, the map analysis 320 can detect the large and small cluster or inlier and outlier (anomalous) molecules to inspect them further.

The user interface 300 (e.g., the user interface 400) can have settings and options to report by hovering on the molecules or points in the map (322). For example, by moving the cursor on the map, any desired or chosen information—corresponding to the molecule in the map—can be reported as a box near the cursor. The user interface 300 can receive selections on which information is to be reported or displayed e.g. by receiving hovering input on the molecules. For example, the score(s) selected by user (e.g. received as selection input by user interface 300), such as expressibility yield or fuzzy panning score, can be reported. Also, for example, the distance/difference or similarity of the molecule to its closest molecule can be reported. The average distance or similarity to other molecules in the map or in the same cluster can also be reported as another example.

The user interface 300 (e.g., user interface 400) can have options for settings for clustering and mosaic tiles (324). For example, the user can adjust the clustering and mosaic tiles based on their preferences or to better display the molecules based on features or aspects of the molecules.

Figure 17:
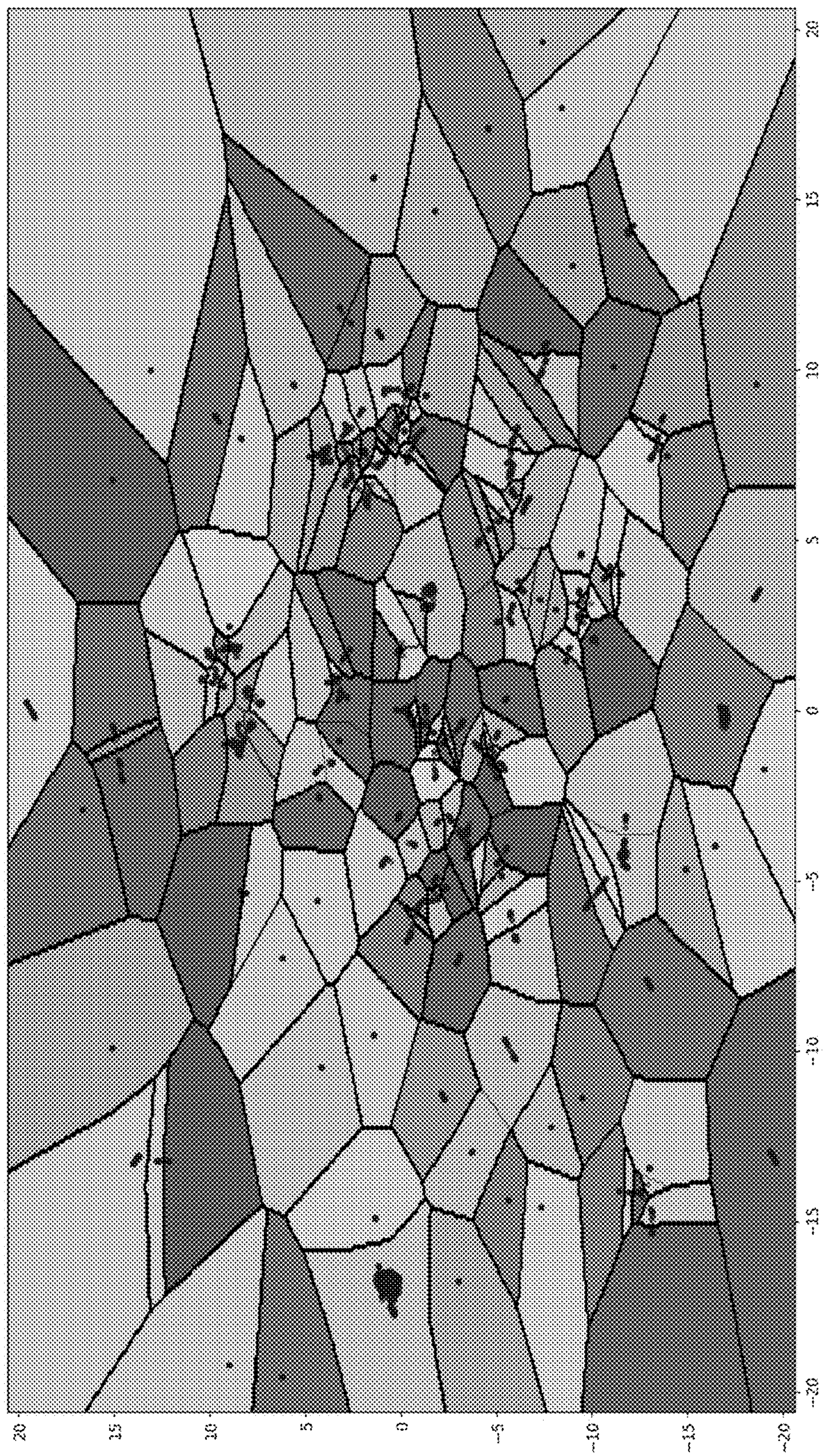
FIG. 17 shows an example mosaic tile map, according to some embodiments.

FIG. 17 shows an example mosaic tile illustration, according to some embodiments.

The interface of molecules can be divided into multiple clusters (e.g., to provide a straightforward manner to interface with which to interact with in step 322). The clusters that partition the space can resemble mosaic tiles. Each mosaic tile can represent a cluster of molecules. An example of mosaic tiles is displayed in FIG. 17 in which the mosaic tiles are illustrated along with molecules (displayed by dots) in the interface. The mosaic tiles or the clusters can be obtained using any method of clustering and space partitioning.

In some implementations, any clustering algorithm (e.g., DBSCAN, HDBSCAN, or K-means) can be used to cluster the molecules in the interface. The advantage of DBSCAN and HDBSCAN compared to K-means can be that they do not need the prior knowledge of number of clusters; rather, by setting and tuning some parameters, they can cluster molecules properly regardless of the number of clusters. These parameters can be set depending on the desired minimum cluster size. For example, the minimum cluster size can be set such that each outlier becomes a cluster.

Once the molecules on the interface have been partitioned into mosaic tiles, they can be identified using cluster labels. For this, any of the following two exemplary approaches can be used. In one approach, the cluster label of every molecule can be determined to be the label of its closest molecule(s) in the space. In case multiple nearest molecules are considered, majority voting can be used. In another approach, the cluster label of every molecule can be determined to be the label of its closest cluster center in the space. The example in FIG. 17 uses the first approach for example. Labels may include strings, numbers, barcodes, names. Labels may be descriptive of the molecule(s) found within the respective cluster or they may be descriptive of the methodology used to cluster the molecules.

Partitioning the space can require going through the space with some step/resolution and use the above mentioned algorithm to find the cluster label of each point in the space. A finer step/resolution can make the mosaic tile borders smoother and more accurate, but it can make the run of algorithm slower.

After finding the cluster labels of points in the space, the mosaic tiles are calculated and each molecule which falls in a mosaic tile can be given the cluster label of that mosaic tile. The molecules to be clustered by mosaic tiles may or may not be in the training data.

Figure 18:
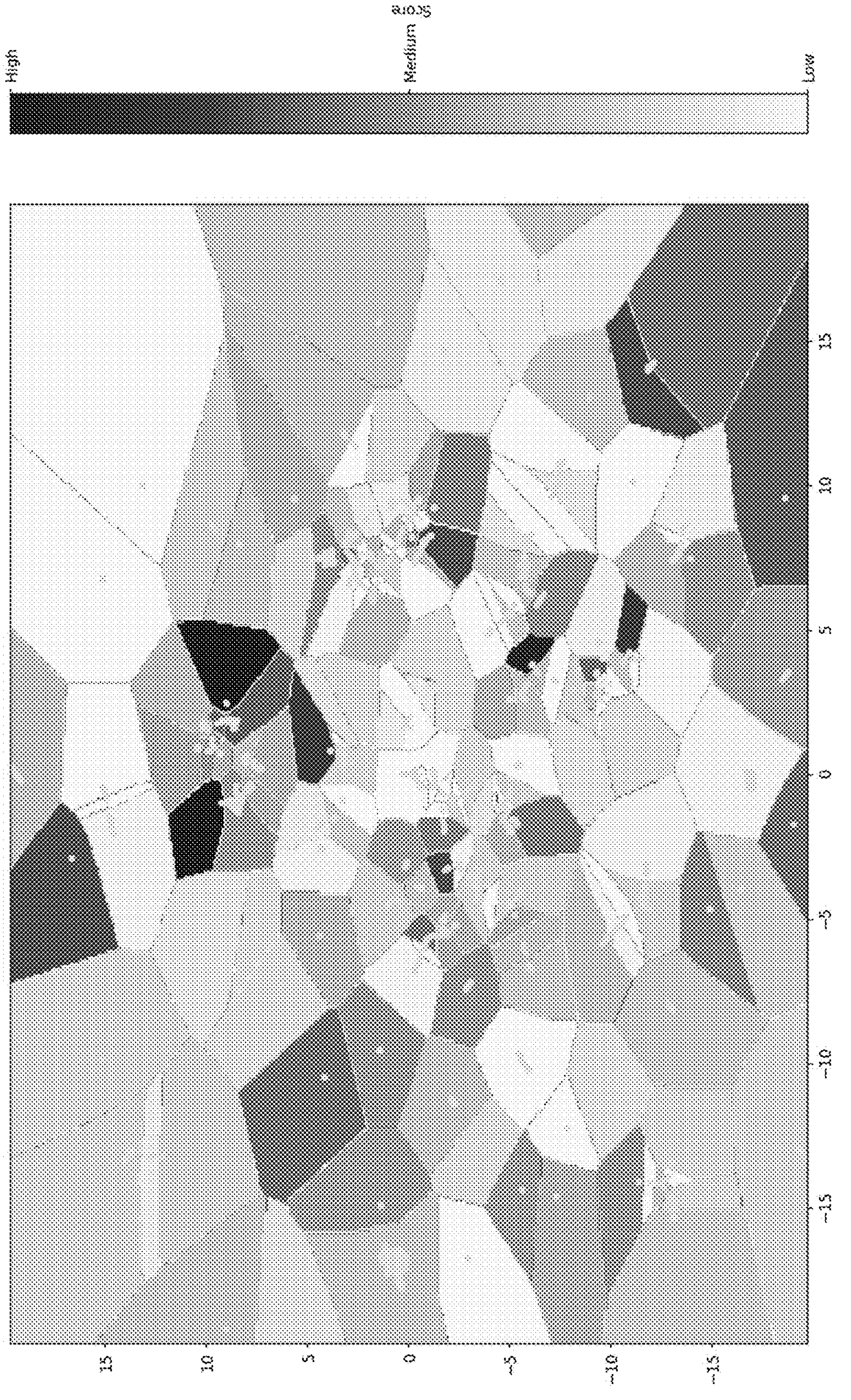
FIG. 18 shows another example mosaic tile map using score colour-coding, according to some embodiments.

FIG. 18 shows another example mosaic tile illustration using score colour-coding, according to some embodiments.

The mosaic tiles can be without color, or they may be colored in various ways. For example, they can be colored (or patterned) randomly as in FIG. 17. Another approach for coloring the mosaic tiles is to color-code the tiles using scores or quantities such as protein yield, enrichment quality (e.g., the prevalence of a particular sequence in the target panning data compared to the control panning, and how that changes over multiple rounds of panning), binding energy, and population/density of cluster it belongs to. An example of coloring the mosaic tiles by scores is illustrated in FIG. 18. The mosaic tiles that have been color-coded using the scores can allow for better inspection of clusters.

Different techniques can be used to have more contrast between the colors of the mosaic tiles. For example, when coloring the tiles randomly, a graph coloring algorithm can be used to make sure that the mosaic tiles have different colors as much as possible to provide contrast between tiles. Another way of enhancing contrast between tiles can be to use histogram equalization or other transforms on the colors of tiles.

The mosaic tile can be displayed in two different exemplary ways: mesh grids and polygons. The mosaic tiles can be displayed using a mesh grid in the space of interface and each point in the grid can be colored with the color of the tile in which it exists. If the step size of the grid is small enough compared to the zoom of the interface, the mosaic tiles can be colored appropriately. The mesh grid may appear to be a grid while zoomed out, but small points when zoomed in. Another approach can be to calculate the contours of the mosaic tiles and visualize them as polygons with varying number of corners.

Mosaic tiles can have various applications. For example, they can be used for clustering or grouping the molecules or partitioning the space and assigning new molecules to clusters in the interface. They can also be used for summary statistics of the interface. Another example use of mosaic tiles can be sampling, such as stratified sampling, from the mosaic tiles. Moreover, it can be possible to subtract or intersect two cluster tiles, possibly from the same interface or two different interfaces.

The user interface 300 (e.g., user interface 400) can have options for settings for subtraction and intersection (326). For example, the molecules can be intersected and subtracted as described above to produce a new set of molecules to review.

Figure 19:
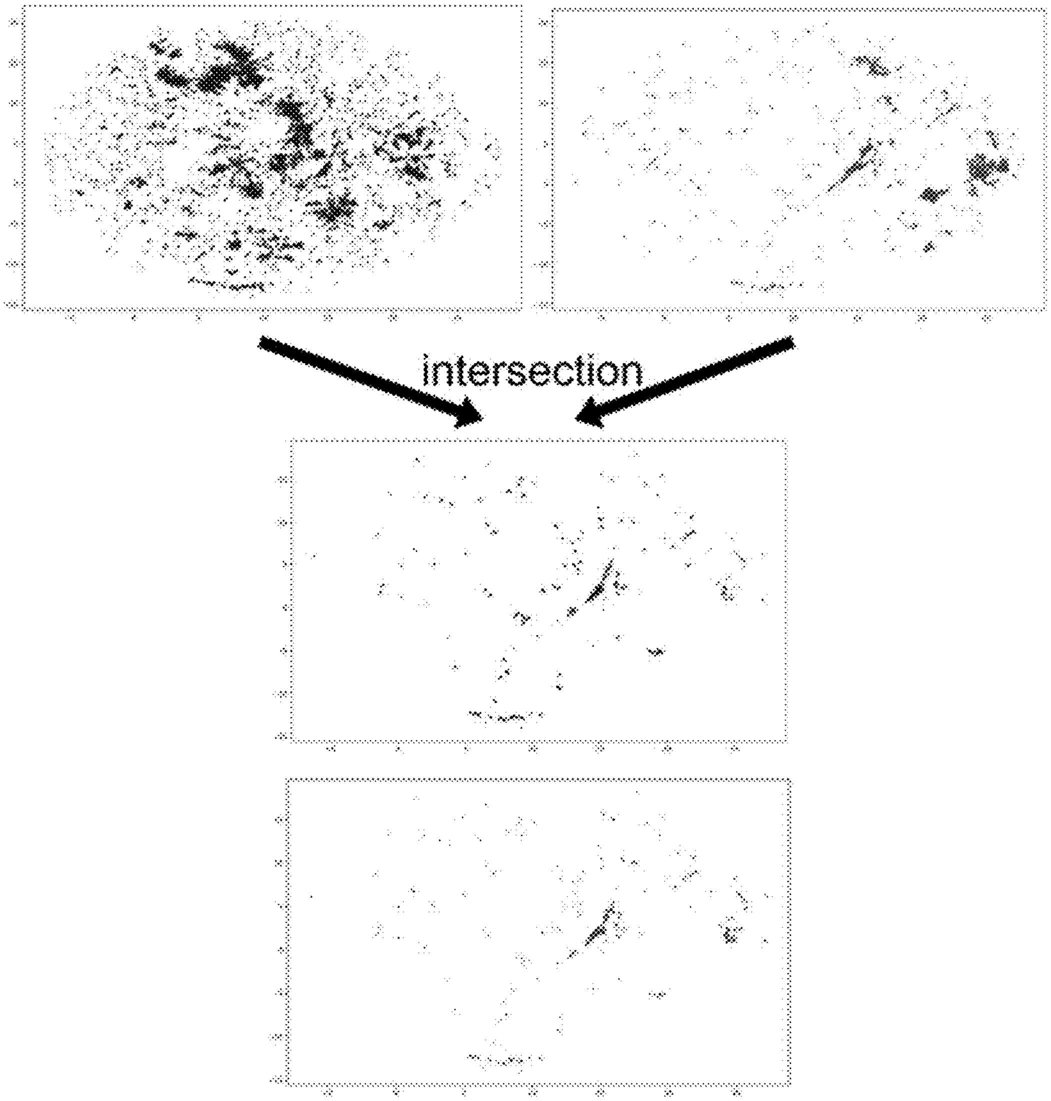
FIG. 19 shows an example intersection of two layers, according to some embodiments.

FIG. 19 shows an example intersection of two layers, according to some embodiments.

It can be possible to intersect multiple interfaces of molecules or multiple layers in an interface of molecules, where multiple refers to two or more. The following explanation is for intersection of multiple layers, but can also apply to multiple interfaces, where interfaces should be used instead of layers.

Intersection and subtraction of interfaces or layers can have many applications and use cases and may be carried out as part of step 326 below One example can be that intersections can be used for filtering out the shared molecules between two layers or two interfaces. Conversely, for example, subtraction can be used for filtering out the molecules which are not shared between two or more layers or interfaces. As instance, the molecules having cross-reactivity can be removed. Another example can be antibodies that do not bind to a specific target antigen may be removed by subtracting antibodies of an unimmunized animal from the antibodies of an animal immunized with a target. Another example use case of subtraction and intersection can be sampling from the shared or not shared regions of layers/interfaces.

Following an example method for intersection of layers, let n denote the number of layers to be intersected where n can be an integer greater than or equal to two. For the intersection of multiple layers, the layers can be considered together and a hypersphere or a hypercube, with some radius/length, can be considered around every molecule in each layer. Then, for every layer, the method can iterates over all (n−1) other layers. Hyperspheres/hypercubes can be considered around molecules in every other layer. In every iteration, the molecules of the layer falling in the hyperspheres/hypercubes can be retained and logged and the rest can be dropped. Doing this procedure for all n layers can provide n interfaces each of which corresponds to a layer after intersection. An example of intersection of two layers is displayed in FIG. 19. Increasing the radius may include more results in the intersection while reducing the radius may decrease the results in the intersection.

It can also be possible to intersect multiple interfaces or layers with at least several levels of intersection. For example, consider four layers. The intersection of each layer with at least one other layer, two other layers, or all three other layers can be computed. Intersection with at least a greater number of layers may be a harder condition resulting in a smaller number of retained molecules after intersection.

One possible application of intersection of interfaces or layers can be to find non-specific antibodies which exist in the interfaces or layers of molecules corresponding to multiple targets. For example, a master interface of antibodies for several targets can be considered where each layer corresponds to the antibodies for a target. If an antibody exists in the intersection of multiple layers, it can imply that the antibody is non-specific for the corresponding target of its layer. The greater the number of layers an antibody is found in, the less specific that antibody may be. For example, if an antibody exists in multiple layers, it may be more likely to be cross-reactive with multiple targets.

Figure 20:
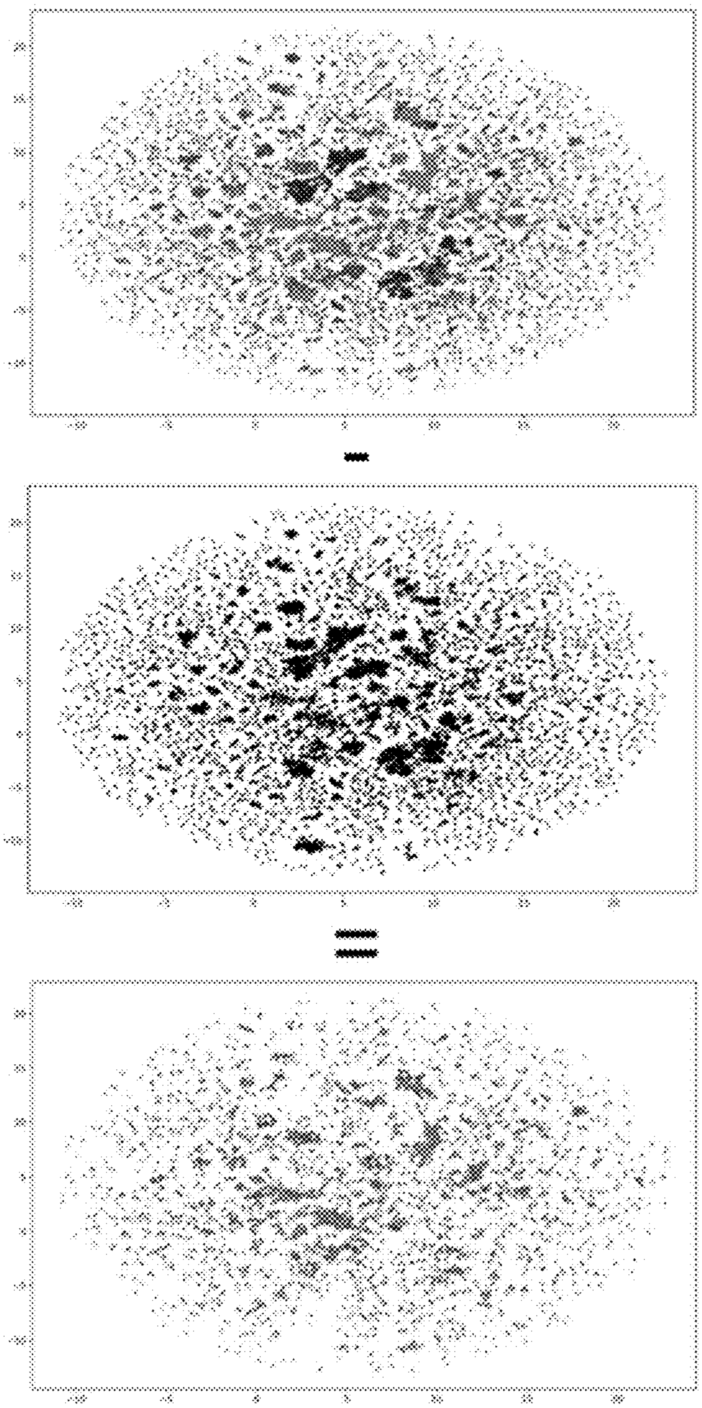
FIG. 20 shows an example subtraction of one layer from another, according to some embodiments.

FIG. 20 shows an example subtraction of one layer from another, according to some embodiments.

It can also be possible to subtract multiple interfaces of molecules or multiple layers in an interface of molecules from each other, where multiple refers to two or more. This operation can provide the opposite functionality to intersection of interfaces or layers. Subtraction of multiple interfaces is generally the same where interfaces should be used instead of layers.

Following an example method for subtraction of layers, assume (n−1) layers, called L_1, L_2, . . . , L_{n−1}, are needed to be subtracted from a layer called L_0, where n is an integer greater than or equal to two. For the subtraction of the layers L_1, L_2, . . . , L_{n−1} from the layer L_0, a hypersphere or a hypercube, with some radius/length, is considered around every molecule in each of the layers L_1, L_2, . . . , L_{n−1}. Then, for every molecule in the layer L_1, all molecules of the layer L_0 which exist in the hypersphere/hypercube around that molecule are removed. This procedure can be performed for all molecules in each of the layers L_1, L_2, . . . , L_{n−1}. Therefore, each of the (n−1) layers may remove some of the molecules from the layer L_0. The resultant interface can be the subtraction of layers L_1, L_2, . . . , L_{n−1} from layer L_0. An example of subtraction of two layers is displayed in FIG. 20. Increasing the radius may subtract more molecules from the result while reducing the radius may increase the number of molecules in the result.

Intersection and subtraction of interfaces or layers can find or remove similarities of interfaces or layers based on any feature depending on the input data to the interface. For example, if the input data are the sequence of antibodies, intersection and subtraction can select or remove antibodies with similar sequences. If the data are based on structure or biophysical properties of antibodies, for example, then intersection and subtraction of layers can select or remove antibodies with similar structures or biophysical properties of antibodies.

The user interface 300 (e.g. the user interface 400) can have settings for sampling from the map (328). Sampling can be performed from the whole map or some specific parts of the map. Samples can also be drawn from some clusters of interest or from clusters around the individual molecules of interest 318. As was explained in step 214 in system 200, different sampling methods can be used where the user can choose it. For example, simple random sampling or stratified sampling, with or without replacement, can be used. Sampling can also be done proportionally to the cluster sizes in the map. As shown in FIG. 4, the user interface 300 can receive as input: the sampling method, the total number of samples, whether to sample proportionally to the sizes of clusters, etc. The user interface 300 can also receive as input the plot settings for how to visualize the drawn samples in the map visualization window. For example, the marker shape, marker size, marker color, marker color transparency, and legend labels of the drawn samples can be selected by the user.

The user interface 300 (e.g. user interface 400) can have the option for editing the drawn samples in the map (330). Different methods for editing can be used for editing the samples. For example, the user can hover the cursor on the samples to move them by dragging and dropping in the map visualization window. Alternatively, the user can edit the samples in a table or pop-up menu or by some button(s).

The interface can be used for sampling of molecules. Sampling of molecules can be done for various reasons. For example, sampling can be used to select molecules for further investigation in laboratories.

Different sampling methods can be used for sampling molecules. Various sampling methods, such as simple random sampling, bootstrapping, sampling with or without replacement, stratified sampling, cluster sampling, multi-stage sampling, network sampling, snow-ball sampling, and Monte Carlo sampling, can be used. For example, the simplest sampling algorithm may be simple random sampling in which the molecules are sampled randomly. The random seed, for randomness generation in computers, can be either set or unset to be able or not be able to reproduce the outcome, respectively.

Another possible sampling algorithm which can be used can be stratified sampling to sample from clusters or mosaic tiles proportionally to the size of clusters or tiles. In this method, the larger a cluster or a tile is, the more samples are taken from it. In this method, the interface of molecules can first clustered into multiple clusters or tiles using any clustering algorithm such as DBSCAN, HDBSCAN, K-means, or hierarchical clustering. The parameters of the clustering algorithm can be set based on whether the small clusters are desired to be considered as separate clusters or not. The number of samples to be drawn from each cluster can be calculated according to the relative size of its cluster or tile to all the interface and other clusters or tiles. For example, the sample size of every cluster can be calculated by:

round ((cluster_population/all_population)*n_samples), where cluster_population is the size of cluster or tile, all_population is the total number of molecules in the interface, and n_samples is the desired total number of samples. If the calculated number of samples selected from tiny clusters or tiles is zero, the number of samples from each of those clusters can be set to one or a larger number. This can be done when the user desires to have sample(s) from outlier or small clusters in addition to samples from the larger clusters.

Figure 21:
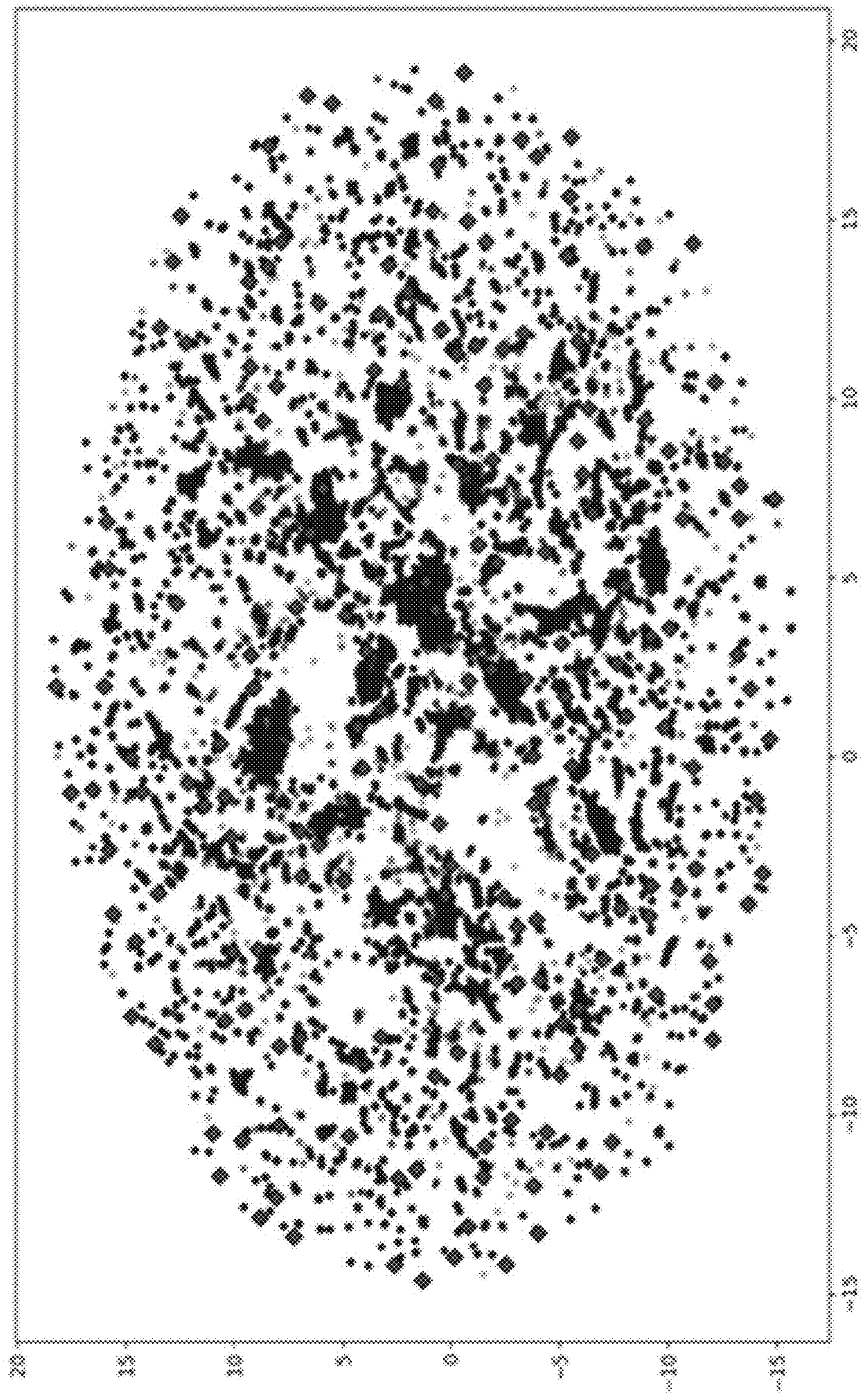
FIG. 21 shows an example of diverse sampling from the map interface, according to some embodiments.

FIG. 21 shows an example of diverse sampling from the interface of molecules, according to some embodiments.

The samples can be drawn either randomly or diversely from clusters or tiles. Diverse sampling from clusters or tiles can be achieved by another clustering applied to every cluster to have subclusters in each cluster. In every cluster or tile, the number of subclusters can be equal to the number of samples to be drawn from the cluster. For example, K-means can be used, with K equal to the number of samples to be drawn from the cluster. Then, either a sample can be drawn randomly from each subcluster in the cluster/tile (stochastic approach) or the centers/medoids of the subclusters can be considered as the samples from the cluster/tile (deterministic approach). An example of diverse sampling from the interface of molecules is shown in FIG. 21.

In stratified sampling from clusters, either hard clustering or soft clustering can be used where hard clustering can assign each molecule fully to a cluster while soft clustering can provide scores of assignment of molecules to clusters. It can be possible to have soft clustering using different methods such as hierarchical clustering. In hierarchical clustering, a cut-off can be used to define the height in the hierarchy and each cut-off determines the clusters. By changing the cut-off, some clusters can be merged into one cluster, or a cluster may be divided into smaller clusters.

It can be possible to sample from the mosaic tiles of the interface of molecules. For this, first mosaic tiling, described before, can be applied to the interface of molecules. Then, samples can be drawn proportionally to the sizes of tiles; this can be equivalent to stratified sampling, described above. Alternatively, the distance of each molecule from the center of the representative of its mosaic tile/cluster can be calculated. The probability of sampling can be determined according to this distance. For example, the molecules closer to the tile center can have larger probability of being sampled.

The drawn samples can also be diverse according to the parts of the sequence of molecules. For example, when the molecules are antibodies, the samples can be diverse in terms of sequence parts of antibody chain(s), such as frameworks or complementarity-determining regions (CDR). For examples, the samples can be diverse in terms of CDR3 which can be important regions in the paratopes of antibodies to determine binding specificity to an antigen.

For diverse sampling based on the parts of the sequence of molecules, a numbering method such as IMGT numbering can be applied to the sequences so the residues in the same position correspond to each other across different sequences. Then, the parts of interest in the sequence of the molecules, such as CDR3, are considered in the interface. The parts of the sequences can be categorized into multiple unique categories. Then, one or multiple molecules can be sampled from each category of sequence parts.

Categorizing or clustering the parts of sequences into groups, where each group contains a unique part, can be a hard categorization. It can also be possible to have soft categorization, in which each of the parts of the sequences can be assigned scores of assignment to the categories. It can be performed by different techniques such as hierarchical clustering. For example, in a hierarchical clustering, a cut-off can be used in the height of hierarchy of categories and depending on the cut-off, a part of the sequence can be in one of the categories.

Sampling can also be diverse in terms of structures of molecules or parts of the structures of molecules. For achieving this, either the input data of the interface can be only the specific parts of the structure of molecules or the three-dimensional positions of atoms of the molecules in specific parts of the molecules can be considered when sampling. Optionally, all or some specific parts of the structure of molecules can be considered for diversity of samples. For example, the structure of atoms in the paratope regions, or top of the heavy chains, of molecules can be diverse across the samples.

Another approach for sampling molecules can be to draw samples from the molecules by some probability scores. Any score can be considered as the probabilities of sampling from the interface of molecules. For example, if the molecules are antibodies, the scores can be determined by quantities such as protein yields, enrichment, binding energy, and population or density of cluster it belongs to. The scores can be normalized to be between 0 and 1 and sum to 1 so they behave like probability. The higher the sampling probability score of a molecule is, the more probable it is to be drawn as a sample. Optionally, it is possible to weight multiple probability scores (e.g., by weighted averaging) to have a consensus of multiple scores for sampling.

It is also possible to add descriptors or scores to data to be used to display or hide or toggle the display molecules in the interface of molecules. By doing this, some molecules with low scores can be removed from the interface of molecules and then sampling can be performed on the reduced interface. For example, if the molecules are antibodies, the antibodies with low enrichment scores, which bind to controls or do not bind to the target, can be removed before sampling.

Sampling can be concentrated around one or multiple reference molecules in the interface of molecules. The reference molecules can be any molecule of interest or molecule of importance. For example, it can be an antibody that has been previously shown to bind to a specific target. Sampling additional antibodies in the vicinity of the known binder can increase the likelihood of identifying additional antibodies with similar properties. Moreover, it can be possible to, conversely, sample away from some molecules.

Multiple approaches can be used for sampling around reference molecule(s). For example, samples can be drawn randomly from the cluster or mosaic tile containing the reference molecule. Alternatively, higher probabilities of sampling can be assigned to the molecules closer to the reference molecule. Another approach can be to deterministically get the closest (nearest) molecules to the reference molecule in the interface. Moreover, using the intersection algorithm of molecule interfaces/layers described before, the intersection of the reference molecule with the interface of molecules can be calculated with some radius. Then, samples can be drawn either stochastically or deterministically from the result of intersection.

One other possible approach for sampling is using a probability distribution or a superposition of multiple probability distributions. Each probability distribution can give the chances of sampling molecules across different places in the interface. For example, if the interface is a 2D map, the probability distributions are 2D distributions in the space which can be visualized by colors or heat-maps in the space. For example, some 2D probability distributions are color-coded in FIG. 22A-FIG. 22G, in which the colormap is from blue to red for small to large probabilities.

This type of sampling, by superposition of probability distributions, can be iterative on batches of samples. The batch size can be any integer between one and the desired number of samples inclusive. In every iteration, a batch of samples can be drawn. The drawn samples from all previous iterations can be accumulated and used for updating the probability distributions in the next iteration. The probability distributions might change across iterations. The smaller the batch size, the more accurate sampling can become because samples affect the probability distributions more gradually and more accurately. However, that may make the process of sampling slower because having smaller batches increases the number of iterations to reach the desired number of samples. There can be a trade-off between speed and accuracy of sampling.

In sampling by superposition of probabilities, a weighted average of the probabilities can be used. It can be possible to weight each probability distribution based on its importance in sampling. Any weighting technique can be used. For example, in some implementations, one can use a power transform on each probability distribution with the weight used as the power. By changing the power, it can tune how much each probability distribution concentrates on its mode (so sampling can concentrate on its high probable molecules) or how much like the uniform distribution it becomes.

Superposition of any probability distributions can be used for sampling. For example, in some implementations, the probability distributions can be density of clusters, diversity of samples, proximity to cluster or tile centers, diversity of sequence parts, input scores, proximity to reference(s), and any other criteria which can be added. The probability distribution for density of clusters can be calculated using kernel density estimation or any other density estimation method on the molecules (see, for example, FIG. 22A). In calculating the probability distribution for diversity of samples (see, for example, FIG. 22B), the distance between each molecule and the already drawn samples in the previous iterations can be calculated. For each molecule, the k-nearest neighboring samples can be considered where k can be any positive integer such as one, two, or three. The larger the (average) distance of a molecule from its nearest neighboring sample(s), the higher probability it has for sampling.

In calculating the probability distribution for proximity to cluster or tile centers (see, for example, FIG. 22C), the cluster tiles can be used or the space of molecules can be clustered using any clustering algorithm. Then, the cluster center can be calculated as a summary statistic of the cluster such as mean or weighted average of molecules in the cluster, or as the tile center. Then, the distance of each molecule from the center of its cluster can be calculated. The smaller the distance is, the higher the probability of sampling can be. This can be used to sample more from the cores or centers of clusters.

In calculating the probability distribution for diversity of sequence parts (see, for example, FIG. 22D), can consider any sequence part. For example, if the molecules are antibodies, CDR parts can be considered and the differences of CDR parts of each molecule from the CDR parts of the already drawn samples, from previous iterations, can be computed using any technique such as BLAST (Basic Local Alignment Search Tool) or minimum Hamming distance of two strings by dynamic programming.

In calculating the probability distribution for input scores (see, for example, FIG. 22E), any input score(s) taken from the user can be used. Some examples for the score can be expressibility yields or enrichment scores when molecules are antibodies. The scores can be normalized to sum to one to behave like a probability distribution. This normalization can use any technique such as dividing to the summation of scores or using the softmax function to have a Gaussian-like distribution. Depending on whether the higher scores or lower scores are better, the probabilities obtained from scores can be used as-is or their reverse.

In calculating the probability distribution for proximity to reference(s) (see, for example, FIG. 22F), any input reference(s) provided by the user can be used. The reference molecule(s) can be any molecule such as previously characterized molecules. The distances of each molecule to either all the references or its k-nearest reference(s) can be calculated, where k can be any positive integer. If it is desired to sample close (or respectively far from) the reference(s), then it can be configured such that the smaller (or respectively the larger) the distance is, the higher the probability of sampling becomes.

Any other probability distribution can be added to the probability distributions for sampling. Finally, the superposition of the probability distributions, described above, can be used as the overall probability of sampling (see, for example, FIG. 22G). The samples can be drawn stochastically (e.g., randomly) from this distribution, using any technique such as roulette wheel, inverse of cumulative distribution function, or Monte Carlo sampling. Alternatively, samples can be drawn from the distribution deterministically (e.g., not randomly) by drawing the molecules having the largest probabilities.

Figure 22A:
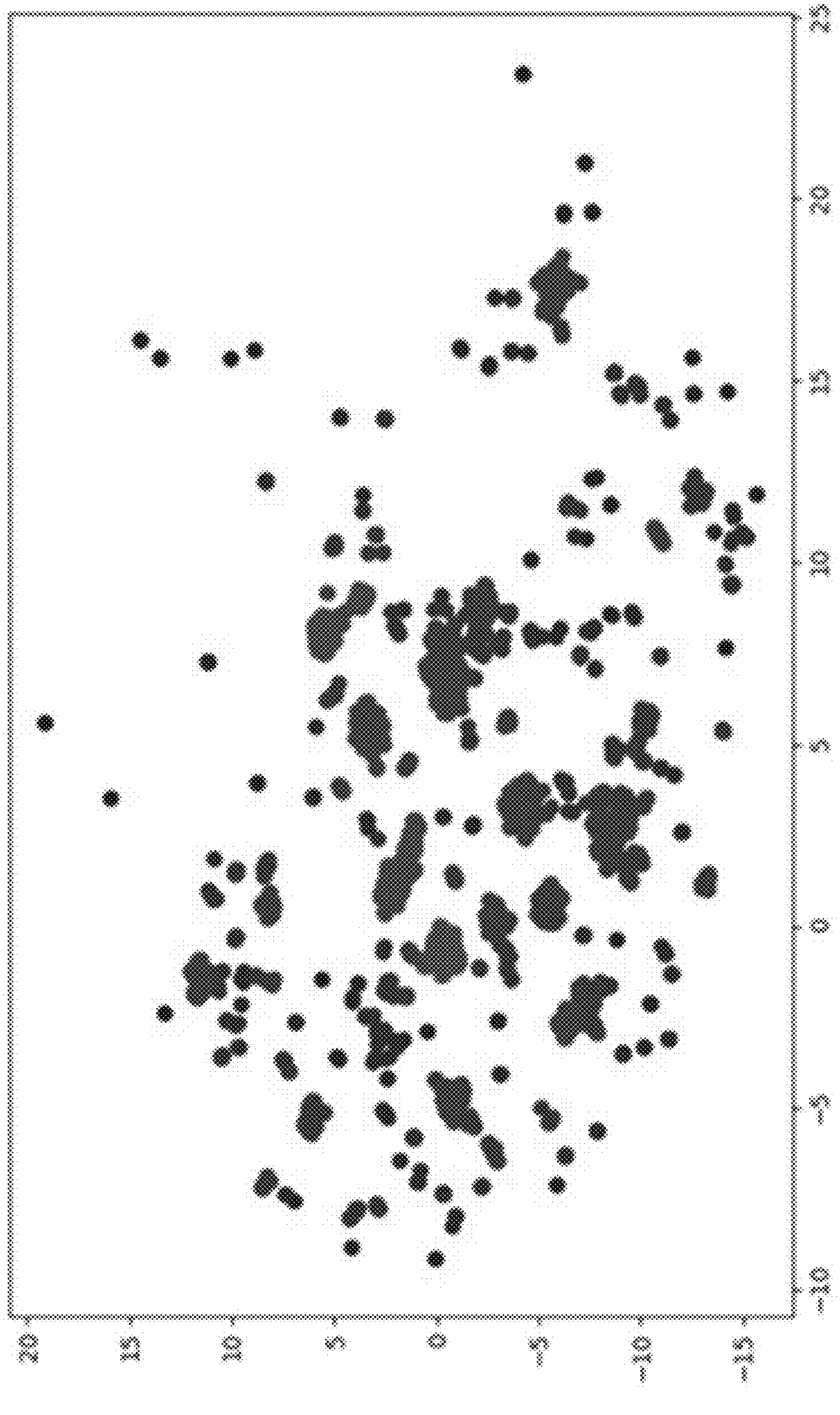
FIG. 22A-FIG. 22G show example 2D probability distributions used for sampling, generated on the interface using different probability distributions, according to some embodiments.
Figure 22B:
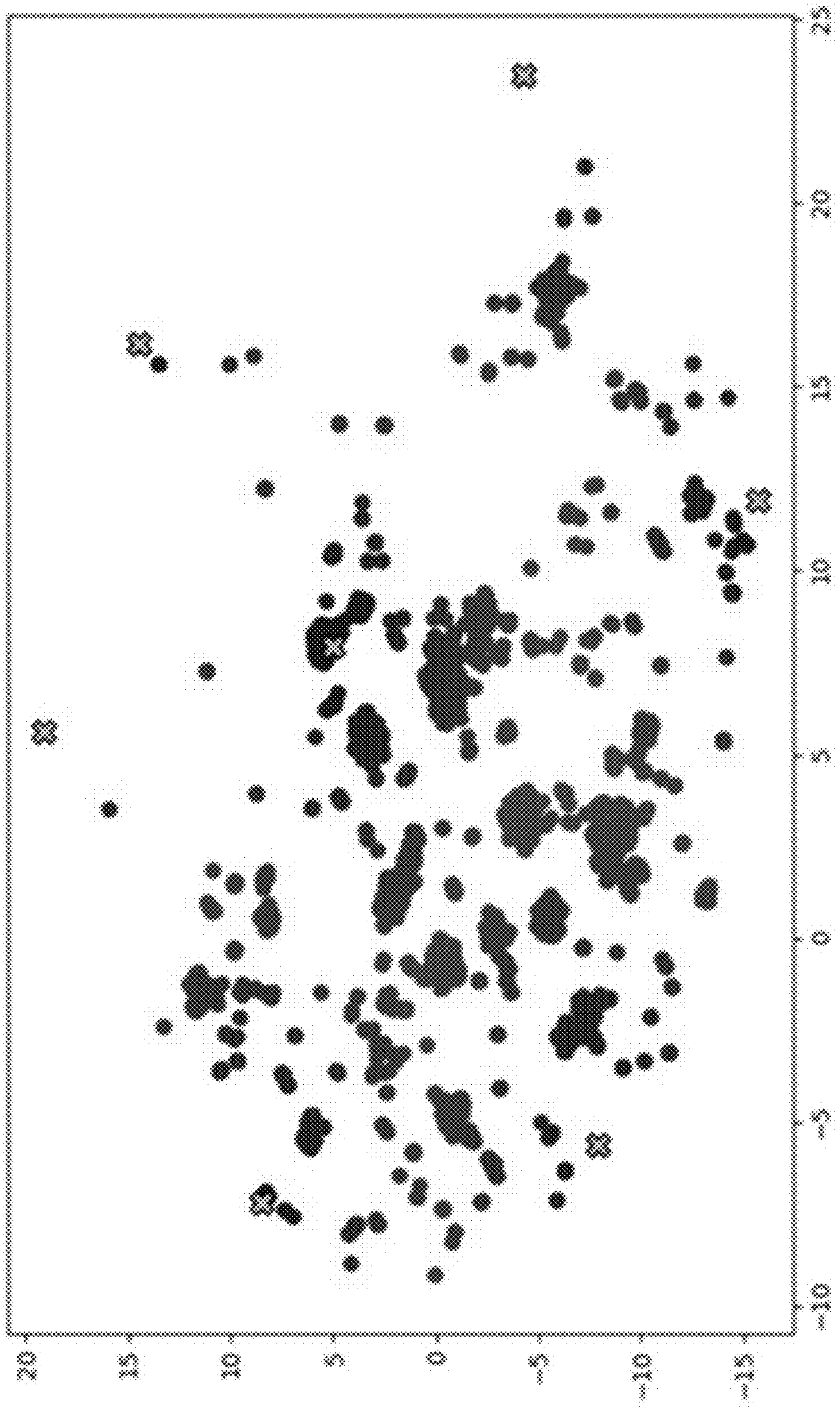
Figure 22C:
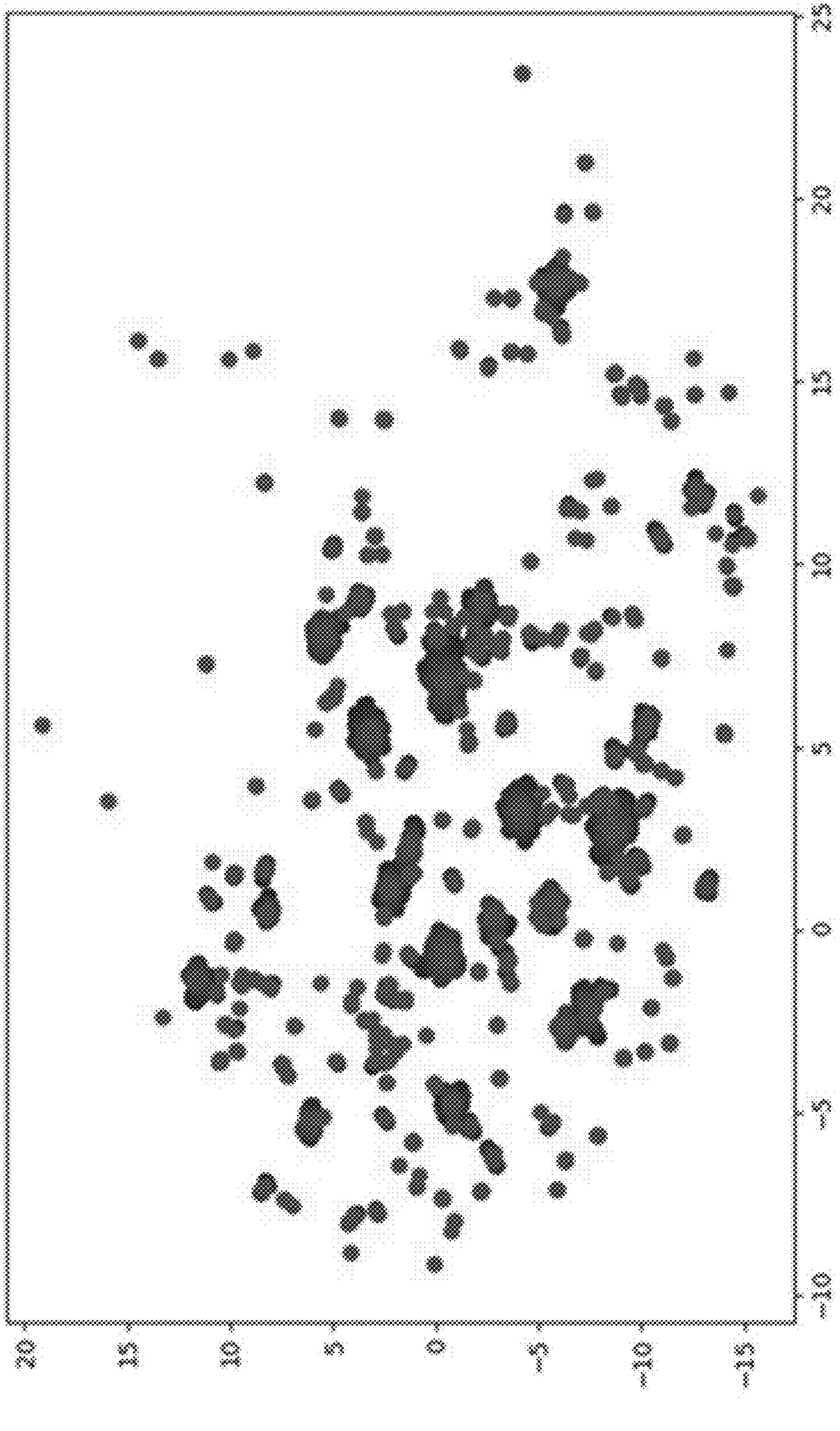
Figure 22D:
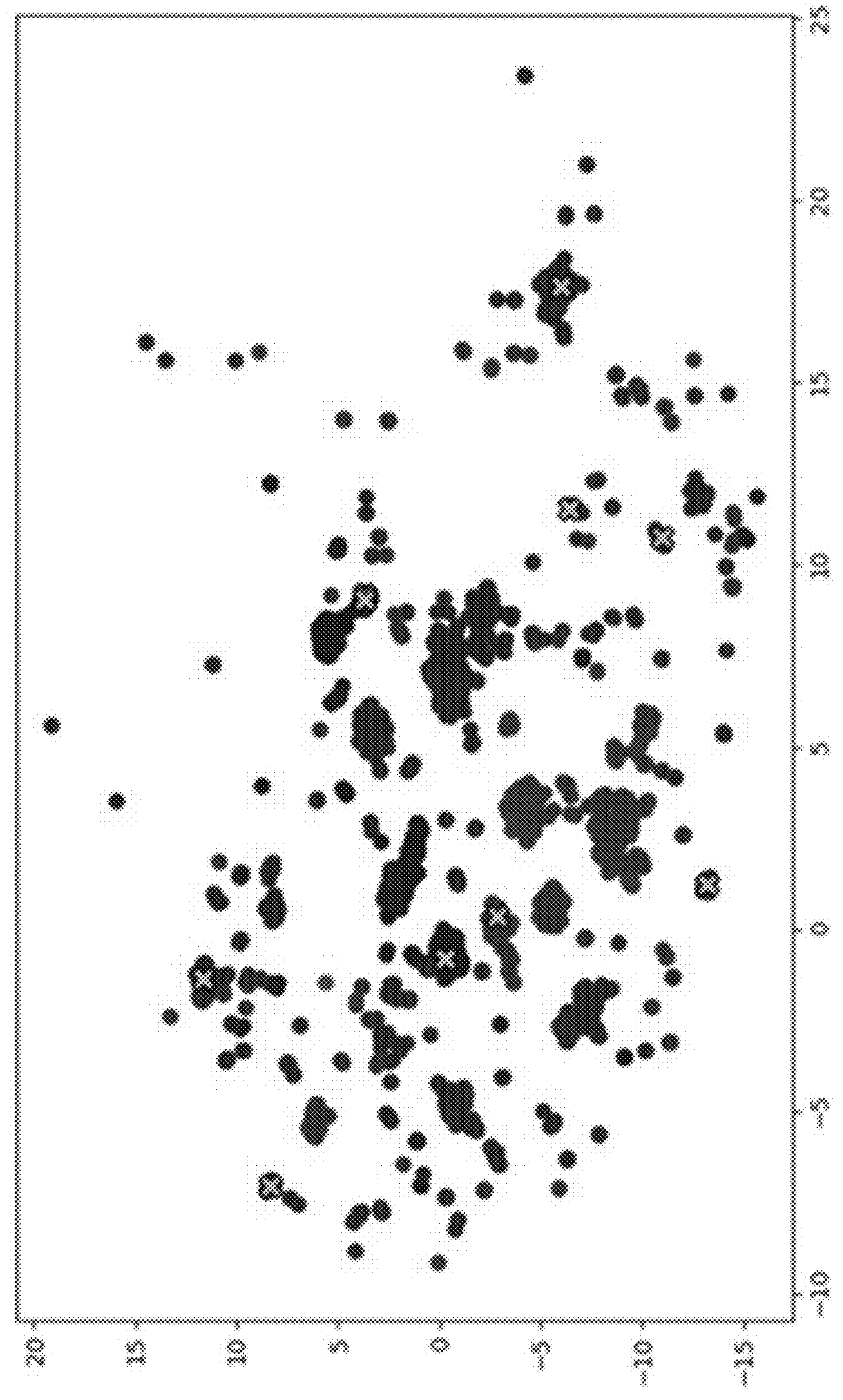
Figure 22E:
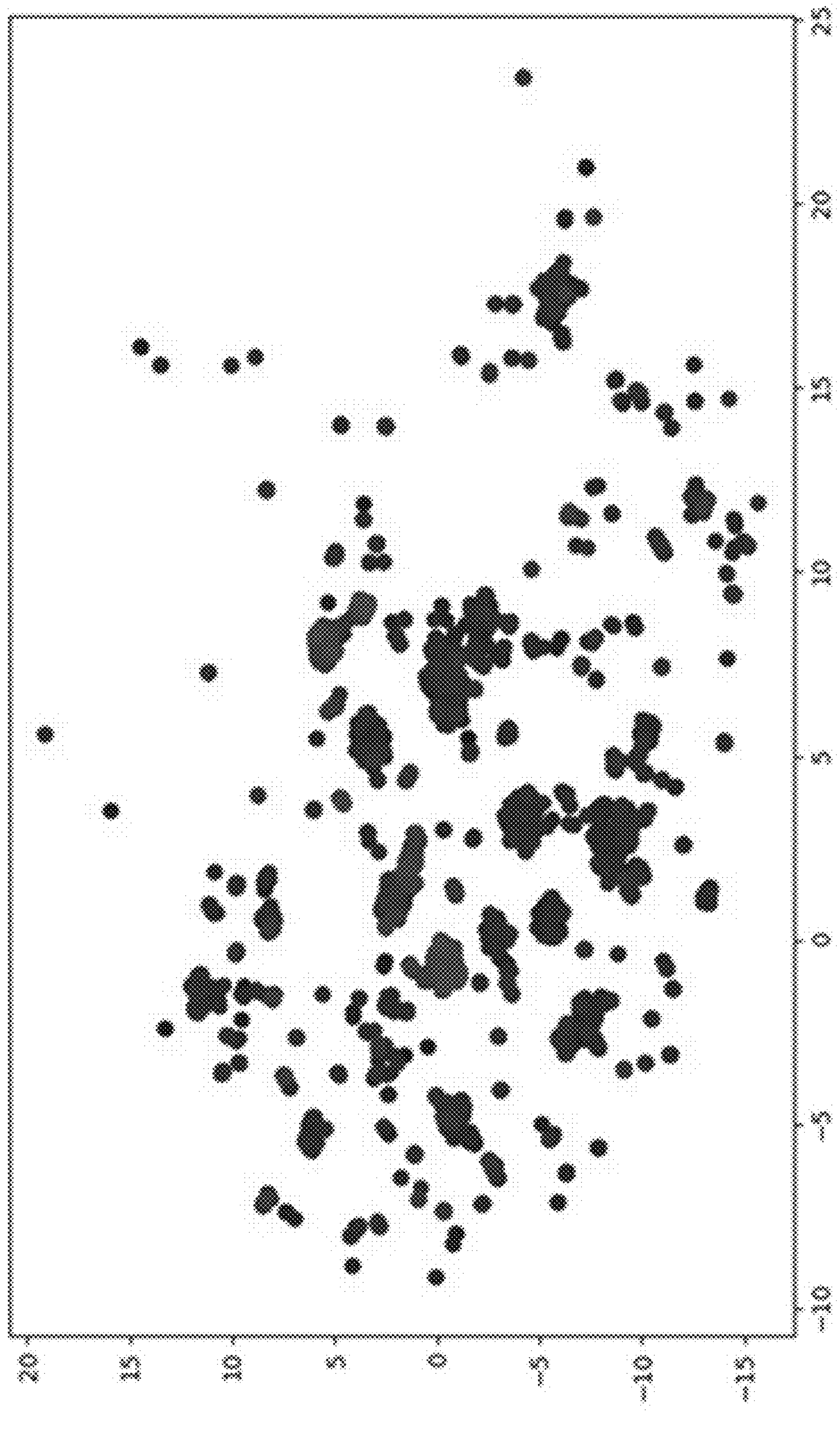
Figure 22F:
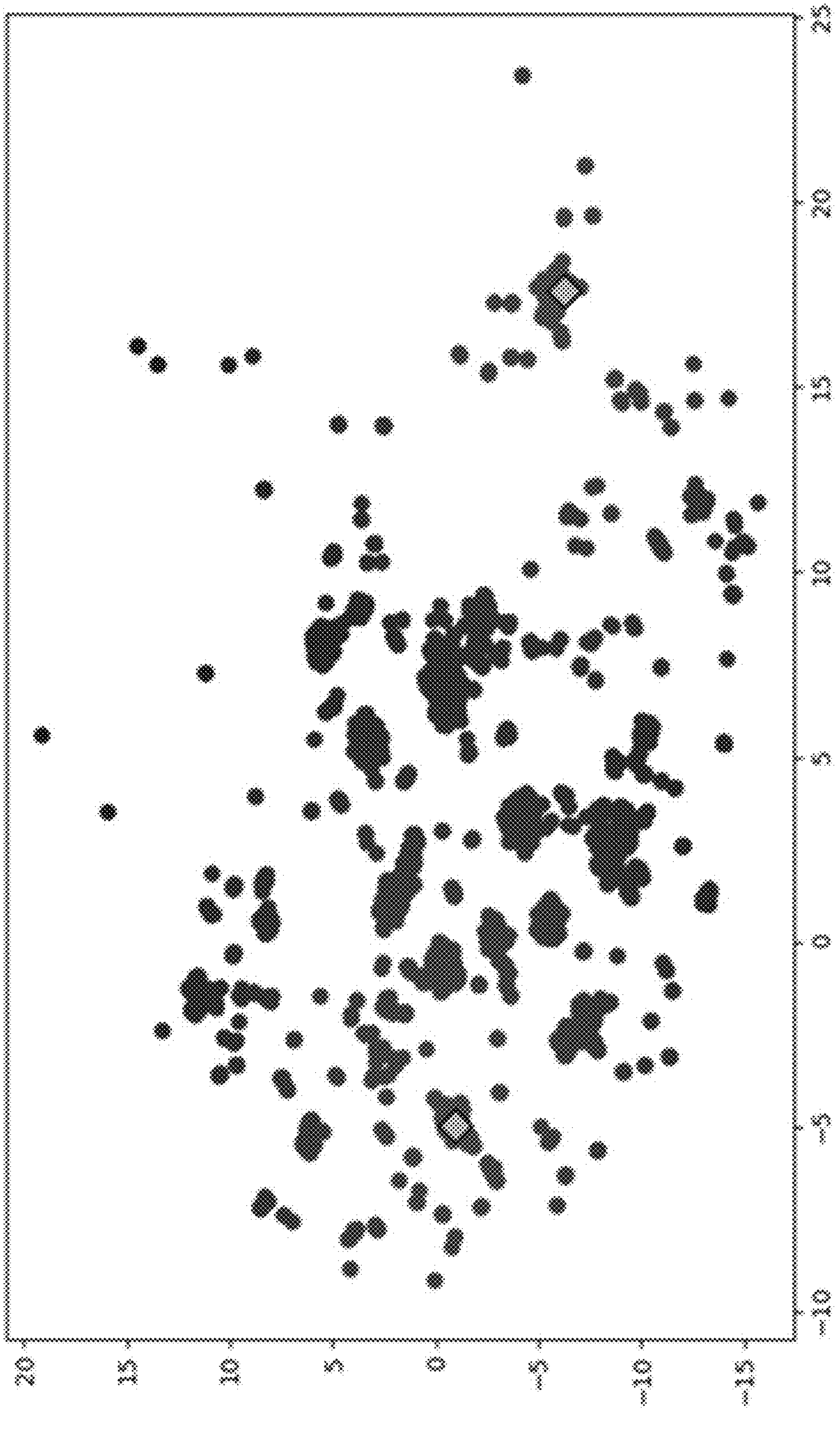
Figure 22G:
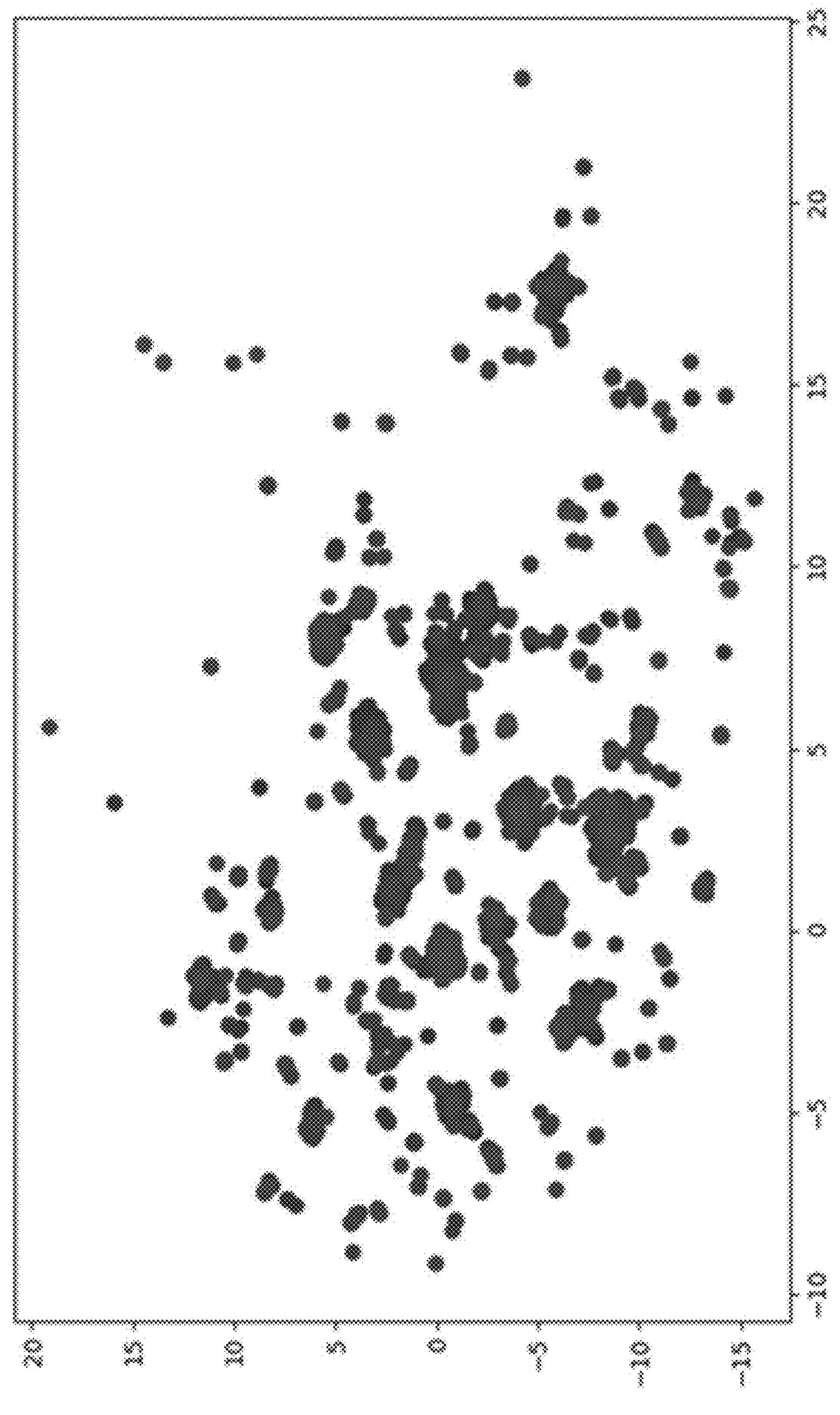

FIG. 22A-FIG. 22G show example 2D probability distributions used for sampling, generated on the same interface using different probability distributions, according to some embodiments. FIG. 22A show an example 2D probability distribution generated on the same interface using the probability distribution for density of clusters, according to some embodiments. FIG. 22B show an example 2D probability distribution generated on the same interface using the probability distribution for diversity of samples, according to some embodiments. FIG. 22C show an example 2D probability distribution generated on the same interface using the probability distribution for proximity to cluster or tile centers, according to some embodiments. FIG. 22D show an example 2D probability distribution generated on the same interface using the probability distribution for diversity of sequence parts, according to some embodiments. FIG. 22E show an example 2D probability distribution generated on the same interface using the probability distribution for input scores, according to some embodiments. FIG. 22F show an example 2D probability distribution generated on the same interface using the probability distribution for proximity to reference(s), according to some embodiments. FIG. 22G show an example 2D probability distribution generated on the same interface using the overall probability of sampling, according to some embodiments.

In another sampling approach, it can be possible to sample molecules using intersection and subtraction of interfaces or layers, introduced before. For example, sampling can be performed on the result of subtraction of a layer or interface from another layer or interface, or samples can be drawn from the intersection of two layers or interfaces.

When molecules are antibodies, intersection and/or subtraction can be used to produce a good set of antibodies to sample from (as described above). A useful implementation of sampling by intersection and subtraction of interfaces or layers can be sampling from immunized library of antibodies from immunized lab animal(s). This can also be a subtraction/intersection of the master interface (which can include several targets). Consider one or multiple unimmunized animals (e.g., lab mice) whose bodies are not injected by the specific target antigen. Also, assume there are one or multiple immunized animals which have been injected the target antigen. Without a need of in-lab panning enrichment, it can be possible to sample antibodies, which may be candidates for being drugs, from the immunized animals. For this, the layer(s) or interface(s) of unimmunized antibodies can be subtracted from the layer(s) or interface(s) of immunized antibodies. Doing this can reduce antibodies non-relevant to the target antigen because what remains after subtraction is expected to be added after injection of the target.

Optionally, it can be possible to consider the intersection of layer(s) or interface(s) after performing subtraction of unimmunized library from immunized library. By doing this, the shared antibodies among multiple animals, after subtraction of unimmunized libraries, can be considered. When an antibody exists, after this subtraction, in multiple animals immunized with the same target antigen, the antibody can have a higher likelihood of binding the target of interest.

When the molecules are proteins, it can also be possible to sample according to the germline genes either by sequence or structure. For example, the antibodies can be categorized into multiple groups where each group has mutated from the same germline gene or the same parental of molecules. Then, any of the above mentioned sampling algorithms can be used where the clusters are the groups of the antibodies mutating from the parentals (e.g., each cluster has the same parent and the diversity between the parentals is considered). For categorizing the antibodies into these groups, the similarity of the antibodies to the parentals can be calculated using any technique such as BLAST (Basic Local Alignment Search Tool) search, BLOSUM (BLOcks SUbstitution Matrix) matrix, PAM (Point Accepted Mutation) matrix, substitution matrix, PSSM (Position-Specific Scoring Matrix), or Hamming distance.

The sampling algorithm can be a combination or ensemble of any of the abovementioned sampling methods. For example, stratified sampling or mosaic sampling can be performed while considering diverse sequence parts. Another example is stratified sampling or mosaic sampling while using probability scores for sampling. In some implementations, stratified sampling can be used while considering distances from cluster or tile centers/representatives as the probability scores for sampling.

Sampling algorithms can also be used back-to-back in a concatenated way. In this concatenation, the next sampling stage can either sample from the samples obtained by the previous stage or adds additional samples. An example of the former can be performing stratified sampling or mosaic sampling followed by drawing samples from the obtained samples using sampling with diverse sequence parts. An example of the latter case can be first stratified sampling from the whole interface of molecules and then sampling additional molecules using another sampling method from the whole interface and combining them to have the total samples.

It can be possible to compare molecules with each other in the interface. For this, either the whole or part(s) of the molecules can be compared to each other in whole or in part. This comparison can be used to compare samples of molecules as well. The comparison can be either equality comparison or measuring their similarity or difference using any technique. If comparison is in terms of structure, their 3D structure can be compared with any technique such as template matching, 3D matching, or any other comparison methods. If comparison is in terms of sequence, different techniques can be used such as BLAST (Basic Local Alignment Search Tool) search, BLOSUM (BLOcks SUbstitution Matrix) matrix, PAM (Point Accepted Mutation) matrix, substitution matrix, PSSM (Position-Specific Scoring Matrix), Hamming distance, or available code libraries. One possible application of this comparison is to compare molecules with other previously characterized molecules to find additional molecules.

After sampling is performed by the user, the interface can also recommend new additional samples which might be of interest or missing in the samples obtained by the already performed sampling. For example, the user may use one sampling technique and then the interface may use an unused sampling technique to generate recommendations.

The user interface 300 (e.g. user interface 400) can have buttons for exporting files (332). Any file(s) can be chosen to be exported. For example, the data 102 or dataset 106 or the drawn samples (214 and 324) or scores (216 and 316) can be exported. Different methods can be used for exporting the files; for example, the files can be downloaded or moved from one to another folder/directory or they can displayed/reported in the user interface by any methods such as tables, visualization, pop-up window, etc.

Additionally, a report can be exported by the interface for the approach of sampling and statistics of the samples. Statistical analysis and visualization of samples can be reported in various formats such as plots, figures, tables, text, and notes.

Figure 4A:
FIGS. 4A, 4B, 4C, 4D, 4E are example map visualizations for user interfaces, in accordance with an embodiment.
Figure 4B:
Figure 4C:
Figure 4D:
Figure 4E:

FIGS. 4A, 4B, 4C, 4D, 4E are example map visualizations 310 for user interfaces 300, 400 in accordance with an embodiment. The map visualizations 310 can visually indicate different layers. FIG. 4A shows layer 1. FIG. 4B shows layer 1 and layer 2. FIG. 4C shows layers 1 and 2, a reference molecule, and a cluster around reference molecule. FIG. 4D shows layers 1 and 2, a reference molecule, a cluster around reference molecule, and sampling from layers 1 and 2. FIG. 4E shows layers 1 and 2 with scores coded by marker size.

The user interface 300 can also report the map not only as a visualization map but also in any format. For example, it can report the map by sound, smelling, or touching. In this way, the user interface can also be useful for the visually impaired users. In some embodiments, the user interface 300 can show the map of molecules as a hologram where the user can walk among the molecules and touch them or interact with them using different gestures. In some other implementations, the user interface 300 can generate different odors for the molecules in the map.

In some embodiments, this odor can also be used for coding scores in the map where every category of score has a different odor or a gradient of odors can be used for a continuous score. In some other embodiments, the user can interface can report the map by sound where the positions of the molecules in the map, as well as their characteristics, are reported by some generated voice. It is also possible to combine reporting by different senses so the user can have various options to explore.

The mapping system 100 can be used for any reason, application, and purpose. For example, it can be used for antibody selection, immune response (either higher or lower response), tracking the size of cluster at subsequent immunization (for vaccine development), correlating cluster(s) with function(s), secondary assays (e.g., binding, signaling, etc.), deimmunizing antigens or antibodies or proteins, finding common group of paratopes for different variations of antigens (e.g., common epitope), evaluating robustness of immune response (more clusters or more diversity of clusters), etc.

The system 100 can be used for different applications and use cases. The following provide example use cases.

Antibody Discovery

The paratope map can be used to efficiently sample antibodies from a library of antibodies. Antibodies may be selected form a single targeted cluster. Selection of multiple antibodies form a single paratope cluster will increase multiple antibodies with similar biophysical features. Antibodies can be selected broadly from multiple clusters to increase the diversity of the biophysical properties of the antibodies sampled.

In some embodiments, the antibodies or antigen binding fragments thereof comprise antibodies from a species including, but not limited to, mice, bovine, rabbits, camels, llamas, humans, alpaca, and standard species.

Humanization

The paratope map contains the original antibody and humanization variants. Antibodies are humanized to increase the human content while conserving the paratope. The paratope map can be used to visualize changes in the paratope unintentionally induced by the humanization process. Humanized variants that are closest to the original antibody on the paratope map have the greatest likelihood of maintaining the binding and functional properties of the original antibody.

Vaccine Development

The paratope map can be used to evaluate the immune response after vaccination. The paratope map can be used to determine and compare the immune response from different vaccine formulations.

In some embodiments, the map can identify the specific binding sites on antibodies for understanding how antibodies neutralize pathogens and for designing effective vaccines and therapies.

Format Conversion

The paratope map can be generated from different antibody formats such as single chain and VH-VL antibodies. A paratope map with multiple types of antibodies will allow for the conversion from one antibody form to another. Antibodies in the same cluster will bind to a common epitope.

Diagnosis or Monitoring

The paratope map could be used to identify and monitor changes in antibody repertoire associated with disease.

In some embodiments, the system 100 can suggest amino acid variation to improve the characteristics of the protein/antibody.

Figure 5:
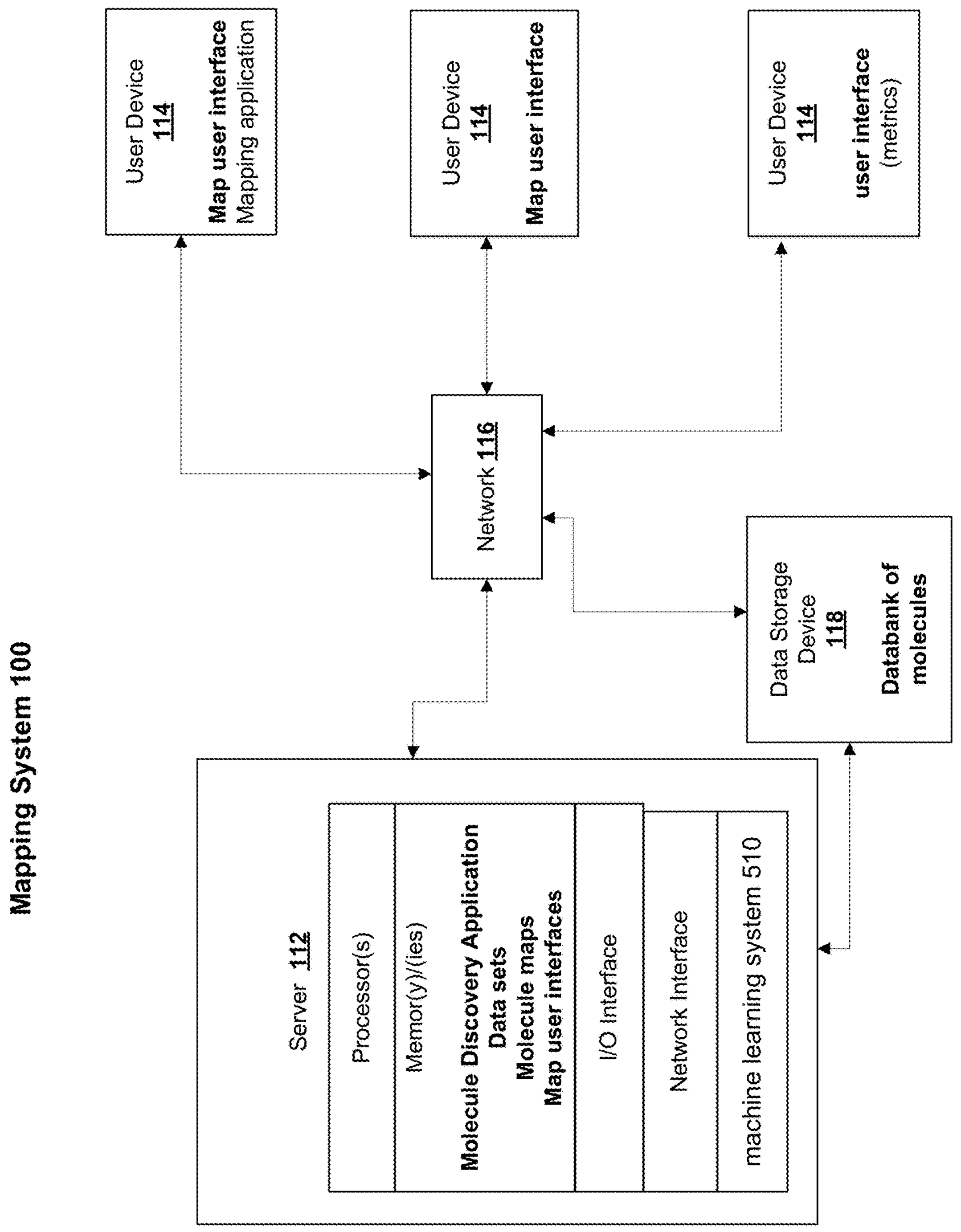
FIG. 5 is a block diagram of another example mapping system, in accordance with an embodiment.

FIG. 5 is another example diagram of mapping system 100 in accordance with an embodiment.

Mapping system 100 maps molecule data into visual interfaces. Mapping system 100 has a processing subsystem that includes one or more processors and one or more memories coupled with the one or more processors. The processing subsystem is configured to cause the mapping system 100 to receive input molecules. The input molecules can be a set or multiple sets of one or more molecules. Each molecule can be defined as a sequence of information. Mapping system 100 can encode the sequence of information. Mapping system 100 can generate a dataset by processing the input molecules. The dataset can include the encoded sequence of information, three-dimensional coordinates of the sequence of information for each molecule to define structure of the molecule, features and fingerprints. Mapping system 100 can transform the dataset to generate a molecule map by feature extraction and fingerprint generation to reduce a higher number of dimensions into lower dimensional data representations that can be visualized while capturing valuable data in the lower-dimensional data representations.

Mapping system 100 can generate a map user interface comprising the molecule map as a visualization of the lower dimensional data representations of the dataset. Mapping system 100 can provide the map user interface to user device 114 via network 116.

Mapping system 100 can be used for mapping proteins, protein-like molecules, or fragments thereof into visual interfaces and generating maps for display and interaction. In some embodiments, the mapping system 100 can be used to map non-protein molecules such as lipids, complex sugars, nucleic acids, etc. The mapping system 100 can include a processing subsystem that includes one or more processors and one or more memories coupled with the one or more processors.

The processing subsystem can be configured to cause the system to receive data (e.g., raw data, preprocessed data, input data, etc.) for a set or multiple sets of one or more input proteins, protein-like molecules, or fragments thereof. Raw data (e.g. source data or primary data) data that has been collected from a source but has not yet been processed, cleaned, or analyzed. Raw data can be unprocessed and in its original state which may contain errors, outliers, or inconsistencies. Raw data can be in a variety of forms, and can include numbers, text, images, audio, or any other type of data. While raw data itself may not be immediately useful, it can hold the potential for valuable insights once it is processed and analyzed.

The data can include features of the one or more proteins, protein-like molecules, or fragments thereof. The data can include features such as sequence, structure, biophysical properties, etc. Features can be individual measurable properties or characteristics that describe the entities, and can be used to analyze these entities (e.g., binding, function, stability, expressibility, affinity, immunogenicity etc.). Features can be considered dimensions of data. Features can be used as input to train a model for machine learning, for example. There can be raw dimensions and extracted dimensions. Features may also include, for example, the primary structure (e.g., the sequence of amino acids in a protein, which determines its unique characteristics and function; this linear sequence is crucial because even a single change can affect the protein's function), secondary structure (e.g., localized folding patterns within a protein, such as alpha-helices and beta-sheets, stabilized by hydrogen bonds, etc.; these structures contribute to the overall shape and stability of the protein), tertiary structure (e.g., the three-dimensional shape of a single polypeptide chain, formed by interactions between the side chains (R groups) of the amino acids; this structure is essential for the protein's functionality and interaction with other molecules), quaternary structure (e.g., the arrangement of multiple polypeptide chains (subunits) in a multi-subunit protein; this structure is important for the function of proteins that operate as complexes, such as hemoglobin), binding sites (e.g., specific regions on the protein where ligands (such as substrates, inhibitors, or other proteins) can bind; these sites are critical for the protein's biological activity and interactions), Post-Translational Modifications (PTMs) (e.g., chemical modifications that occur after protein synthesis, such as phosphorylation, glycosylation, and ubiquitination; PTMs can alter the protein's function, localization, and interactions), Hydrophobicity and Hydrophilicity (e.g., the distribution of hydrophobic (water-repelling) and hydrophilic (water-attracting) regions within a protein; this feature influences the protein's folding, stability, and interactions with other molecules), molecular weight (e.g., the mass of the protein, which can affect its mobility in techniques like gel electrophoresis and its behavior in solution), isoelectric point (pI) (e.g., the pH at which the protein carries no net charge; this property is important for protein purification and characterization techniques), functional domains (e.g., specific regions of the protein that have distinct functional roles, such as DNA-binding domains, catalytic domains, or transmembrane regions; these domains are often conserved across different proteins with similar functions), etc.

The processing subsystem can be configured to cause the system to generate at least one dataset by processing the data for the set or multiple sets of the one or more input proteins, protein-like molecules, or fragments thereof. Processing can involve cleaning, organizing, and transforming the data into a more usable format. In some embodiments, the processing may include steps to filter the data or remove errors, outliers, or inconsistencies.

The processing subsystem can be configured to cause the system to transform one or more of the data and the at least one dataset(s) to generate a map (e.g., a representation of a space that associates protein-like molecules or fragments within the space according to one or more models or clusters) and additional features by feature extraction (e.g., transforming raw data into informative features), feature selection (e.g., identifying the most relevant features for the model), or feature creation (e.g., creating new features from existing ones, such as combining or splitting features) to reduce higher dimensional data representations into lower dimensional data representations that can be depicted and/or visualized by the visual interface while capturing valuable information in the lower-dimensional data representations.

High-dimensional data can be challenging to visualize, and the transformed lower dimensional representation can make the data easier to interpret and present. The lower dimensional data representation may improve use of computer and network resources, as it may be reduced size for transmission, more efficient for interface to handle and render, improve memory usage at display device, and so on. By reducing the number of features, dimensional reduction can decrease the computational resources required for data processing and analysis. By eliminating redundant and irrelevant features, dimensional reduction can help reduce noise in the data. This can lead to more accurate and robust data representations. This may also improve data analysis by making it easier to identify and focus on the most significant variables, simplifying the analysis and interpretation of complex datasets. The user interface can be displayed on devices with different screen sizes and resolutions, which can impact visualizations rendered within the interface. The transformed representations can help improve UI performance for these complex datasets.

Dimensionality reduction can reduce the number of input variables or features in a dataset while preserving relevant information. This process can help in simplifying models, reducing computation time, and improving the performance. Example types of dimensionality reduction techniques include feature selection (selecting a subset of features) and feature extraction (transforming data into a lower-dimensional space). Features can also be considered dimensions of data. Extracting or selecting features can be a reduction of dimensions. Some example condierations for feature reduction can include, for example:

- Choosing the Right Method: Selecting an appropriate dimensionality reduction technique based on the nature of the data and the specific analysis goals is important. For example, Principal Component Analysis (PCA) is often used for its ability to retain variance, while t-SNE is useful for preserving local structures;
- Balancing Dimensionality and Information: The goal is to reduce dimensions while retaining the most significant features. Techniques like PCA transform the data into a new set of variables (principal components) that capture the maximum variance, ensuring that the most informative aspects of the data are preserved;
- Regularization and Supervised Methods: Methods such as Linear Discriminant Analysis (LDA) and Partial Least Squares (PLS) use class labels to maintain relevant information related to specific outcomes or classifications. These supervised techniques ensure that the reduced dimensions still reflect the important biological signals;

Combining Multiple Techniques: Sometimes, combining dimensionality reduction with other methods like transfer learning can enhance the robustness and interpretability of the data. For instance, autoencoders can be used to learn a compact representation of the data, which can then be fine-tuned with additional data to improve performance; and Validation and Cross-Validation: Regularly validating the reduced data against independent datasets helps ensure that the dimensionality reduction process has not discarded critical information. Cross-validation techniques can also be used to assess the stability and reliability of the reduced dimensions.

The lower dimensional data representations can include one or more clusters of proteins, protein-like molecules, or fragments thereof. The proteins, protein-like molecules, or fragments thereof can include the one or more input proteins, protein-like molecules, or fragments thereof or newly generated proteins, protein-like molecules, or fragments thereof. Clusters refer to groups of proteins, protein-like molecules, or fragments thereof (and related data elements) that are "similar" to each other within a dataset. A data cluster can be a subpopulation of a larger dataset where each data point is closer to the cluster center than to other cluster centers. This closeness can be determined by minimizing the squared distances between data points and their respective cluster centers. Clustering helps in identifying patterns, trends, and relationships within the data. By using clustering techniques, mapping system 100 can simplify complex datasets and uncover hidden structures that may not be immediately apparent. Types of clustering methods include: K-Means Clustering (which partitions the data into (k) clusters by minimizing the distance between data points and the cluster centroids), Hierarchical Clustering (which builds a tree of clusters by either merging or splitting existing clusters based on their proximity), Density-Based Clustering (DBSCAN) (which forms clusters based on the density of data points, identifying areas of high density as clusters and areas of low density as noise), etc.

The processing subsystem can be configured to cause the system to generate a visual map interface including the map as a visual representation of the lower dimensional data representations of the dataset. The visual representation can include visualizations representing the dataset as one or more layers of proteins, protein-like molecules, or fragments thereof, each layer including one or more of the one or more clusters of proteins, protein-like molecules, or fragments thereof. Layers can be used to organize and display different data points for proteins, protein-like molecules, or fragments thereof on the map. Each layer can represent a specific set of data, and multiple layers can be superimposed to combine different sets and generate different visualizations. The map can have a base layer and data layers that overlap additional data on top of the base layer. The layers can be interactive, and clicking on features or data points may result in processing or filtering or display more/less data. Layers can be superimposed onto one another, (e.g., like layer addition). Map generation or analysis can include generating clusters, arranging embeddings in clusters, layer-wise embedding, embedding individual molecules, sampling from the map, or coding scores in the map. Typically the map is generated then clusters are generated (e.g., in order to detect the cluster need to cluster the data). The map can contain the clusters and visualizes the clusters.

The processing subsystem can be configured to cause the system to provide the visual map interface with tools for interaction with the map and inspection, searching, sampling, clustering and analysis of the one or more proteins, protein-like molecules, or fragments thereof or newly generated proteins, protein-like molecules, or fragments thereof. This may aide in prospective decision-making as the tools can be used to interact with the data prospectively. The tools may include, for example, UI tools. UI tools are specialized software applications that help create, modify, and explore the visual map interfaces.

The processing subsystem can be configured to cause the system to receive commands or detect interactions with the map by the tools at the visual map interface, update the map based on the commands or interactions, and cause the mapping system 100 to trigger an update to the visual map interface with the updated map.

In some embodiments, the input molecules are proteins or protein-like molecules comprising antibodies and antigens. For example, the antibodies are of a species including, but not limited to, mice, bovine, rabbits, camels, llamas, humans, alpaca, and standard species.

In some embodiments, the input molecules are antibodies and antigens, and wherein the molecule map is a paratope map. In some embodiments, the input molecules are antigens, and wherein the molecule map is an epitope map.

In some embodiments, the processing subsystem (e.g. server 112) extracts features and generates fingerprints using machine learning or statistical methods involving one or more of dimensionality reduction, a reconstruction autoencoder, a variational autoencoder, adversarial autoencoder, neural networks, graph neural networks, attention networks, and recurrent networks.

In some embodiments, system 100 has a data storage device of a databank of molecules 118, wherein each molecule is assigned a unique index.

In some embodiments, the system 100 compares a molecule to the bank of molecules 118 and assigns the molecule to an index of a closest molecule in the bank of molecules, wherein molecules assigned to the same index have similar sequences, structures, or properties.

In some embodiments, the feature extraction is performed using layer-wise embedding, wherein, for multiple datasets or multiple parts of a dataset, features of each of the multiple datasets or each of the multiple parts of the dataset are extracted separately. In some embodiments, the features can be plotted as layers of visualization on top of each other. In some embodiments, the map user interface includes the visualization of the dataset and also has control inputs to enable viewing of the layers separately or in relation to other layers. In some embodiments, one or more layers are used for training for the feature extraction, and one or more other layers are used for testing the feature extraction.

In some embodiments, the system 100 has a user device 114 to display the map user interface. In some embodiments, the map user interface at user device 114 includes a visualization of extracted features of the dataset. In some embodiments, the map user interface is one-dimensional, two-dimensional, three-dimensional, four-dimensional, or higher dimensional. In some embodiments, embeddings of the layer-wise embedding change over time as a time-series, and wherein the map user interface comprises three-dimensional embeddings changing over the time as the time-series representing four-dimensional embeddings. In some embodiments, the map user interface comprises a visualization of clusters around molecules of interest. In some embodiments, the map user interface comprises one or more clusters of molecules. In some embodiments, the layer-wise embedding comprises individual molecule embeddings.

In some embodiments, the server 112 performs feature extraction for individual molecules of the dataset to obtain individual molecule embeddings.

FIG. 5 shows a network diagram depicting a network environment of a mapping system 100 and a machine learning system 510, and a plurality of user devices 104, interconnected by a communication network 116, in accordance with an embodiment. These systems and devices cooperate in manners disclosed herein for mapping molecules into visual interfaces. Each user device 114 is a device operable by a user to interact with a mapping application provided by system 100.

The server 112 and mapping application can provide one or more interactive user interfaces, accessible by a user operating a user device 114. The interactive user interfaces provided at user device 114 include a user interface for the user to provide input.

Machine learning system 510 is configured to implement various machine learning processes. Machine learning system 510 can generate a dataset by processing the input molecules. The dataset can include an encoded sequence of information, three-dimensional coordinates of the sequence of information for each molecule to define structure of the molecule, features, and fingerprints. Machine learning system 510 can transform the dataset to generate a molecule map by feature extraction and fingerprint generation to reduce a higher number of dimensions into lower dimensional data representations that can be visualized while capturing valuable data in the lower dimensional data representations.

In some embodiments, the machine learning system 510 extracts features and generates fingerprints using machine learning or statistical methods involving one or more of dimensionality reduction, a reconstruction autoencoder, a variational autoencoder, an adversarial autoencoder, neural networks, graph neural networks, attention networks, and recurrent networks.

In some embodiments, system 100 has a data storage device of a databank of molecules 118, wherein each molecule is assigned a unique index. In some embodiments, the machine learning system 510 compares a molecule to the bank of molecules 119 and assigns the molecule to an index of a closest or most similar molecule in the bank of molecules, wherein molecules assigned to the same index have similar sequences, structures or properties.

In some embodiments, machine learning system 510 performs feature extraction using layer-wise embedding, wherein, for multiple datasets or multiple parts of a dataset, features of each of the multiple datasets or each of the multiple parts of the dataset are extracted separately. In some embodiments, the features can be plotted as layers of visualization on top of each other. In some embodiments, the map user interface includes the visualization of the dataset and also has control inputs to enable viewing of the layers separately or in relation to other layers. In some embodiments, one or more layers are used for training for the feature extraction, and one or more other layers are used for testing the feature extraction. In some embodiments, the layer-wise embedding comprises individual molecule embeddings.

In some embodiments, machine learning system 510 performs feature extraction for individual molecules of the dataset to obtain individual molecule embeddings.

Figure 6:
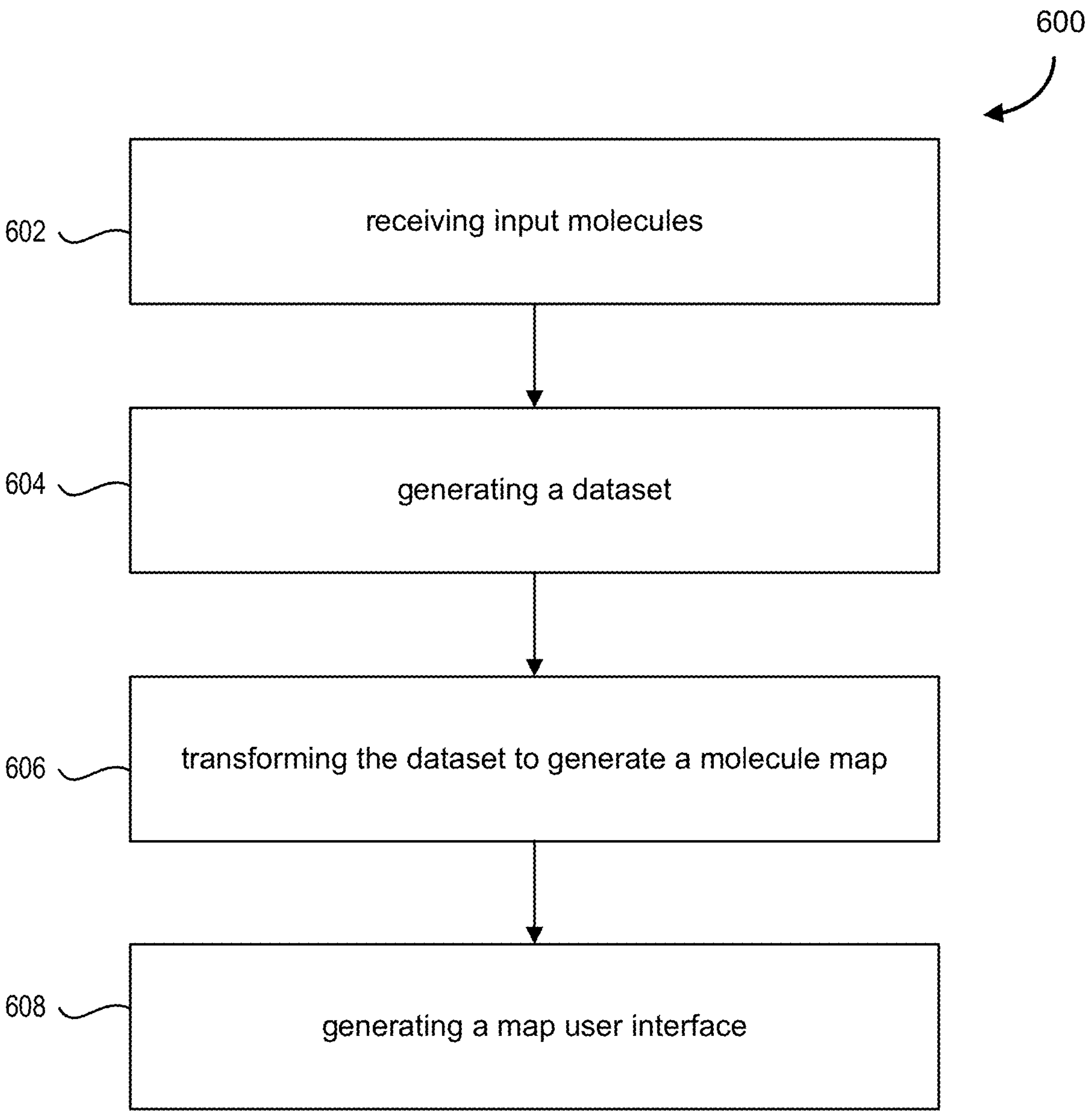
FIG. 6 is a flow diagram of an example method for mapping molecules into visual interfaces, in accordance with an embodiment.

FIG. 6 is a flow diagram of an example method 600 for mapping molecules into visual interfaces, in accordance with an embodiment. In some embodiments, the method 600 involves using the mapping system 100 to map molecule data into visual interfaces. In some embodiments, method 600 is a computer-implemented method for mapping molecules into visual interfaces. The embodiments provide improved visualizations of molecule data. For example, the visualizations can provide visual identifiers for molecule data. The visualizations can provide clusters of similar molecules. The interface is interactive to update the visualizations in response to commands. In some embodiments, method 600 involves a non-transitory computer-readable medium or media having stored thereon machine interpretable instructions which, when executed by a mapping system 100, cause the mapping system 100 to perform the method 600 for mapping molecules into visual interfaces.

At 602, mapping system 100 receives input molecules. Mapping system 100 is configured to receive input molecules data 102. The input molecules can be a set or multiple sets of one or more molecules. Each molecule can be defined as a sequence of information. In some embodiments, the input molecules are proteins or protein-like molecules comprising antibodies and antigens. The antibodies comprise antibodies of a species including, but not limited to, mice, bovine, rabbits, camels, llamas, humans, alpaca and standard species.

The input molecules data 102 can be from any source. Some or all parts of the input molecules data 102 can be in other formats. Moreover, biophysical properties of all origins-high volume data can be used as part of the input molecules. These properties include, but are not limited to, pH, hydrophobicity and hydrophilicity, negative and positive charges, and solvent exposure. Parts of the input molecules data 102 can also be obtained from sequencing methods of nucleic acids. The input molecules data 102 can also go under some preparation and preprocessing steps, such as transformations.

Mapping system 100 encodes the sequence of information in each input molecule. Every molecule can be considered by mapping system 100 as a sequence of information. For example, if the molecule is a protein, mapping system 100 can model the molecule as a sequence of amino acids. The model can have multiple dimensions of data for the molecule. The sequence of information can also be used for dataset generation. Different encoding methods can be used to encode the sequence of information.

At 604, mapping system 100 generates a dataset 106 by processing the input molecules data 102. The dataset 106 comprises the encoded sequence of information, three-dimensional coordinates of the sequence of information for each molecule to define structure of the molecule.

The three-dimensional coordinates of the atoms of every input molecule can be considered as part of the features of the dataset 106. The three-dimensional coordinates of the atoms contain the information of structure of the molecule. The extracted features from the input molecules data 102 can be used to prepare the dataset 106. For example, the sequence of information encoding, three-dimensional coordinates of the sequence, and other properties, including, but not limited to, solvent exposure, hydrophobicity, and charge can be used as the features of dataset 106.

At 606, mapping system 100 transforms the dataset 106 to generate a molecule map 200 by feature extraction and fingerprint generation. This transformation can be any linear or nonlinear transformation. Fingerprints can be extracted out of the above-mentioned raw dataset. In some embodiments, mapping system 100 can extract features and generate fingerprints using machine learning or statistical methods involving one or more of dimensionality reduction, a reconstruction autoencoder, a variational autoencoder, an adversarial autoencoder, neural networks, graph neural networks, attention networks, and recurrent networks. If a machine learning algorithm is used, any algorithm, whether unsupervised, or supervised, or semi-supervised, can be used. The mapping system 100 can use one or more of dimensionality reduction methods to generate data for the improved visualization of interface.

In some embodiments, mapping system 100 generates a paratope map from input molecules data 102 that comprises of antibodies and antigens. In some embodiments, mapping system 100 generates an epitope map from input molecules data 102 that comprises of antigens.

In some embodiments, feature extraction can be performed layer-wise using layer-wise embedding 202. In layer-wise embedding 202, there can be multiple datasets or multiple parts of a dataset where the features of every dataset or every part of the dataset are extracted separately. In some embodiments, the layer-wise embedding comprises individual molecule embeddings. The mapping system 100 can perform feature extraction for individual molecules of the dataset 106 to obtain individual molecule embeddings.

In some embodiments, the features are used for visualization and can be plotted as layers of visualization on top of each other. In some embodiments, one or more layers are used for training for the feature extraction, and one or more other layers are used for testing the feature extraction.

In some embodiments, mapping system 100 can use dimensionality reduction to process the dataset 106. Mapping system 100 can use dimensionality reduction to reduce data with a higher number of dimensions into lower dimensional data representations that can be visualized while capturing valuable data relationships in the lower-dimensional data representations.

In some embodiments, mapping system 100 can comprise a data storage device of a databank of molecules, where each molecule is assigned a unique index. Molecules assigned to the same index have similar sequences, structures or properties. The mapping system 100 can compare a molecule to the bank of molecules and assign the molecule to an index of a closest or most similar molecule in the bank of molecules.

In some embodiments, at 608, mapping system 100 generates a map user interface 300 comprising the molecule map 200 as a visualization of the lower dimensional data representations and extracted features of the dataset 106 The user interface can be of any type of interface or platform. It can be implemented as a stand-alone visualization, a web-based platform, a computer program, an execution (.exe) file, a portable file, or a mobile application. It can be run in any platform, any operating system, or any server.

In some embodiments, the map user interface 300 is one-dimensional, two-dimensional, three-dimensional, four-dimensional, or higher dimensional. In some embodiments, embeddings of the layer-wise embedding 202 change over time as a time-series. In some embodiments, three-dimensional embeddings can be changing over time as the time-series representing four-dimensional embeddings.

In some embodiments, the user interface 300 can have any types of buttons, including but not limited to, regular buttons, radio buttons, check boxes, pop-up menus, tables, sweeping bars, browse buttons, upload and download buttons, submit buttons, running buttons, zoom and move buttons, selection options, and visualization windows. In some embodiments, the user interface 300 comprising the visualization of the dataset 106 has control inputs to enable viewing of the layers separately or in relation to other layers. The user interface 300 can have buttons for adding and removing layers of the embedding 302. The layers can be moved up and down by the user to change the order of layers, and the layers later in the order will be visualized on top of the previous layers. Every layer can be hidden or displayed by the user. The user interface 300 can have a window for visualization of the map 310 and buttons for zooming in or out 312 in the visualization window 310.

In some embodiments, the map user interface comprises a visualization of clusters around molecules of interest. In some embodiments, the map user interface comprises one or more clusters of molecules. The user interface 300 can have buttons for adding or removing individual molecules of interest 306. The user interface 300 can have settings, buttons, and pop-up menus for selecting clusters around individual molecules of interest 318, such as reference or target molecules. The user can select the shape of the cluster and the size of the cluster along every dimension. The user can also choose the location of the individual molecule of interest in the cluster. The user can have the option to choose multiple molecules of interest. The visualization can indicate clusters which can contain molecules of interest. Molecule visual elements can have cluster(s) around.

FIG. 7 is a schematic diagram of computing device 700 which may be used to implement various elements of infrastructure system 100, machine learning system 210. In another example, computing device 700 may be used to implement a user device 114. As depicted, computing device 700 includes at least one processor 702, memory 704, at least one I/O interface 706, and at least one network interface 708.

Each processor 702 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory 704 may include a suitable combination of any type of computer memory that is located either internally or externally such as, for example, random-access memory (RAM), read-only memory (ROM), compact disc read-only memory (CDROM), electro-optical memory, magneto-optical memory, 700 erasable programmable read-only memory (EPROM), and electrically-erasable programmable read-only memory (EEPROM), Ferroelectric RAM (FRAM) or the like.

Each I/O interface 706 enables computing device 700 to interconnect with one or more input devices, such as a keyboard, mouse, camera, touch screen and a microphone, or with one or more output devices such as a display screen and a speaker.

Each network interface 708 enables computing device 700 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

For simplicity only, one computing device 700 is shown but one or both of system 100 and system 210 may include multiple computing devices 700. The computing devices may be the same or different types of devices. The computing devices 700 may be connected in various ways including directly coupled, indirectly coupled via a network, and distributed over a wide geographic area and connected via a network (which may be referred to as "cloud computing").

For example, and without limitation, a computing device 700 may be a server, network appliance, embedded device, computer expansion module, personal computer, laptop, smartphone device, or any other computing device capable of being configured to carry out the methods described herein.

Figure 8:
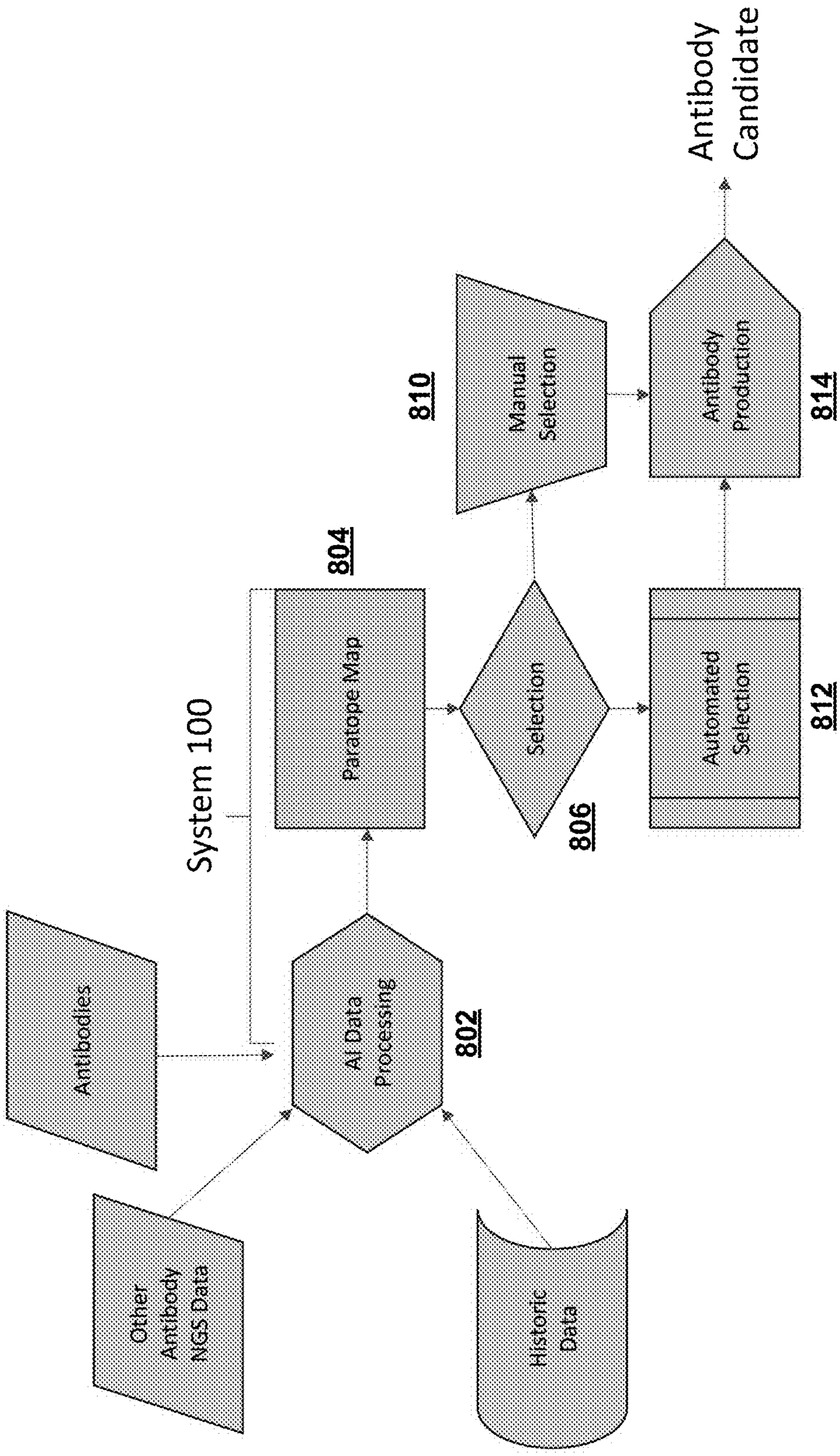
FIG. 8 is a flow diagram of another example method for mapping molecules into visual interfaces, in accordance with an embodiment.

FIG. 8 is a flow diagram of another example method 800 for mapping molecules into visual interfaces, in accordance with an embodiment. At 802, system 100 receives input from different sources. System 100 processes the data to generate a dataset 106, for example. At 804, system generates a paratope map. At 806, system 100 receives selection of one or more molecules or data points on the map. At 810, the system 100 can receive manual selection from control commands received from the visualizations. At 812, the system 100 can receive commands that are automatically generated using machine learning and prediction. At 814, manufacture is generated based on the selected molecule, which is referred to as an antibody in this example process.

FIG. 9 is a schematic diagram of an example representation of antibodies in a paratope map. FIG. 10 is an example schematic diagram of data processing showing features of parts of antibody concatenated together to have a total feature for the antibody. The example visualizations are for antibodies. Other molecules can also be represented by visualizations.

Figure 11:
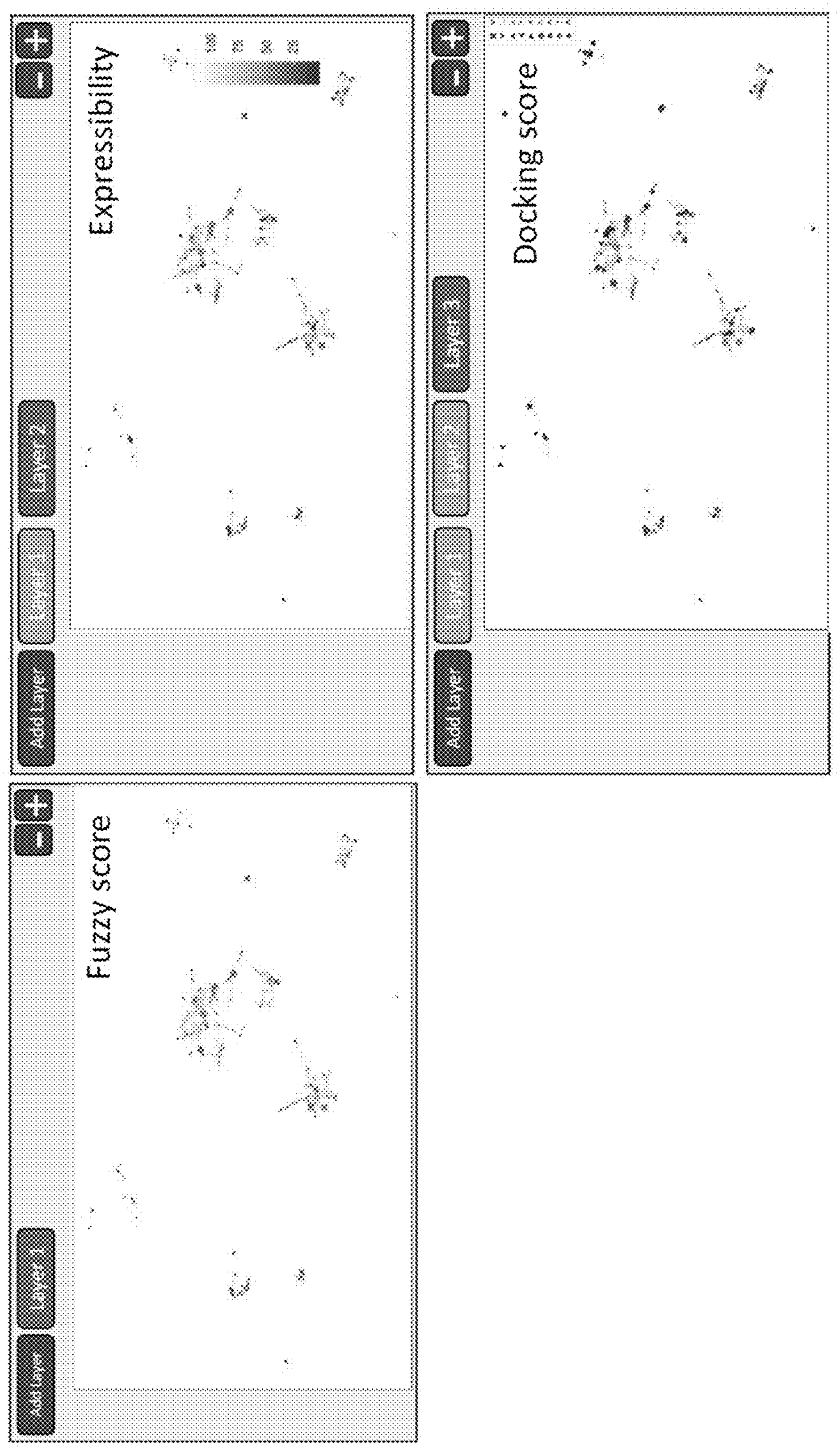
FIG. 11 is a diagram of an example map user interface, in accordance with an embodiment.

FIG. 11 is a diagram of an example map user interface, in accordance with an embodiment. The interface has buttons to provide control commands to visualize different layers for the map. The visualization can also depict different scores or metrics for the molecules.

Figure 12:
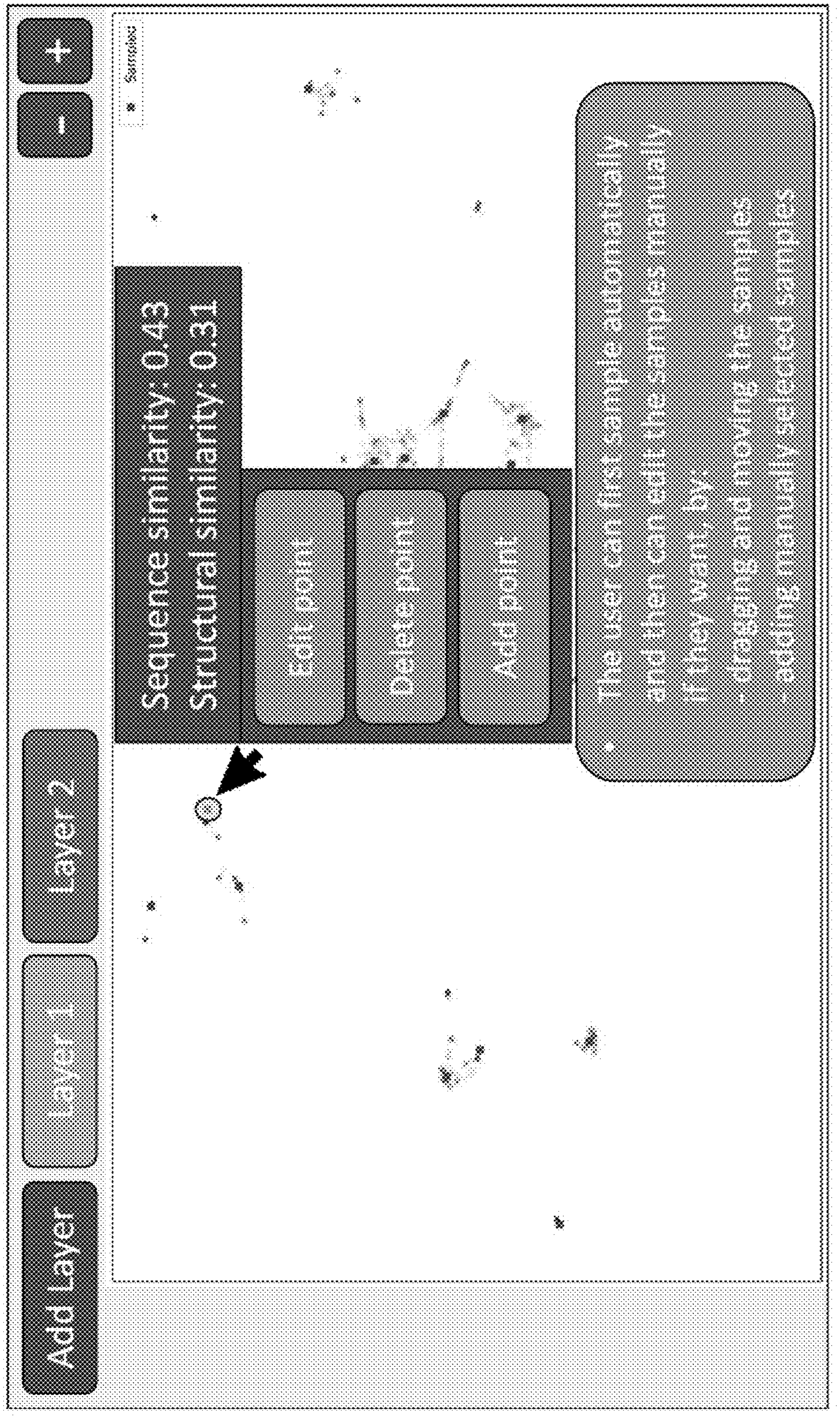
FIG. 12 is a diagram of another example map user interface for samples, in accordance with an embodiment.

FIG. 12 is a diagram of another example map user interface for samples, in accordance with an embodiment. The example interface shows different tools to select points, edit points, delete points, or add points to the map visualization. The interface can be used for samples.

Figure 13:
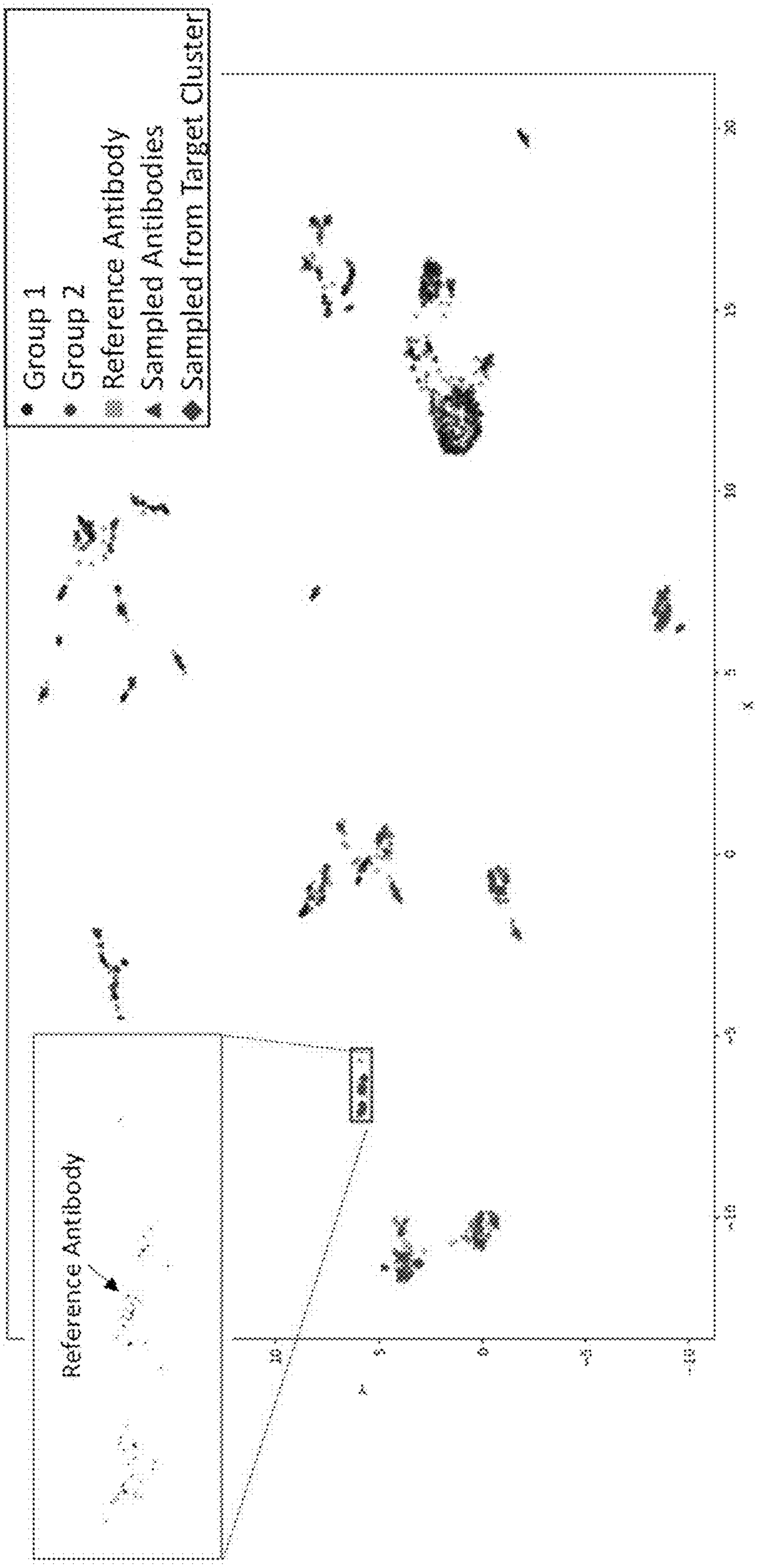
FIG. 13 is a diagram of another example map user interface to select candidate antibodies, in accordance with an embodiment.

FIG. 13 is a diagram of another example map user interface to select candidate antibodies, in accordance with an embodiment. The example interface shows a selection of a reference antibody and its associated cluster. The interface shows different groups of molecules and reference antibodies. The interface also shows sampled antibodies.

Figure 14:
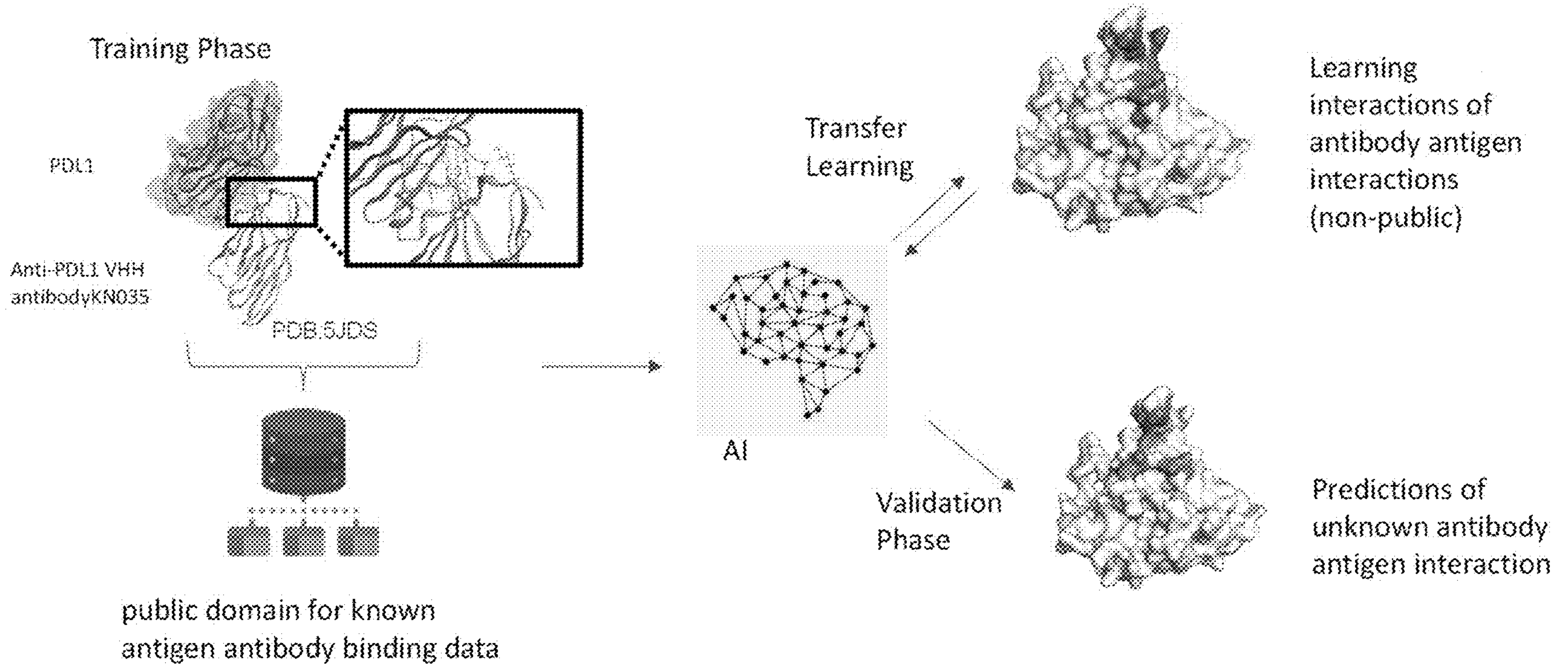
FIG. 14 is a flow diagram for prediction of antibody antigen interactions.

FIG. 14 is a flow diagram for prediction of antibody antigen interactions. The diagram illustrates an example method for molecule mapping. The process can include a training phase, transfer learning and validation phase. The process can generate predications and learning results.

Figure 15:
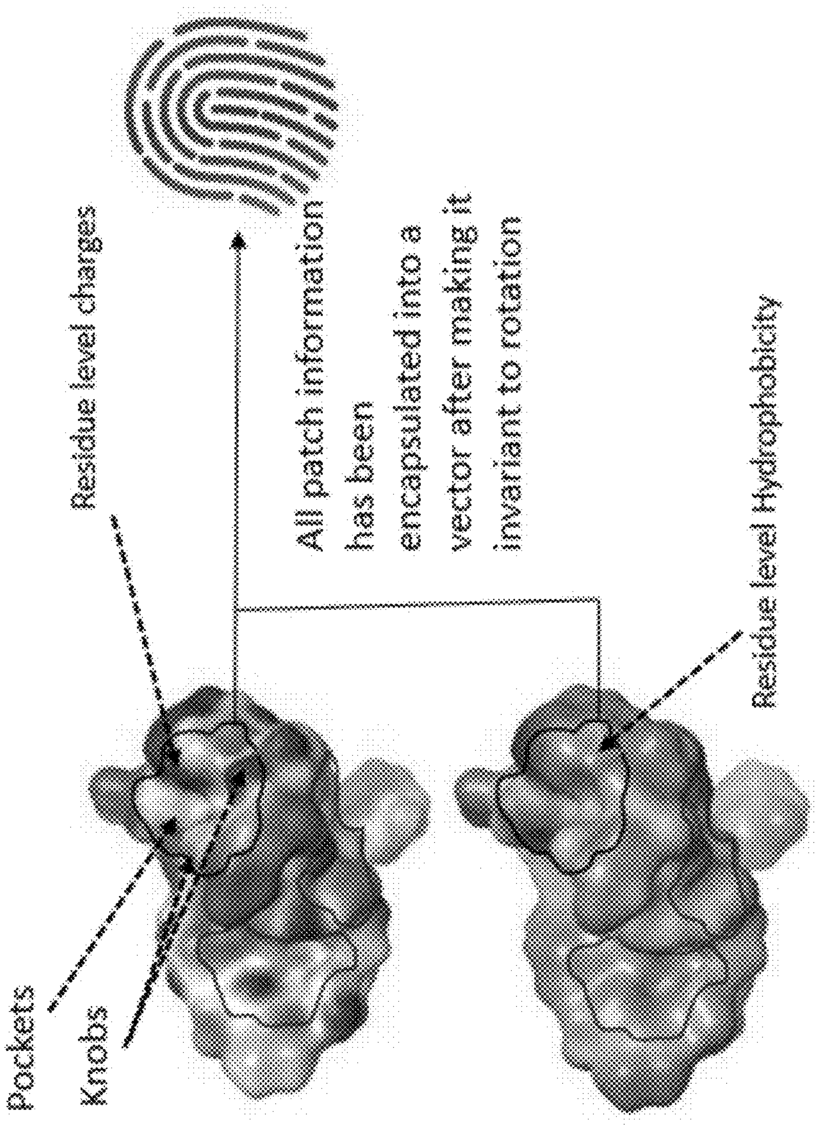
FIG. 15 is an example schematic diagram illustrating antibody fingerprinting.

FIG. 15 is an example schematic diagram illustrating antibody fingerprinting. Data relating to different molecules can be processed to generate a unique fingerprint.

Figure 16:
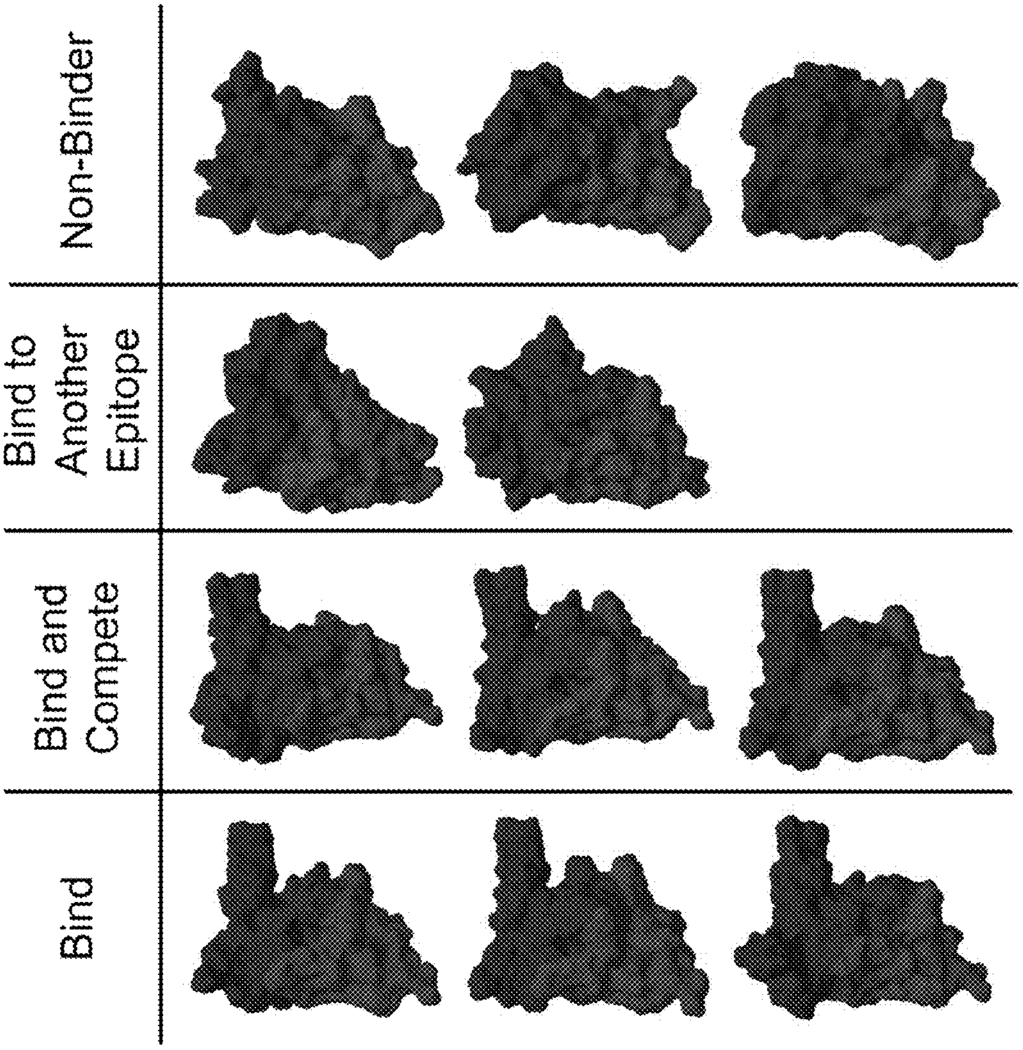
FIG. 16 is an example schematic diagram illustrating paratope fingerprinting for computing metrics.

FIG. 16 is an example schematic diagram illustrating paratope fingerprinting for computing metrics. The example visualization represents paratope geometry.

It is possible to consider patches on the surface of molecules, where every molecule contains multiple overlapping or non-overlapping patches. For that, for example, the mesh vertices of the surface of molecule can be considered and every vertex can be the center of a patch. Then, for every patch, a feature vector and a complementary feature vector can be obtained using any method such as machine learning algorithms. In some embodiments, MASIF can be used for these feature vectors. Then, for finding similar molecules to a specific molecule in terms one or multiple patches, it is possible to search in the database of molecules and compare the feature vectors of the patches on the molecules of the database and the patch(es) of the specific molecule. Likewise, for finding complement molecules to a specific molecule in terms one or multiple patches, it is possible to search in the database of molecules and compare the feature vectors of the patches on the molecules of the database with the complementary feature vector(s) the patch (es) of the specific molecule. This can have various applications, such as finding similar or complementary molecules to a specific molecule. For example, finding complementary molecules to a specific molecule can be useful for docking or binding projects in antibody-antigen cocrystals.

FIG. 10 is an example schematic diagram of data processing.

Different example use cases are provided herein. As another example, system 100 can be used for a molecule (e.g. antibody) marketplace where different vendors can offer or sell related services. A third party customer can receive a selected molecule (e.g. antibody) and the vendor client can receive a percentage of the associated price. Different companies can sell their products or services from the paratope map. For example, other antibody vendors can upload their antibody sequence information for placement on the paratope map and be selected by customers for testing, ordering, or licensing. Biological assay providers could provide their services as "add-on" services for the antibodies being ordered. Manufacturers can provide options to produce the antibodies at different scale and quality. Service provider for system 100 can receive a percentage of the transaction fees, for example.

Figure 23:
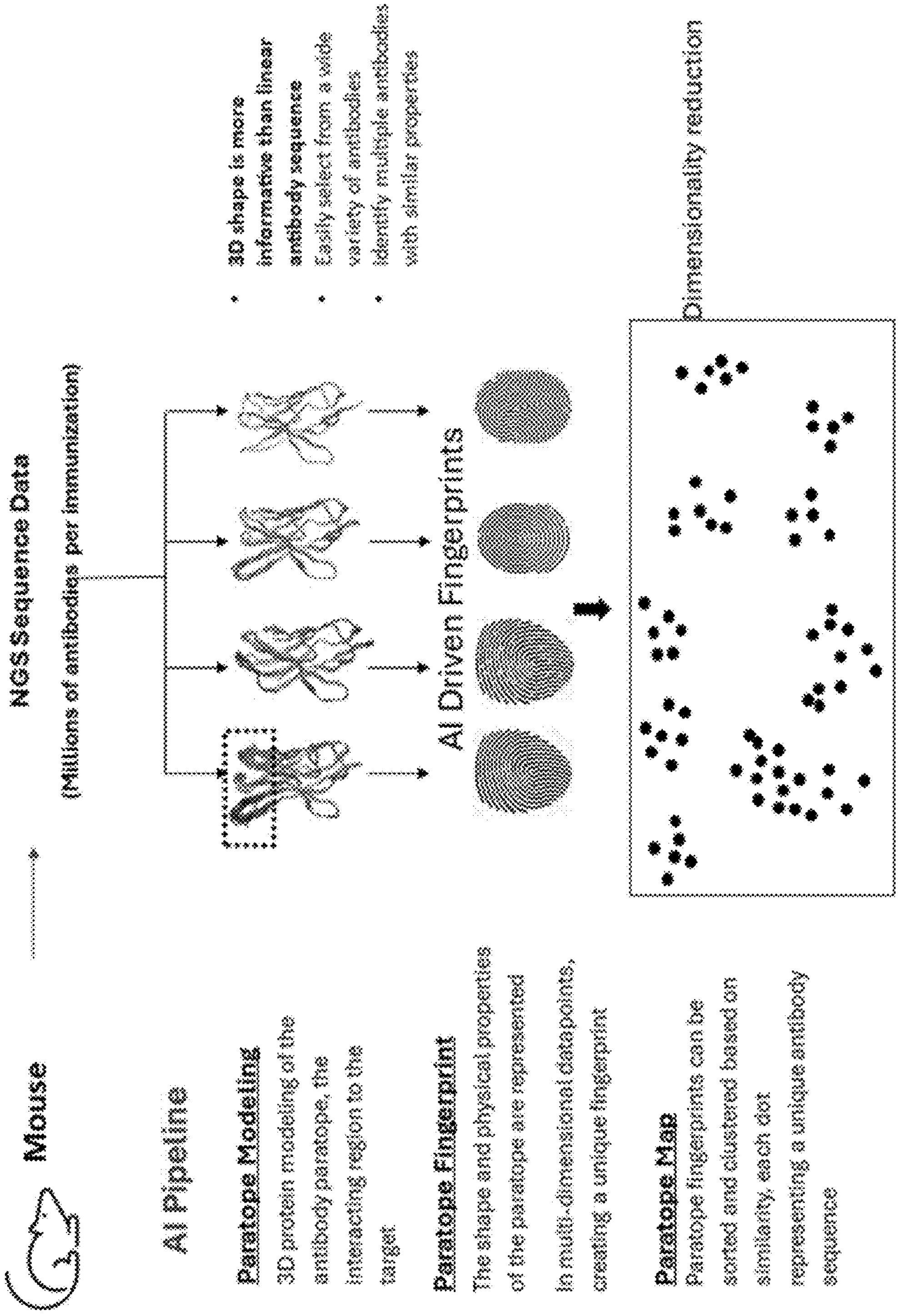
FIG. 23 illustrates an exemplary immune response exploration generated in a mouse with the same genetic background but immunized with different antigen forms, according to some embodiments.

FIG. 23 illustrates an exemplary immune response exploration generated in a mouse with the same genetic background but immunized with different antigen forms, according to some embodiments.

The different antigen forms may include, for example, full length vs. a region of interest. The map generated with the systems and methods described herein may reveal unique and overlapping paratope responses, which may demonstrate how immunization strategies impact the structural diversity and specificity of antibodies generated that would otherwise not be detected with conventional methods. This analysis can impact sampling outcome.

The paratope map can be applied to compare the immune responses of mouse strains of different genetic makeup and immunized with same antigen. Although the mice may display similar serum antibody titers, the diversity in their paratope map distributions may indicate differences in immune response patterns. Some of the mouse strains may be characterized by a broader paratope distribution relative to others which may suggest unique and distinct repertoire diversities in different strains. This differentiation can underscore how genetic background in mice can impact the landscape of generated antibodies, even under similar immunization conditions and protocols.

The systems and methods described herein can enable the identification of structurally similar candidates with the potential for similar functional activity. The platform can facilitate the discovery of candidates with comparable properties by including reference antibodies of known function in the paratope map and sampling the antibody repertoire mapped in proximity to these reference antibodies. Additionally, sampling diversely in the map can facilitate the exploration of antibody utility against less immunogenic epitopes. Using the paratope map, antibodies can be sampled from novel paratope clusters and clusters near the reference antibody for HER2. In in vitro binding assays, several antibodies may demonstrate superior binding compared to the reference antibody in both HER2-high and HER2-low expressing cancer cell lines. This sampling strategy can accelerate the identification of novel antibodies that may not have been seen in prior discovery campaigns.

These findings may highlight the platform's ability to visualize and compare antibody responses under various immunization strategies and genetic profiles. By providing a detailed view of immune repertoire diversity, the platform can support the discovery of novel target binders and facilitates the selection of optimal antibodies for clinical applications.

Example Implementations

In accordance with one aspect, there is provided a computer-implemented system 100 for mapping molecules into interfaces 300, 400. The system 100 has: a processing subsystem that includes one or more processors and one or more memories coupled with the one or more processors, the processing subsystem configured to cause the system to: receive input molecules (e.g., data 102), wherein the input molecules are a set or multiple sets of one or more molecules, wherein each molecule is defined as a sequence of information; encode the sequence of information; generate a dataset 106 by processing the input molecules (e.g., with data analysis and preparation 104), wherein the dataset 106 comprises the encoded sequence of information, three-dimensional coordinates of the sequence of information for each molecule to define structure of the molecule, and features; transform the dataset to generate a molecule map 200 and the features by feature extraction to reduce a higher number of dimensions into lower dimensional data representations that can be indicated by the interface while capturing valuable data in the lower-dimensional data representations; generate a map user interface 300, 400 comprising the molecule map 200 as a representation of the lower dimensional data representations of the dataset; and provide the map user interface.

In some embodiments, the map user interface 300, 400 comprises a visual interface, and wherein the lower dimensional data representations can be visualized in the visual interface.

In some embodiments, the input molecules are antibodies or antigen binding fragments thereof and/or antigens, and wherein the molecule map is a paratope map.

In some embodiments, the input molecules are antigens, and wherein the molecule map 200 is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, and recurrent networks.

In some embodiments, the system 100 has a data storage device 118 of a databank of molecules, wherein each molecule is assigned a unique index.

In some embodiments, the system 100 compares a molecule to the bank of molecules and assigns the molecule to an index of a closest molecule in the bank of molecules, wherein molecules assigned to the same index have similar sequences, structures, or properties.

In some embodiments, the feature extraction 202 comprises layer-wise embedding 204, wherein, for multiple datasets or multiple parts of a dataset, features of each of the multiple datasets or each of the multiple parts of the dataset are extracted separately.

In some embodiments, the features can be plotted as layers of visualization on top of each other.

In some embodiments, the map user interface 300, 400 comprising the visualization of the dataset 310 has control inputs to enable viewing of the layers separately or in relation to other layers.

In some embodiments, one or more layers are used for training for the feature extraction 202, and one or more other layers are used for testing the feature extraction.

In some embodiments, the feature extraction 202 comprises arranging embeddings in clusters 206.

In some embodiments, the feature extraction 202 comprises embedding individual molecules 208.

In some embodiments, the feature extraction 202 comprises generating clusters around molecules of interest 210.

In some embodiments, the feature extraction 202 comprises sampling from the molecule map 214.

In some embodiments, the feature extraction 202 comprises coding scores in the molecule map 216.

In some embodiments, the map user interface 300, 400 comprises a visualization of extracted features of the dataset.

In some embodiments, the system 100 has a user device 114 to display the map user interface.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface 300, 400 comprises a visualization of clusters around molecules of interest.

In some embodiments, the map user interface 300, 400 comprises one or more clusters of molecules.

In some embodiments, the processing subsystem performs feature extraction 202 for individual molecules of the dataset to obtain individual molecule embeddings.

In some embodiments, the layer-wise embedding comprises individual molecule embeddings.

In some embodiments, a user interface 300, 400 uses the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the system 100 allows a user to modify the amino acid sequence and wherein the system predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system 100 allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the information provided by the system is used to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, chimeric antibody.

In some embodiments, the processing subsystem concatenates features of parts of a molecule together to have a total feature for the molecule.

In some embodiments, the antibodies or antigen binding fragments thereof comprise antibodies from a species including, but not limited to, mice, bovine, rabbits, camels, llamas, humans, alpaca, and standard species.

In some embodiments, the encoded sequence of information refers to an encoded amino acid sequence.

In some embodiments, the processing subsystem outputs a selected molecule.

In some embodiments, there is provided a manufacture obtained by the selected molecule output of the computer-implemented system 100.

In some embodiments, there is provided a product obtained by the computer-implemented system 100.

In accordance with another aspect, there is provided a computer-implemented method 600 for mapping molecules into visual interfaces. The method 600 involves: receiving input molecules (block 602), wherein the input molecules are a set or multiple sets of one or more molecules, wherein each molecule is defined as a sequence of information; encoding the sequence of information; generating a dataset 106 by processing the input molecules (block 604), wherein the dataset 106 comprises the encoded sequence of information, three-dimensional coordinates of the sequence of information for each molecule to define structure of the molecule, the features and the fingerprints; transforming the dataset 106 to generate a molecule map 200 by feature extraction and fingerprint generation to reduce a higher number of dimensions into lower dimensional data representations that can be indicated by the interface while capturing valuable data in the lower-dimensional data representations (block 606); generating a map user interface 300, 400 comprising the molecule map 200 as a representation of the lower dimensional data representations of the dataset; and providing the map user interface 300, 400 (block 608).

In some embodiments, the map user interface 300, 400 comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map 200 is a paratope map.

In some embodiments, the input molecules are antigens, and wherein the molecule map 200 is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, and recurrent networks.

In some embodiments, the method 600 involves storing, in a data storage device 118, a databank of molecules, wherein each molecule is assigned a unique index.

In some embodiments, the method 600 involves comparing a molecule to the bank of molecules and assigning the molecule to an index of a closest molecule in the bank of molecules, wherein molecules assigned to the same index have similar sequences, structures, or properties.

In some embodiments, the method 600 involves feature extraction 202 with layer-wise embedding 204, wherein, for multiple datasets or multiple parts of a dataset, features of each of the multiple datasets or each of the multiple parts of the dataset are extracted separately.

In some embodiments, the features can be plotted as layers of visualization on top of each other.

In some embodiments, the method 600 involves providing the map user interface 300, 400 comprising the visualization of the dataset 106 with control inputs to enable viewing of the layers separately or in relation to other layers.

In some embodiments, one or more layers are used for training for the feature extraction, and one or more other layers are used for testing the feature extraction.

In some embodiments, the feature extraction 202 comprises arranging embeddings in clusters 206.

In some embodiments, the feature extraction 202 comprises embedding individual molecules 208.

In some embodiments, the feature extraction 202 comprises generating clusters around molecules of interest 210.

In some embodiments, the feature extraction 202 comprises sampling from the molecule map 214.

In some embodiments, the feature extraction 202 comprises coding scores in the molecule map 216.

In some embodiments, the map user interface 300, 400 comprises a visualization of extracted features of the dataset 106.

In some embodiments, the method 600 involves using an user device 114 to display the map user interface 300, 400.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface 300, 400 comprises two-dimensional or three-dimensional embeddings changing over the time as the time-series representing four-dimensional embeddings.

In some embodiments, the method 600 involves using the map user interface 300, 400 to provide a visualization of clusters around molecules of interest.

In some embodiments, the map user interface 300, 400 comprises one or more clusters of molecules.

In some embodiments, the method 600 involves performing feature extraction 202 for individual molecules of the dataset 106 to obtain individual molecule embeddings.

In some embodiments, the layer-wise embedding comprises individual molecule embeddings.

In some embodiments, the method 600 involves using the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the method 600 involves modifying the amino acid sequence and wherein the system 100 predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the method 600 allows a user to import further molecules and determine similarity with the input molecules.

In some embodiments, the molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the method 600 involves using the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, chimeric antibody.

In some embodiments, the method 600 involves concatenating features of parts of a molecule together to have a total feature for the molecule.

In some embodiments, the encoded sequence of information refers to an encoded amino acid sequence.

In some embodiments, the method 600 involves outputting a selected molecule.

In some embodiments, there is provided a manufacture obtained by the selected molecule output of the computer-implemented method 600.

In some embodiments, there is provided a product obtained by the computer-implemented method 600.

In some embodiments, the method 600 involves a step of producing a molecule identified or selected from the map user interface 300, 400.

In some embodiments, there is provided a product obtained by the computer-implemented method 600.

In some embodiments, the product is an antibody or an antigen binding fragment thereof.

In accordance with another aspect, there is provided a non-transitory computer-readable medium or media having stored thereon machine interpretable instructions which, when executed by a processing subsystem, cause the processing subsystem to perform a method 600 for mapping molecules into visual interfaces, the method 600 comprising: receiving input molecules (block 602), wherein the input molecules are a set or multiple sets of one or more molecules, wherein each molecule is defined as a sequence of information; encoding the sequence of information; generating a dataset by processing the input molecules (block 604), wherein the dataset 106 comprises the encoded sequence of information, three-dimensional coordinates of the sequence of information for each molecule to define structure of the molecule, the features and the fingerprints; transforming the dataset 106 to generate a molecule map 200 by feature extraction and fingerprint generation to reduce a higher number of dimensions into lower dimensional data representations that can be indicated by the interface while capturing valuable data in the lower-dimensional data representations (block 606); generating a map user interface 300, 400 comprising the molecule map 200 as a representation of the lower dimensional data representations of the dataset (block 608); and providing the map user interface.

In accordance with another aspect, there is provided a computer-implemented system 100 for an interface relating to molecules. The system 100 has: a processing subsystem that includes one or more processors and one or more memories coupled with the one or more processors, the processing subsystem configured to cause the system to: receive input molecules (e.g., data 102), wherein the input molecules are a set or multiple sets of one or more molecules, wherein each molecule is defined as a sequence of information; encode the sequence of information; generate a dataset 106 by processing the input molecules, wherein the dataset 106 comprises the encoded sequence of information, three-dimensional coordinates of the sequence of information for each molecule to define structure of the molecule, the features and the fingerprints; transform the dataset 106 by feature extraction and fingerprint generation to reduce a higher number of dimensions into lower dimensional data representations that can be indicated by the interface while capturing valuable data in the lower-dimensional data representations; generate one or more metrics from the transformed dataset 106, wherein the one or more metrics comprise lower dimensional data representations of the dataset 106 and summarize characteristics of the input molecules; and provide the one or more metrics to an interface 300, 400.

In accordance with another aspect, there is provided a computer-implemented system 100 for a visual interface 300, 400 for mapping molecules. The system 100 has: a processing subsystem that includes one or more processors and one or more memories coupled with the one or more processors, the processing subsystem providing a map user interface 300, 400, wherein the map user interface 300, 400: receives input molecules (e.g., data 102), wherein the input molecules are a set or multiple sets of one or more molecules, wherein each molecule is defined as a sequence of information; and provides a map interface 300, 400 comprising a molecule map 200 as a representation of lower dimensional data representations of a dataset 106 for the input molecules, wherein the dataset 106 comprises the sequence of information for each molecule, three-dimensional coordinates of the sequence of information for each molecule to define structure of the molecule, and features; wherein the molecule map 200 comprises a transformation of the dataset 106 by feature extraction 202 and fingerprint generation to reduce a higher number of dimensions into lower dimensional data representations that can be indicated by the interface while capturing valuable data in the lower-dimensional data representations.

In some embodiments, the input molecules are proteins or protein-like molecules comprising antibodies and antigens.

In some embodiments, the antibodies comprise antibodies of a species including, but not limited to, mice, bovine, rabbits, camels, llamas, humans, alpaca, and standard species.

In some embodiments, the input molecules are antibodies and antigens, and wherein the molecule map is a paratope map.

In some embodiments, the input molecules are antigens, and wherein the molecule map is an epitope map.

In some embodiments, the map user interface 300, 400 comprises layer-wise embedding providing layers for the map visualization.

In some embodiments, the map user interface 300, 400 plots features as layers of the map visualization on top of each other.

In some embodiments, the map user interface 300, 400 has control inputs to enable viewing of the layers separately or in relation to other layers.

In some embodiments, the map user interface 300, 400 has control inputs to add or remove a layer of the layers for the map visualization.

In some embodiments, the map user interface 300, 400 comprises a visualization of extracted features of the dataset 106.

In some embodiments, the map user interface 300, 400 receives one or more reference molecules or target molecules, wherein the transformation of the dataset 106 is based on the one or more reference molecules or target molecules.

In some embodiments, the map user interface 300, 400 receives one or more scores for the molecules, wherein the scores comprise expressibility scores and fuzzy panning scores.

In some embodiments, the map visualization comprises one or more clusters corresponding to the molecules, wherein the map user interface 300, 400 receives cluster control commands to update the map visualization with hyperparameters of the one or more clusters.

In some embodiments, the map visualization displays one or more scores in relation to the molecules, the scores comprising expressibility scores or fuzzy panning scores.

In some embodiments, the map user interface 300, 400 receives a control commands for sampling from at least a portion of the map visualization.

In some embodiments, the map user interface 300, 400 receives a control commands for editing samples drawn from at least a portion of the map visualization.

In some embodiments, the map user interface 300, 400 receives plot settings corresponding to visualization characteristics for the map visualization.

In some embodiments, a user device 114 can display the map user interface.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface 300, 400 comprises a visualization of clusters around molecules of interest.

In some embodiments, the map user interface 300, 400 comprises one or more clusters of molecules.

In some embodiments, the map user interface 300, 400 comprises individual molecule embeddings.

In some embodiments, the layer-wise embedding comprises individual molecule embeddings.

In some embodiments, the map user interface 300, 400 receives scores.

In some embodiments, the map user interface 300, 400 exports files.

In some embodiments, the map user interface 300, 400 comprises one or more buttons for adding or removing layers 302, one or more buttons for receiving input molecules 304, one or more buttons for adding or removing individual molecules 306, and one or more buttons for importing scores 308.

In some embodiments, the map user interface 300, 400 comprises a plurality of settings selected from the group of navigational settings for the map visualization 312, plot settings 314, settings for coding scores in the map visualization 316, cluster settings 324, settings for editing samples 330, sample settings 328, report settings 322, map analysis settings 320, and export settings.

In accordance with an aspect, there is provided a computer-implemented system 100 for mapping proteins, protein-like molecules or fragments thereof into visual interfaces and generating maps for display and interaction. The system 100 includes a processing subsystem that includes one or more processors and one or more memories coupled with the one or more processors, the processing subsystem configured to cause the system to: receive data 102 for a set or multiple sets of one or more input proteins, protein-like molecules or fragments thereof, wherein the data comprises features of the one or more proteins, protein-like molecules or fragments thereof; generate at least one dataset 106 by processing the data for the set or multiple sets of the one or more input proteins, protein-like molecules or fragments thereof (e.g., using data analysis and preparation 104); transform one or more of the data and the at least one dataset(s) to generate a map and additional features by feature extraction 202 or feature selection to reduce higher dimensional data representations into lower dimensional data representations for visualization by the visual interface, wherein the lower-dimensional data representations capture valuable information of the one or more of the data and the at least one dataset(s) 106, the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generate a visual map interface comprising the map 200 as a visual representation of the lower dimensional data representations of the dataset, the visual representation comprising visualizations representing the dataset 106 as one or more layers of proteins, protein-like molecules or fragments thereof, each layer comprising one or more of the one or more clusters of proteins, protein-like molecules or fragments thereof; and provide the visual map interface 300, 400 with tools for interaction with the map 200, wherein interaction with the map 200 comprises one or more of inspection, searching, sampling, clustering, and analysis of the one or more proteins, protein-like molecules or fragments thereof or newly generated proteins, protein-like molecules or fragments thereof; receive commands or detect interactions with the map by the tools at the visual map interface; update the map 200 based on the commands or interactions; and trigger an update to the visual map interface with the updated map 200.

In some embodiments, the proteins, protein-like molecules or fragments thereof are selected from: antibodies, antigens, lectins, receptors, ligands, enzymes, or fragments thereof.

In some embodiments, the proteins, protein-like molecules or fragments thereof comprises antibodies or fragments thereof and/or antigens or fragments thereof, and wherein the map 200 is a paratope map or an epitope map or a map 200 comprising proteins or protein-like molecules or fragments thereof.

In some embodiments, the proteins, protein-like molecules or fragments thereof comprise antibodies or antibody fragments thereof and wherein the data comprises one or more of the structure of one or more antibodies or antibody fragments thereof, the amino acid sequence of one or more of the antibodies or antibody fragments thereof, amino acid atom or molecule coordinates, and biophysical properties of one or more antibodies or antibody fragments thereof.

In some embodiments, the proteins, protein-like molecules or fragments thereof are selected from conventional antibodies, antibody-like molecules, artificial antibodies, antibody mimetics, single domain antibodies, single chain antibody, humanized antibodies, chimeric antibodies, or fragments thereof.

In some embodiments, the fragments comprise antigen binding fragments or antigen binding domains.

In some embodiments, the antigen binding fragments or the antigen binding domains are selected from one or more complementarity determining regions and/or one or more framework regions, one or more variable domains, or paratope.

In some embodiments, the visual representation of the lower dimensional data representations comprises different colours and/or marker shapes and/or marker sizes and/or color transparencies and/or color gradients to indicate the one or more layers and the one or more clusters of proteins, protein-like molecules or fragments thereof.

In some embodiments, the lower dimensional data representations are one-dimensional, two-dimensional, three-dimensional, or four-dimensional data representations.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, sequence processing algorithms, image processing algorithms, computer vision algorithms, and identity transformation.

In some embodiments, the processing subsystem causes the system 100 to cluster the one or more of the data and the dataset 106 to generate the one or more clusters of proteins, protein-like molecules or fragments thereof.

In some embodiments, the processing subsystem causes the system 100 to encode the raw data and generate additional features from the encoded data.

In some embodiments, the visual representation superimposes the one or more layers of proteins, protein-like molecules or fragments thereof as overlays as part of the visualizations representing the dataset 106, wherein the tools trigger movement of the one or more layers to different positions or levels, or removal thereof from the map or change of order of displaying the layers or zooming in or out of one or multiple layers or moving in the map across layers.

In some embodiments, the processing subsystem causes the system 100 to implement map analysis, wherein map analysis comprises one or more of generating clusters around proteins, protein-like molecules or fragments thereof of interest, arranging embeddings in clusters, layer-wise embedding, embedding individual proteins, protein-like molecules or fragments thereof, sampling from the map, coding scores in the map, wherein the map contains the one or more clusters and visualizes the one or more clusters.

In some embodiments, the processing subsystem causes the system 100 to generate or calculate one or more clusters of proteins, protein-like molecules or fragments thereof, and wherein the map user interface comprises a visualization of the one or more clusters of proteins, protein-like molecules or fragments thereof.

In some embodiments, feature extraction 202 comprises extracting useful information from the dataset and feature selection comprises selecting a subset of the dataset of proteins, protein-like molecules or fragments thereof.

In some embodiments, the processing subsystem causes the system 100 to transform the one or more of the data and the dataset 106 to generate the map 200 by one or more of sequencing and clustering, sampling, intersection of data subsets, and subtraction of data subsets.

In some embodiments, processing subsystem causes the system 100 to partition or segment the digital map 200 into a plurality of map tiles, label each of the one or more clusters with a corresponding map tile of the plurality of map tiles, and display the one or more clusters within the plurality of map tiles using the labels, wherein the visualization indicates the plurality of map tiles and the one or more clusters.

In some embodiments, the processing subsystem causes the system 100 to: (i) intersect one or more layers of proteins, protein-like molecules or fragments thereof or (ii) subtract one or more layers of proteins, protein-like molecules or fragments thereof or (iii) add one or more layers of proteins, protein-like molecules or fragments thereof, to update the map based on the commands or interactions.

In some embodiments, the tools at the visual map interface 300, 400 comprises a sampling tool for sampling proteins, protein-like molecules or fragments thereof from the one or more clusters of proteins, protein-like molecules or fragments thereof, wherein the processing subsystem causes the system to update the map by sampling proteins, protein-like molecules or fragments thereof in response to activation of the sampling tool and trigger an update to the visual map interface with the updated map to visualize the sampling.

In some embodiments, the processing subsystem causes the system 100 to subtract the unimmunized library of proteins, protein-like molecules or fragments thereof from the immunized library of proteins, protein-like molecules or fragments thereof to filter out nonspecific proteins, protein-like molecules or fragments thereof and to reduce the search space for sampling and searching for specific molecule-candidates for one or multiple targets, wherein if multiple layers or datasets exist for the immunized library, the subsystem causes the system to intersect layers or datasets after subtraction to reduce the search space even further.

In some embodiments, the processing subsystem causes the system 100 to subtract the libraries of proteins, protein-like molecules or fragments thereof immunized against one or multiple targets from the library of proteins, protein-like molecules or fragments thereof immunized against a target of interest, to filter out moieties which are non-binders to the target of interest, and to reduce the search space for sampling and searching for specific molecule-candidates for the target of interest, wherein if multiple layers or datasets exist for the immunized library against the target of interest, the subsystem causes the system to intersect layers or datasets after subtraction to reduce the search space even further.

In some embodiments, the processing subsystem causes the system 100 to export or report the inspection, searching, sampling, clustering, and analysis of the proteins, protein-like molecules or fragments thereof through text, tables, plots, or visualizations.

According to an aspect, there is provided a computer process 600 for mapping proteins, protein-like molecules or fragments thereof into visual interfaces and generating digital maps for display and interaction. The method 600 includes: receiving data 102 for a set or multiple sets of one or more input proteins (block 602), protein-like molecules or fragments thereof, wherein the data 102 comprises features of the one or more proteins, protein-like molecules or fragments thereof; generating at least one dataset 106 by processing the data for the set or multiple sets of the one or more input proteins (block 604), protein-like molecules or fragments thereof; transforming one or more of the data and the at least one dataset(s) 106 to generate a map and additional features by feature extraction or feature selection to reduce higher dimensional data representations into lower dimensional data representations for visualization by the visual interface (block 606), wherein the lower-dimensional data representations capture valuable information of the one or more of the data and the at least one dataset(s) 106, the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generating a visual map interface comprising the map as a visual representation of the lower dimensional data representations of the dataset, the visual representation comprising visualizations representing the dataset 106 as one or more layers of proteins, protein-like molecules or fragments thereof (block 608), each layer comprising one or more of the one or more clusters of proteins, protein-like molecules or fragments thereof; and providing the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof; receiving commands or detect interactions with the map by the tools at the visual map interface; and triggering an update to the visual map interface and the map based on the commands or interactions.

According to an aspect, there is provided a computer-readable medium encoded with instructions 600, that when executed by a processor, cause the processor to map proteins, protein-like molecules or fragments thereof into visual interfaces and generate digital maps 200 for display and interaction. The instructions 600 comprising instructions for: receiving data 102 for a set or multiple sets of one or more input proteins (block 602), protein-like molecules or fragments thereof, wherein the data 102 comprises features of the one or more proteins, protein-like molecules or fragments thereof; generating at least one dataset 106 by processing the data for the set or multiple sets of the one or more input proteins, protein-like molecules or fragments thereof (block 604); transforming one or more of the data 102 and the at least one dataset(s) 106 to generate a map 200 and additional features by feature extraction or feature selection to reduce higher dimensional data representations into lower dimensional data representations for visualization by the visual interface while (block 606), wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof; generating a visual map interface 300, 400 comprising the map 200 as a visual representation of the lower dimensional data representations of the dataset 106 (block 608), the visual representation comprising visualizations representing the dataset 106 as one or more layers of proteins, protein-like molecules or fragments thereof, each layer comprising one or more of the one or more clusters of proteins, protein-like molecules or fragments thereof; and providing the visual map interface 300, 400 with tools for interaction with the map, wherein interaction with the map 200 comprises one or more of inspection, searching, sampling, clustering, and analysis of the one or more proteins, protein-like molecules or fragments thereof or newly generated proteins, protein-like molecules or fragments thereof; receiving commands or detect interactions with the map by the tools at the visual map interface; and triggering an update to the visual map interface and the map based on the commands or interactions.

According to an aspect, there is provided a computer-implemented system 100 for mapping molecules into interfaces and generating maps 200 for interfaces 300, 400. The system 100 including a processing subsystem that includes one or more processors and one or more memories coupled with the one or more processors, the processing subsystem configured to cause the system 100 to: receive data 102 for a set or multiple sets of one or more input molecules, wherein the input molecules are a set or multiple sets of one or more molecules, wherein the data 102 comprises features of the molecules; generate at least one dataset 106 by processing the data 102 for the set or multiple sets of the one or more input molecules, wherein the dataset 106 comprises encoded sequences of information, coordinates for each molecule to define structure of the molecule, and features; transform one or more of the data 102 and the at least one dataset 106 to generate a map and additional features by feature extraction or feature selection to reduce higher dimensional data representations into lower dimensional data representations that can be indicated, depicted or visualized by the interface while capturing valuable information in the lower-dimensional data representations, the lower dimensional data representations comprising one or more clusters of the input molecules or newly generated molecules; generate a map user interface 300, 400 comprising the map 200 as a representation of the lower dimensional data representations of the dataset 106, the representation representing the at least one dataset 106 as one or more layers of molecules, each layer comprising one or more of the one or more clusters of molecules; and provide the map user interface.

In some embodiments, the processing subsystem causes the system 100 to: provide the map user interface 300, 400 with tools for interaction with the map and inspection, searching, sampling, clustering and analysis of the one or more input molecules or newly generated molecules; receive commands or detect interactions with the map 200 by the tools at the visual map interface 300, 400; update the map 200 based on the commands or interactions; and trigger an update to the map interface 300, 400 with the updated map 200.

In some embodiments, the molecules are proteins, protein-like molecules, fragments thereof, small molecule drugs, or nucleic acid molecules.

In some embodiments, the input proteins, protein-like molecules or fragments thereof comprises antibodies or fragments thereof and/or antigens or fragments thereof, and wherein the map is a paratope map or an epitope map or a map comprising proteins or protein-like molecules or fragments thereof.

In some embodiments, the proteins, protein-like molecules or fragments thereof are selected from the group consisting of: antibodies, antigen binding fragments, drug candidates, compounds, binding candidates, and binding agents.

In some embodiments, the map user interface 300, 400 comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map 200 is a paratope map.

In some embodiments, the input molecules are antigens, and wherein the molecule map 200 is an epitope map.

In some embodiments, the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, and recurrent networks.

In some embodiments, the system 100 further comprises a data storage device 118 of a databank of molecules, wherein each molecule is assigned a unique index.

In some embodiments, the system 100 compares a molecule to the bank of molecules and assigns the molecule to an index of a closest molecule in the bank of molecules, wherein molecules assigned to the same index have similar sequences, structures, or properties.

In some embodiments, the feature extraction 202 comprises layer-wise embedding, wherein, for multiple datasets or multiple parts of a dataset, features of each of the multiple datasets or each of the multiple parts of the dataset are extracted separately.

In some embodiments, the features can be plotted as layers of visualization on top of each other.

In some embodiments, the map user interface 300, 400 comprising the visualization of the dataset 106 has control inputs to enable viewing of the layers separately or in relation to other layers.

In some embodiments, one or more layers are used for training for the feature extraction, and one or more other layers are used for testing the feature extraction 202.

In some embodiments, the feature extraction 202 comprises arranging embeddings in clusters.

In some embodiments, the feature extraction 202 comprises embedding individual molecules.

In some embodiments, the feature extraction 202 comprises generating clusters around molecules of interest.

In some embodiments, the feature extraction 202 comprises sampling from the molecule map 200.

In some embodiments, the feature extraction 202 comprises coding scores in the molecule map 200.

In some embodiments, the map user interface 300, 400 comprises a visualization of extracted features of the dataset 106.

In some embodiments, further comprising a user device 114 to display the map user interface 300, 400.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface 300, 400 comprises a visualization of clusters around molecules of interest.

In some embodiments, the map user interface 300, 400 comprises one or more clusters of molecules.

In some embodiments, the processing subsystem performs feature extraction 202 for individual molecules of the dataset to obtain individual molecule embeddings.

In some embodiments, the layer-wise embedding comprises individual molecule embeddings.

In some embodiments, a user interface 300, 400 uses the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the system 100 allows a user to modify the amino acid sequence and wherein the system predicts the impact of the modification on the features (binding, function, stability, expressibility, affinity, immunogenicity) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system 100 allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, uses the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, chimeric antibody.

In some embodiments, the processing subsystem concatenates features of parts of a molecule together to have a total feature for the molecule.

In some embodiments, the encoded sequence of information refers to an encoded amino acid sequence.

In some embodiments, the processing subsystem outputs a selected molecule.

According to an aspect, there is provided a manufacture obtained by the selected molecule output of the computer-implemented system 100 described herein.

According to an aspect, there is provided a product obtained by the computer-implemented system 100 described herein.

According to an aspect, there is provided a computer-implemented method 600 for mapping molecules into interfaces and generating maps 200 for interfaces 300, 400. The method 600 includes: receiving data 102 for a set or multiple sets of one or more input molecules (block 602), wherein the input molecules are a set or multiple sets of one or more molecules, wherein the data 102 comprises features of the molecules; generating at least one dataset 106 by processing the data for the set or multiple sets of the one or more input molecules (block 604), wherein the dataset 106 comprises encoded sequences of information, coordinates for each molecule to define structure of the molecule, features, and fingerprints; transforming one or more of the data 102 and the at least one dataset 106 to generate a map 200 and additional features by feature extraction 202, feature selection or fingerprint generation to reduce higher dimensional data representations into lower dimensional data representations that can be indicated (block 606), depicted or visualized by the interface while capturing valuable information in the lower-dimensional data representations, the lower dimensional data representations comprising one or more clusters of the input molecules or newly generated molecules; generating a map user interface 300, 400 comprising the map 200 as a representation of the lower dimensional data representations of the dataset (block 608), the representation representing the at least one dataset 106 as one or more layers of molecules, each layer comprising one or more of the one or more clusters of molecules; and providing the map user interface 300, 400.

In some embodiments, the map user interface 300, 400 comprises a visual interface, and wherein the lower dimensional data representations can be visualized in the visual interface.

In some embodiments, the input molecules are proteins or protein-like molecules comprising antibodies or antigen binding fragments thereof and/or antigens.

In some embodiments, the antibodies or antigen binding fragments thereof comprise antibodies from a species including, but not limited to, mice, bovine, rabbits, camels, llamas, humans, alpaca, and standard species.

In some embodiments, the input molecules are antibodies or antigen binding fragments thereof and/or antigens, and wherein the molecule map 200 is a paratope map.

In some embodiments, the input molecules are antigens, and wherein the molecule map 200 is an epitope map.

In some embodiments, the features comprise fingerprints, wherein the processing subsystem extracts features 202 and generates the fingerprints using machine learning or statistical methods involving one or more of dimensionality reduction, a reconstruction autoencoder, a variational autoencoder, adversarial autoencoder, neural networks, graph neural networks, attention networks, and recurrent networks.

In some embodiments, the method 600 further includes storing, in a data storage device 118, a databank of molecules, wherein each molecule is assigned a unique index.

In some embodiments, the method 600 further includes comparing a molecule to the bank of molecules and assigning the molecule to an index of a closest molecule in the bank of molecules, wherein molecules assigned to the same index have similar sequences, structures, or properties.

In some embodiments, the method 600 further includes feature extraction 202 with layer-wise embedding, wherein, for multiple datasets 106 or multiple parts of a dataset 106, features of each of the multiple datasets or each of the multiple parts of the dataset are extracted separately.

In some embodiments, the features can be plotted as layers of visualization on top of each other.

In some embodiments, the method 600 further includes providing the map user interface 300, 400 comprising the visualization of the dataset 106 with control inputs to enable viewing of the layers separately or in relation to other layers 302.

In some embodiments, one or more layers are used for training for the feature extraction 202, and one or more other layers are used for testing the feature extraction 202.

In some embodiments, the feature extraction 202 comprises arranging embeddings in clusters 206.

In some embodiments, the feature extraction 202 comprises embedding individual molecules 208.

In some embodiments, the feature extraction 202 comprises generating clusters around molecules of interest 210.

In some embodiments, the feature extraction 202 comprises sampling from the molecule map 214.

In some embodiments, the feature extraction 202 comprises coding scores in the molecule map 216.

In some embodiments, the map user interface 300, 400 comprises a visualization of extracted features of the dataset 106.

In some embodiments, the method 600 further includes using an user device 118 to display the map user interface 300, 400.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the method 600 further includes using the map user interface 300, 400 to provide a visualization of clusters around molecules of interest.

In some embodiments, the map user interface 300, 400 comprises one or more clusters of molecules.

In some embodiments, the method 600 further includes performing feature extraction 202 for individual molecules 208 of the dataset 106 to obtain individual molecule embeddings.

In some embodiments, the layer-wise embedding comprises individual molecule embeddings.

In some embodiments, the method 600 further includes using the extracted features to characterize and/or obtain information on the input molecules, wherein the input molecules is optionally from a cluster of interest.

In some embodiments, the information includes the extent, nature and/or robustness of an immune response (towards an antigen such as immunogen or vaccine).

In some embodiments, the input molecules comprise antibodies or antigen binding fragments thereof and wherein the information comprises the amino acid sequence of one or more of the antibodies or antigen binding fragments.

In some embodiments, the input molecules comprise antigens and wherein the information comprises the amino acid sequence of one or more of the antigens.

In some embodiments, the method 600 further includes modifying the amino acid sequence and wherein the system predicts the impact of the modification on the features (binding, function, stability, expressibility, affinity, immunogenicity etc.) of the molecule.

In some embodiments, the modification comprises amino acid substitution, deletion and/or addition in one or more CDRs, variable regions, framework regions and/or constant regions of the antibody or antigen binding fragment thereof.

In some embodiments, the modification is humanization, deimmunization, glycosylation, deglycosylation of the antibody or antigen binding fragment thereof.

In some embodiments, the system 100 allows a user to import further molecules and determine similarity with the input molecules.

In some embodiments, the further molecules are further antibodies or antigen binding fragments thereof and the similarity is paratope similarity.

In some embodiments, the output comprises an antibody or an antigen binding fragment thereof selected from the map or a variant thereof.

In some embodiments, a user synthesizes an input or output molecule or variant thereof or causes the input or output molecule or variant thereof to be synthesized.

In some embodiments, the method 600 further includes using the information provided by the system to manufacture a molecule.

In some embodiments, the input molecules comprise single domain antibodies or antigen binding fragments thereof and wherein the output molecule comprises an antibody or an antigen binding fragment thereof selected from conventional antibody, single domain antibody, single chain variable fragment, humanized antibody, chimeric antibody.

In some embodiments, the method 600 further includes concatenating features of parts of a molecule together to have a total feature for the molecule.

In some embodiments, the encoded sequence of information refers to an encoded amino acid sequence.

In some embodiments, the method 600 further includes outputting a selected molecule.

According to an aspect, there is provided a manufacture obtained by the selected molecule output of the computer-implemented method 600 described herein.

According to an aspect, there is provided a product obtained by the computer-implemented method 600 described herein.

In some embodiments, the method 600 comprises a step of producing a molecule identified or selected from the map user interface 300, 400.

According to an aspect, there is provided a product obtained by the computer-implemented method 600 described herein.

In some embodiments, the product is an antibody or an antigen binding fragment thereof.

According to an aspect, there is provided a non-transitory computer-readable medium or media having stored thereon machine interpretable instructions which, when executed by a processing subsystem, cause the processing subsystem to perform a method 600 for mapping molecules into visual interfaces and generating maps 200 for interfaces. The method 600 includes receiving data 102 for a set or multiple sets of one or more input molecules (block 602), wherein the input molecules are a set or multiple sets of one or more molecules, wherein the data 102 comprises features of the molecules; generating at least one dataset 106 by processing the data 102 for the set or multiple sets of the one or more input molecules (block 604), wherein the dataset 106 comprises encoded sequences of information, coordinates for each molecule to define structure of the molecule, features and fingerprints; transforming one or more of the data 102 and the at least one dataset 106 to generate a map 200 and additional features by feature extraction 202, feature selection, or fingerprint generation to reduce higher dimensional data representations into lower dimensional data representations that can be indicated by the interface while capturing valuable information in the lower-dimensional data representations (block 606), the lower dimensional data representations comprising one or more clusters of the input molecules or newly generated molecules; generating a map user interface 300, 400 comprising the map 200 as a representation of the lower dimensional data representations of the dataset 106, the representation representing the at least one dataset 106 as one or more layers of molecules, each layer comprising one or more of the one or more clusters of molecules; and providing the map user interface 300, 400.

According to an aspect, there is provided a computer-implemented system 100 for an interface relating to molecules. The system 100 including: a processing subsystem that includes one or more processors and one or more memories coupled with the one or more processors, the processing subsystem configured to cause the system 100 to: receive input molecules (e.g., as data 102), wherein the input molecules are a set or multiple sets of one or more molecules, wherein each molecule is defined as a sequence of information; encode the sequence of information; generate a dataset 106 by processing the input molecules, wherein the dataset 106 comprises the encoded sequence of information, three-dimensional coordinates of the sequence of information for each molecule to define structure of the molecule, the features and the fingerprints; transform the dataset 106 by feature extraction 202 and fingerprint generation to reduce a higher number of dimensions into lower dimensional data representations that can be indicated by the interface while capturing valuable data in the lower-dimensional data representations; generate one or more metrics from the transformed dataset 106, wherein the one or more metrics comprise lower dimensional data representations of the dataset 106 and summarize characteristics of the input molecules; and provide the one or more metrics to an interface.

According to an aspect, there is provided a computer-implemented system 100 for a visual interface for mapping molecules. The system 100 includes a processing subsystem that includes one or more processors and one or more memories coupled with the one or more processors, the processing subsystem providing a map user interface 300, 400, wherein the map user interface 300, 400: receives input molecules (e.g., as data 102), wherein the input molecules are a set or multiple sets of one or more molecules, wherein each molecule is defined as a sequence of information; and provides a map interface 300, 400 comprising a molecule map as a representation of lower dimensional data representations of a dataset for the input molecules, wherein the dataset comprises the sequence of information for each molecule, three-dimensional coordinates of the sequence of information for each molecule to define structure of the molecule, and features; wherein the molecule map 200 comprises a transformation of the dataset 106 by feature extraction 202 and fingerprint generation to reduce a higher number of dimensions into lower dimensional data representations that can be indicated by the interface while capturing valuable data in the lower-dimensional data representations.

In some embodiments, the input molecules are proteins or protein-like molecules comprising antibodies and antigens.

In some embodiments, the antibodies comprise antibodies of a species including, but not limited to, mice, bovine, rabbits, camels, llamas, humans, alpaca, and standard species.

In some embodiments, the input molecules are antibodies and antigens, and wherein the molecule map is a paratope map.

In some embodiments, the input molecules are antigens, and wherein the molecule map is an epitope map.

In some embodiments, the map user interface 300, 400 comprises layer-wise embedding providing layers for the map visualization.

In some embodiments, the map user interface 300, 400 plots features as layers of the map visualization on top of each other.

In some embodiments, the map user interface 300, 400 has control inputs to enable viewing of the layers separately or in relation to other layers.

In some embodiments, the map user interface 300, 400 has control inputs to add or remove a layer of the layers for the map visualization 302.

In some embodiments, the map user interface 300, 400 comprises a visualization of extracted features of the dataset 106.

In some embodiments, the map user interface 300, 400 receives one or more reference molecules or target molecules, wherein the transformation of the dataset 106 is based on the one or more reference molecules or target molecules.

In some embodiments, the map user interface 300, 400 receives one or more scores for the molecules, wherein the scores comprise expressibility scores and fuzzy panning scores.

In some embodiments, the map visualization comprises one or more clusters corresponding to the molecules, wherein the map user interface 300, 400 receives cluster control commands to update the map visualization with hyperparameters of the one or more clusters.

In some embodiments, the map visualization displays one or more scores in relation to the molecules, the scores comprising expressibility scores or fuzzy panning scores.

In some embodiments, the map user interface 300, 400 receives a control commands for sampling from at least a portion of the map visualization.

In some embodiments, the map user interface 300, 400 receives a control commands for editing samples drawn from at least a portion of the map visualization.

In some embodiments, the map user interface 300, 400 receives plot settings corresponding to visualization characteristics for the map visualization.

In some embodiments, the system 100 further includes a user device 114 to display the map user interface 300, 400.

In some embodiments, the map user interface 300, 400 is one-dimensional, two-dimensional, three-dimensional, four-dimensional, or higher dimensional.

In some embodiments, embeddings of the layer-wise embedding change over time as a time-series, and wherein the map user interface comprises two-dimensional or three-dimensional embeddings changing over the time as the time-series representing four-dimensional embeddings.

In some embodiments, the map user interface 300, 400 comprises a visualization of clusters around molecules of interest.

In some embodiments, the map user interface 300, 400 comprises one or more clusters of molecules.

In some embodiments, the map user interface 300, 400 comprises individual molecule embeddings.

In some embodiments, the layer-wise embedding comprises individual molecule embeddings.

In some embodiments, the map user interface 300, 400 receives scores.

In some embodiments, the map user interface 300, 400 exports files.

In some embodiments, the map user interface 300, 400 comprises one or more buttons for adding or removing layers 302, one or more buttons for receiving input molecules 304, one or more buttons for adding or removing individual molecules 306, and one or more buttons for importing scores 308.

In some embodiments, the map user interface 300, 400 comprises a plurality of settings selected from the group of navigational settings for the map visualization, plot settings, settings for coding scores in the map visualization, cluster settings, settings for editing samples, sample settings, report settings, map analysis settings, and export settings.

In some embodiments, the processing subsystem causes the system 100 to selectively subtract an unimmunized library of molecules from an immunized library of molecules to filter out nonspecific molecules and to reduce search space for sampling and searching for specific drug-candidate molecules for one or multiple targets; if multiple layers or datasets 106 exist for the immunized library, the subsystem causes the system 100 to selectively intersect the layers after subtraction to further reduce the search space.

In some embodiments, the processing subsystem causes the system 100 to selectively subtract libraries of molecules immunized against one or multiple targets from a library of molecules immunized against a target of interest, to filter out molecules which are non-binders to the target of interest, and to reduce search space for sampling and searching for specific drug-candidate molecules for a target of interest; if multiple layers or datasets 106 exist for the library of molecules immunized against the target of interest, the subsystem causes the system 100 to selectively intersect the layers after subtraction to further reduce the search space.

Implementation Details.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

The embodiments and examples described herein are illustrative and non-limiting. Practical implementation of the features may incorporate a combination of some or all of the aspects, and features described herein should not be taken as indications of future or existing product plans. Applicant partakes in both foundational and applied research, and in some cases, the features described are developed on an exploratory basis.

Of course, the above described embodiments are intended to be illustrative only and in no way limiting. The described embodiments are susceptible to many modifications of form, arrangement of parts, details and order of operation. The disclosure is intended to encompass all such modification within its scope, as defined by the claims.

What is claimed is:

1. A computer-implemented system for mapping proteins, protein-like molecules or fragments thereof into visual interfaces and generating maps for display and interaction, the system comprising:

a processing subsystem that includes one or more processors and one or more memories coupled with the one or more processors, the processing subsystem configured to cause the system to:

receive data for a set or multiple sets of one or more input proteins, protein-like molecules or fragments thereof, wherein the data comprises features of the one or more proteins, protein-like molecules or fragments thereof;

generate at least one dataset by processing the data for the set or multiple sets of the one or more input proteins, protein-like molecules or fragments thereof;

transform one or more of the data and the at least one dataset(s) to generate a map and additional features by feature extraction or feature selection to reduce higher dimensional data representations into lower dimensional data representations for visualization by the visual interface while, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof;

generate a visual map interface comprising the map as a visual representation of the lower dimensional data representations of the dataset, the map having one or more dimensions corresponding to the lower dimensional data, the visual representation comprising visualizations representing the dataset as one or more layers of proteins, protein-like molecules or fragments thereof and wherein the visualizations comprise points on the visual map, with each point representing a protein, protein-like molecule or fragment thereof, and the points are spatially located within the visual map based on the lower dimensional data representations, each layer comprising one or more of the one or more clusters of proteins, protein-like molecules or fragments thereof, wherein spatial arrangement of the points reflects similarity of the represented proteins, protein-like molecules or fragments thereof;

provide the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof;

receive commands or detect interactions with the map by the tools at the visual map interface;

update the map based on the commands or interactions; and trigger an update to the visual map interface with the updated map.

2. The computer-implemented system of claim 1 wherein the proteins, protein-like molecules or fragments thereof are selected from: antibodies, antigens, lectins, receptors, ligands, enzymes, or fragments thereof.

3. The computer-implemented system of claim 2 wherein the proteins, protein-like molecules or fragments thereof comprises antibodies or fragments thereof and/or antigens or fragments thereof, and wherein the map is a paratope map or an epitope map or a map comprising proteins or protein-like molecules or fragments thereof.

4. The computer-implemented system of claim 1 wherein the proteins, protein-like molecules or fragments thereof comprise antibodies or antibody fragments thereof and wherein the data comprises one or more of the structure of one or more antibodies or antibody fragments thereof, the amino acid sequence of one or more of the antibodies or antibody fragments thereof, amino acid atom or molecule coordinates, and biophysical properties of one or more antibodies or antibody fragments thereof.

5. The computer-implemented system of claim 1 wherein the proteins, protein-like molecules or fragments thereof are selected from conventional antibodies, antibody-like molecules, artificial antibodies, antibody mimetics, single domain antibodies, single chain antibody, humanized antibodies, chimeric antibodies, or fragments thereof.

6. The computer-implemented system of claim 5 wherein the fragments comprise antigen binding fragments or antigen binding domains.

7. The computer-implemented system of claim 6 wherein the antigen binding fragments or the antigen binding domains are selected from one or more complementarity determining regions and/or one or more framework regions, one or more variable domains, or paratope.

8. The computer-implemented system of claim 1 wherein the visual representation of the lower dimensional data representations comprises different colours and/or marker shapes and/or marker sizes and/or color transparencies and/or color gradients to indicate the one or more layers and the one or more clusters of proteins, protein-like molecules or fragments thereof.

9. The computer-implemented system of claim 1 wherein the lower dimensional data representations are one-dimensional, two-dimensional, three-dimensional, or four-dimensional data representations.

10. The computer-implemented system of claim 1 wherein the features comprise fingerprints, wherein the processing subsystem extracts features and generates the fingerprints using machine learning or statistical methods involving one or more of dimensionality reduction, a reconstruction autoencoder, a variational autoencoder, adversarial autoencoder, neural networks, graph neural networks, attention networks, recurrent networks, sequence processing algorithms, image processing algorithms, computer vision algorithms, and identity transformation.

11. The computer-implemented system of claim 1 wherein the processing subsystem causes the system to cluster the one or more of the data and the dataset to generate the one or more clusters of proteins, protein-like molecules or fragments thereof.

12. The computer-implemented system of claim 1 wherein the processing subsystem causes the system to encode the raw data and generate additional features from the encoded data.

13. The computer-implemented system of claim 1 wherein the visual representation superimposes the one or more layers of proteins, protein-like molecules or fragments thereof as overlays as part of the visualizations representing the dataset, wherein the tools trigger movement of the one or more layers to different positions or levels, or removal thereof from the map or change of order of displaying the layers or zooming in or out of one or multiple layers or moving in the map across layers.

14. The computer-implemented system of claim 1 wherein the processing subsystem causes the system to implement map analysis, wherein map analysis comprises one or more of generating clusters around proteins, protein-like molecules or fragments thereof of interest, arranging embeddings in clusters, layer-wise embedding, embedding individual proteins, protein-like molecules or fragments thereof, sampling from the map, and coding scores in the map, wherein the map contains the one or more clusters and visualizes the one or more clusters.

15. The computer-implemented system of claim 1 wherein the processing subsystem causes the system to generate or calculate one or more clusters of proteins, protein-like molecules or fragments thereof, and wherein the map user interface comprises a visualization of the one or more clusters of proteins, protein-like molecules or fragments thereof.

16. The computer-implemented system of claim 1 wherein feature extraction comprises extracting useful information from the dataset and feature selection comprises selecting a subset of the dataset of proteins, protein-like molecules or fragments thereof.

17. The computer-implemented system of claim 1 wherein the processing subsystem causes the system to transform the one or more of the data and the dataset to generate the map by one or more of sequencing and clustering, sampling, intersection of data subsets, and subtraction of data subsets.

18. The computer-implemented system of claim 1 wherein processing subsystem causes the system to partition or segment the digital map into a plurality of map tiles, label each of the one or more clusters with a corresponding map tile of the plurality of map tiles, and display the one or more clusters within the plurality of map tiles using the labels, wherein the visualization indicates the plurality of map tiles and the one or more clusters.

19. The computer-implemented system of claim 1 wherein the processing subsystem causes the system to: (i) intersect one or more layers of proteins, protein-like molecules or fragments thereof or (ii) subtract one or more layers of proteins, protein-like molecules or fragments thereof or (iii) add one or more layers of proteins, protein-like molecules or fragments thereof, to update the map based on the commands or interactions.

20. The computer-implemented system of claim 1 wherein the tools at the visual map interface comprises a sampling tool for sampling proteins, protein-like molecules or fragments thereof from the one or more clusters of proteins, protein-like molecules or fragments thereof, wherein the processing subsystem causes the system to update the map by sampling proteins, protein-like molecules or fragments thereof in response to activation of the sampling tool and trigger an update to the visual map interface with the updated map to visualize the sampling.

21. The computer-implemented system of claim 1 wherein the processing subsystem causes the system to subtract the unimmunized library of proteins, protein-like molecules or fragments thereof from the immunized library of proteins, protein-like molecules or fragments thereof to filter out nonspecific proteins, protein-like molecules or fragments thereof and to reduce the search space for sampling and searching for specific molecule-candidates for one or multiple targets, wherein if multiple layers or datasets exist for the immunized library, the subsystem causes the system to intersect layers or datasets after subtraction to reduce the search space even further.

22. The computer-implemented system of claim 1 wherein the processing subsystem causes the system to subtract the libraries of proteins, protein-like molecules or fragments thereof immunized against one or multiple targets from the library of proteins, protein-like molecules or fragments thereof immunized against a target of interest, to filter out moieties which are non-binders to the target of interest, and to reduce the search space for sampling and searching for specific molecule-candidates for the target of interest, wherein if multiple layers or datasets exist for the immunized library against the target of interest, the subsystem causes the system to intersect layers or datasets after subtraction to reduce the search space even further.

23. The computer-implemented system of claim 1 wherein the processing subsystem causes the system to export or report the inspection, searching, sampling, clustering, and analysis of the proteins, protein-like molecules or fragments thereof through text, tables, plots, or visualizations.

24. A computer process for mapping proteins, protein-like molecules or fragments thereof into visual interfaces and generating digital maps for display and interaction, the method comprising:

receiving data for a set or multiple sets of one or more input proteins, protein-like molecules or fragments thereof, wherein the data comprises features of the one or more proteins, protein-like molecules or fragments thereof;

generating at least one dataset by processing the data for the set or multiple sets of the one or more input proteins, protein-like molecules or fragments thereof;

transforming one or more of the data and the at least one dataset(s) to generate a map and additional features by feature extraction or feature selection to reduce higher dimensional data representations into lower dimensional data representations for visualization by the visual interface while, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof;

generating a visual map interface comprising the map as a visual representation of the lower dimensional data representations of the dataset, the map having one or more dimensions corresponding to the lower dimensional data, the visual representation comprising visualizations representing the dataset as one or more layers of proteins, protein-like molecules or fragments thereof and wherein the visualizations comprise points on the visual map, with each point representing a protein, protein-like molecule or fragment thereof, and the points are spatially located within the visual map based on the lower dimensional data representations, each layer comprising one or more of the one or more clusters of proteins, protein-like molecules or fragments thereof, wherein spatial arrangement of the points reflects similarity of the represented proteins, protein-like molecules or fragments thereof; and providing the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof;

receiving commands or detect interactions with the map by the tools at the visual map interface; and triggering an update to the visual map interface and the map based on the commands or interactions.

25. A non-transitory computer-readable medium encoded with instructions, that when executed by a processor, cause the processor to map proteins, protein-like molecules or fragments thereof into visual interfaces and generate digital maps for display and interaction, the instructions comprising instructions for:

receiving data for a set or multiple sets of one or more input proteins, protein-like molecules or fragments thereof, wherein the data comprises features of the one or more proteins, protein-like molecules or fragments thereof;

generating at least one dataset by processing the data for the set or multiple sets of the one or more input proteins, protein-like molecules or fragments thereof;

transforming one or more of the data and the at least one dataset(s) to generate a map and additional features by feature extraction or feature selection to reduce higher dimensional data representations into lower dimensional data representations for visualization by the visual interface while, wherein the lower-dimensional data representations capture valuable information of the one or more of the data and the at least one dataset(s), the lower dimensional data representations comprising one or more clusters of proteins, protein-like molecules or fragments thereof, the proteins, protein-like molecules or fragments thereof comprising the one or more input proteins, protein-like molecules or fragments thereof or generated proteins, protein-like molecules or fragments thereof;

generating a visual map interface comprising the map as a visual representation of the lower dimensional data representations of the dataset, the map having one or more dimensions corresponding to the lower dimensional data, the visual representation comprising visualizations representing the dataset as one or more layers of proteins and wherein the visualizations comprise points on the visual map, with each point representing a protein, protein-like molecule or fragment thereof, and the points are spatially located within the visual map based on the lower dimensional data representations, protein-like molecules or fragments thereof, each layer comprising one or more of the one or more clusters of proteins, protein-like molecules or fragments thereof, wherein spatial arrangement of the points reflects similarity of the represented proteins, protein-like molecules or fragments thereof; and providing the visual map interface with tools for interaction with the map, wherein interaction with the map comprises one or more of inspection, searching, sampling, clustering, and analysis of the one or more proteins, protein-like molecules or fragments thereof or newly generated proteins, protein-like molecules or fragments thereof;

receiving commands or detect interactions with the map by the tools at the visual map interface; and triggering an update to the visual map interface and the map based on the commands or interactions.

* * * * *

SEQUENCE LISTING

```
Sequence total quantity: 3
SEQ ID NO: 1           moltype = AA  length = 35
FEATURE                Location/Qualifiers
source                 1..35
                       mol_type = protein
                       organism = unidentified
SEQUENCE: 1
QVQLEESGGG LVQAGDSLTL SCVASGRTFS SYAMG                              35

SEQ ID NO: 2           moltype = AA  length = 35
FEATURE                Location/Qualifiers
source                 1..35
                       mol_type = protein
                       organism = unidentified
SEQUENCE: 2
QVQLEESGGE LVQAGGSLRL SCVASGLTSN RYNMG                              35

SEQ ID NO: 3           moltype = AA  length = 35
FEATURE                Location/Qualifiers
source                 1..35
                       mol_type = protein
                       organism = unidentified
SEQUENCE: 3
QVQLEESGGE LVQAGGSLRL SCVASGLTSN RYNMG                              35
```